(12) United States Patent
Kawamura et al.

(10) Patent No.: US 8,530,392 B2
(45) Date of Patent: Sep. 10, 2013

(54) TEST AGENT FOR VISCERAL OBESITY AND USE THEREOF

(75) Inventors: Yoshihiro Kawamura, Osaka (JP); Masatomo Rokushima, Osaka (JP); Minoru Suzuki, Shiga (JP); Tatsuya Takahashi, Osaka (JP); Minoru Ikeda, Osaka (JP); Atsunori Kashiwagi, Shiga (JP); Hiroshi Maegawa, Shiga (JP); Tohru Tani, Shiga (JP); Shiro Maeda, Kanagawa (JP)

(73) Assignees: Shionogi & Co., Ltd., Osaka (JP); Shiga University of Medical Science, Shiga (JP); Riken, Saitama (JP)

( * ) Notice: Subject to any disclaimer, the term of this patent is extended or adjusted under 35 U.S.C. 154(b) by 0 days.

(21) Appl. No.: 13/319,717

(22) PCT Filed: May 13, 2010

(86) PCT No.: PCT/JP2010/058097
§ 371 (c)(1),
(2), (4) Date: Nov. 10, 2011

(87) PCT Pub. No.: WO2010/131704
PCT Pub. Date: Nov. 18, 2010

(65) Prior Publication Data
US 2012/0066777 A1    Mar. 15, 2012

(30) Foreign Application Priority Data

May 13, 2009 (JP) ................................ 2009-116323

(51) Int. Cl.
*C40B 30/04* (2006.01)
(52) U.S. Cl.
USPC ........................................................... 506/9
(58) Field of Classification Search
None
See application file for complete search history.

(56) References Cited

U.S. PATENT DOCUMENTS

| | | | |
|---|---|---|---|
| 2003/0113889 A1 | 6/2003 | Gimeno et al. | |
| 2009/0092991 A1* | 4/2009 | Feilotter et al. | 435/6 |
| 2009/0163435 A1* | 6/2009 | Bader et al. | 514/44 |

FOREIGN PATENT DOCUMENTS

| | | |
|---|---|---|
| JP | 2003-514513 | 4/2003 |
| JP | 2007-54002 | 3/2007 |
| JP | 2009-27985 | 2/2009 |
| JP | 2009-27986 | 2/2009 |
| WO | 01/20031 | 3/2001 |

OTHER PUBLICATIONS

Kim et al. (Genes Nutr. 2010; 5: 237-250, published online Dec. 18, 2009).*
Eberlein et al. (Comparative Biochemistry and Physiology. 2010, Part B, 156: 19-25; published online Feb. 1, 2010).*
Nishida, M. et al., Pathophysiological significance of adiponectin, Medical Molecular Morphology, 2007, vol. 40, No. 2, pp. 55-67.
Supplementary European Search Report dated Nov. 28, 2012, issued in corresponding European Application No. 10774961.6.
Kobayashi, S. et al., Identification of a new secretory factor, CCDC3/Favine, in adipocytes and endothelial cells, Biochem. Biophys. Res. Commun., 2010, vol. 392, pp. 29-35.
Eberlein, A. et al., Analysis of structure and gene expression of bovine CCDC3 gene indicates a function in fat metabolism, Comp. Biochem. Physiol., Part B, 2010, vol. 156, pp. 19-25.
Cleeman, J. et al., Executive summary of the third report of the national cholesterol education program (NCEP) expert panel on detection, evaluation, and treatment of high blood cholesterol in adults (adult treatment panel III), JAMA, 2001, vol. 285, No. 19,pp. 2486-2497.
The Japanese Society of Internal Medicine, 2005, vol. 94, pp. 794-809.
Matsuzawa, Y. et al., New criteria for 'obesity disease' in Japan, Circ J, 2002, vol. 66, pp. 987-992.
Degenhardt, L. et al., UK classification of cannabis: is a change needed and why?, Lancet, 2007, vol. 370, pp. 1541-1542.
Yamamoto, S. et al., Development of the automated diagnosis system CT screening for visceral obesity, MEDIX, 2004, vol. 41, pp. 15-20.
Pollex, R. et al., Genetic determinants of the metabolic syndrome, Nat. Clin. Pract. Cardiovasc. Med., 2006, vol. 3, No. 9, pp. 482-489.
Perusse, L. et al., The human obesity gene map: the 2004 update, Obesity Research, 2005, vol. 13, No. 3, pp. 381-490.
Aoki, K. et al., Dehydroepiandrosterone decreases elevated hepatic glucose production in C57BL/KsJ-db/db mice, Life Sciences, 2004, vol. 74, pp. 3075-3084.
Consoli, A. et al., Predominant role of gluconeogenesis in increased hepatic glucose production in NIDDM, Diabetes, 1989, vol. 38, pp. 550-557.
International Search Report for PCT/JP2010/058097, dated Jun. 8, 2010.

* cited by examiner

*Primary Examiner* — Scott Long
(74) *Attorney, Agent, or Firm* — Roylance, Abrams, Berdo & Goodman, L.L.P.

(57) ABSTRACT

Disclosed are: a method for detecting (diagnosing) visceral obesity in a subject; a test agent useful for the method; a method for searching for a substance that can be used as an active ingredient for ameliorating visceral obesity; and an ameliorating agent for visceral obesity or a medicinal agent for preventing a metabolic disease developed as a result of the progression of visceral obesity. As the test agent, a polynucleotide which comprises at least 15 nucleotides and can hybridize with a nucleotide sequence for coiled-coil domain containing protein 3 (CCDC3) gene or a nucleotide sequence complementary to the nucleotide sequence under stringent conditions or an antibody capable of recognizing CCDC3 protein is used.

2 Claims, 16 Drawing Sheets

```
                           SEQUENCE LISTING

<160> NUMBER OF SEQ ID NOS: 53

<210> SEQ ID NO 1
<211> LENGTH: 2753
<212> TYPE: DNA
<213> ORGANISM: Homo sapiens

<400> SEQUENCE: 1
cccgtggcgg agacagcggt gcgctcagct cccgggagcg gcccgagcag ccgagcgccc      60
agggctgccc ttcccgggcc ggcgggctcc ccgggctccc cgccgccgcc ccgtgcgccc     120
cgggagggcc cggcatgctg cgccagctgc tgctcgccgc gctctgcctg gcgggtcccc     180
cagcgcccgc gcgcgcctgc cagctgccct ccgagtggag gccccctgagc gagggctgcc     240 gcgccgagct ggccgagacc atcgtgtacg ccagggtgct ggcgctgcac cccgaggcgc     300
ccggcctcta caaccacctg ccctggcagt accacgccgg ccaggggggc ctcttctact     360
cggccgaggt cgagatgctg tgcgaccagg cgtggggcag catgctggag gtgcccgccg     420
gctccaggct caacctcacc ggcctgggct acttctcgtg ccactcccac accgtggtcc     480
aggactactc ctatttcttc ttcctcagga tggatgaaaa ttataacctc ttgcctcacg     540
gagtcaattt ccaagatgcc atcttcccag acactcaaga gaacagaagg atgttttcta     600
gccttttcca gtttttcaaac tgttcgcaag ggcagcagct ggcgactttc tccagtgact     660
gggaaatcca ggaagacagt aggctcatgt gctcctcggt gcagaaggcc ttgtttgagg     720
aggaggacca cgtcaagaaa ctgcagcaga agtggccac cctggagaag cgcaaccggc     780
agctccggga gcgagtgaag aaggtcaaga ggtccttgcg gcaggcgcgt aagaagggcc     840
gccacctgga gctggcgaac cagaaactca gtgagaagct ggcggcgggc gcgctgccgc     900
acatcaacgc ccgggggccc gtgcgccccc cctacctgcg ggggtaacgg gcctggggc      960 tgccaggtgt gcagggccaa tcctggcggt aattgagaat gagtgaggtt tcgtacatgc    1020
agctatttca agggttgtaa gagtttttgt ttttaatcac gcatttggta gagtctaaat    1080
ggataaaatg caaggcttgc tttcccttg ggtgctggcc tcaatgtcag accccacgcg     1140 ctgcccttc ctggcctgac cccagacgca gtgcctggca gtccagaggc agtgggatcc     1200
ctgagtgctg aatgctcgcc tgcagagcag cccagaaaga gccctgactg gggagagaac    1260
attttagaat ctctagtgta aaagacatca acgtgcttag cctttatttc agaaaaaaat    1320
cagggtggtt cccagctccc cagtccagga caaccattag tcctgatgag tgagctgacg    1380
```

```
ctggtgctgg aacctgctgg cacctcactg gccacatctt tggaagggga tggtggcctt    1440
gcatccaaga tgcctgaaaa tcagcacgtg cagggcctcc ctatccagcc agcatttcc     1500 ttccagctga ggcaggtgaa gacttcataa gctcatcaca ggggagggaa ttaggagcag    1560
ggcagcaggt aattaaacaa gataaattat acctgatttc aacaccagc tacaaagagt     1620 tgaagatgat acctatgggt cgcgttaaca caggggcaa ctgccttgat cggcctgcca     1680
tgggtcatca gactgcttcc taaattgaga gaaactgagc aatctctcag ccactgctat    1740
agtctaactt cttgtttgct gagtaattgt ttctaatgtc tctgaactca aagtgaggtg    1800
ctccaagacg ctgtgaactt ctgcaaagac acctccttac ctactgggat cacgtgacct    1860
gacctcactc ccagccaggc tcccaaaggg ctcattccag ccattccaat ctcttcttct    1920
ttatgcaaac actttttcccc cacaacaagc cttgtttgtt ccgataggaa tacgtgtacg    1980
tcagtgcact tgtccttacg tcagttcctt acaccaccaa agcacttcac ctttctggaa    2040
ataaaacttt taagacacta ctataagtaa aaatgagagt attcactaga cttattgctc    2100
aggcacattt gagtgggtcc cagctgtgtg attaagaagt caactgggtg ccttttctg     2160 ggttatcttc tgatcatggc cttcaaccc aacaagggcc cttccctgct cttccaccag     2220
taaaggctcc tggcctctca tcaggatctg ccccccagag acccccccag acactgcagg    2280
gcctggtgat gctgtcctct gtaccggaaa tggcaggcac tgtcagattt ccactcttct    2340
gcctttagga aggctgggtg cttcttgctc tgacagccag tctggggaga tgactcttac    2400
gttgcttgag tcttggtggc aggctgctgt ccacggggga gaagtctctg ctctggactg    2460
gacagaagag agacttttac cctggggcac tcacacggcc aagcttctgc caccacttca    2520
ttagctgtat tctccatagt atggtgaaat agcaggtgcg tcttctagtt tattcctcct    2580
ggggacattt cctcaaagca gttttgcgcc cccgcaaggg aatggtcagc ctaagggtaa    2640
tgtacagccc gtgcttggag aaccatggaa gctacacccc tacaggtgca tactgttctg    2700
cttttccaat aaatacgagc ggcgatttca accacaaaaa aaaaaaaaaa aaa           2753

<210> SEQ ID NO 2
<211> LENGTH: 2769
<212> TYPE: DNA
<213> ORGANISM: Mus musculus

<400> SEQUENCE: 2
gccgaagagc tagccgtgca cccagctctc cggagcgcgt gcaggcgagc cgagcgcccc      60
gtccgcggtt ctcgggcagg cgctgcgggc tccccggctc cccgccgtcc cgggcacccg     120
ggcgggccat gcgcccgggc tagagcgtag ccgccggcat gccgctcccg ctgctgctcg     180
ccgcgctctg cctcgccgcc tccccggcgc ccgcgcgcgc ctgccagctg ccgtcggagt     240 ggagacccctt gagcgaaggc tgccgcgccg agctagccga gaccatcgtg tatgccaagg     300
tgctggcgct gcaccccgag gtgcctggcc tctacaacta cctgccgtgg cagtaccaag     360
ctggagaggg agggctcttc tactccgccg aggtggagat gctgtgtgac aggcgtggg     420 gcagtatgtt ggaggtgccc gccggctccc ggctcaacct tactggtctg ggctacttct    480
cctgccactc ccacacggtg gtccaggact actcttattt cttctttgta aggatggatg    540
agaattacaa tctcttgcca cacggagtca atttccaaga tgccatcttt ccagacaccc    600
aggagaacag aaggatgttt tccagccttt tccagtttgc taactgttcc caagggcagc    660
agctgacgac tttctcgagt gactgggagg tccaggaaga caacaggctc atgtgctcct    720
cggtgcagaa ggccctgtttt gaggaagagg accatgtcaa gaagctgcag cagaaggtgg    780
```

```
ccaccctgga gaagcggaac aggcagctcc gagagcgggt caagaaggtc aagaggtctc    840
tgaggcaggc acggaagaac agccgccacc tggagctggt gaaccaaaaa ctcaatgaga    900
agctaggggc tccagtgct cagcagcaca ttaacgctct gggccgggag ccgtgcgtg     960
cccctatct gcatgggtag caggggcagg tggatgctgg cctgccttgc ctgtgccggc   1020
tgactgagaa caaccgcaag ctctatatat gcacttactt caaacattat agtagctatc  1080
catttggcat ttggtagagt ctaactgggt aaattgtcag gttttgcttt ctttcccatt  1140
gggtcctggc cttactggcc atttgacttc agatcccatg tgccacatgt cctctttctg  1200
tcctggtgcc acacaagagc cttaaaaccg gaaggcaata gtatcttgag tctggccctc  1260
agcctctaga gagttccttc gctgggggga aacattcta gaacctcggt atacatgaag   1320
atatcacagg actctcttgt ttcagaaggg agtcggtgtt gaggctcagc aaccagggtt  1380
ggcacacgca tgcgtgttct aaaatgttct ggaatgttct gccttttctc gtgtttttag  1440
aaatggtgtc tacgtgtaaa tgtgcagggc acccacccgt gcttcagtca ccatttctcc  1500
caaagctgaa agatgttaag acttaatgag ttcattacag gtaagggaac tgggcgagga  1560
gctgaggcag ctagtaattg gtaaagataa attatatctg ttttccaacc ccagctcctt  1620
ggggctgaca tgattcccta caggatgttt taatctaaag cgtaattgct tttatagaca  1680
taccatattt catcactcat gtttccaaac tggaattaag ctcaacctaa ctttgtggag  1740
tcttaacttt gtgttagcgc agcttgccat ggctccgagt ttaaggtcac tgacttgcac  1800
acactgagac tttctactct gcagaaacag ctccctgcct gaagggttc aataagctct   1860
atgctagggt cccaaagggc tttgtccagg gattctaacc caagcttcta tgcaacctcc  1920
aagcctctga cccaacacac acacacacac acacacacac acactgctca              1980
ggttctcata aaaggtctac gtgtacccca tagaagtatt tgcataacaa acactttctt  2040
ttaataagag tgcttttcact atccttccca tggccatgtt tgatcatgtc ccatttgtgt  2100
tactaagaag tcaatggagt ggctgctggt tcatcgcctc taatggtggc cctccagatc  2160
taatgccgtg ccacactgtt ccaccaatag aaagaatcct tcagctctac accattgacc  2220
acctagaacc cattccagac acatgatact gataaaagtg gtcattactg tcacactgcc  2280
gcctttctgc ttgcaggaag tccaggcctc tgtgagaagt ccctcctgtc acatgagtat  2340
tggtagggggt ggggataagt ttgtgccctt ggctggtcag ggcatgatgg gaaggaactt  2400
ctattctggg accaatcttc atccactctc ccccactcag cctctttaag cagtgctatt  2460
cataatatgc tacagaggtg tgccttctca ttaattctcc ctgggagcat taagttaaag  2520
cgcttttgtt acctcccaag ggaatgaatg gcaagcttag gggtgatgga gtcaggactc  2580
ggagaactgt ggaagccgaa gatgtcttat gttctgcttt tccaataaac atgagcagtg  2640
cttccaatgg ctgtggaaaa aaaaaaaaaa aaaaaaaaaa aaaaaaaaaa aaaaaaaaaa  2700
aaaaaaaaaa aaaaaaaaaa aaaaaaaaaa aaaaaaaaaa aaaaaaaaaa aaaaaaaaaa  2760
aaaaaaaaa                                                         2769
```

<210> SEQ ID NO 3
<211> LENGTH: 270
<212> TYPE: PRT
<213> ORGANISM: Homo sapiens

<400> SEQUENCE: 3

Met Leu Arg Gln Leu Leu Leu Ala Ala Leu Cys Leu Ala Gly Pro Pro
1               5                   10                  15

Ala Pro Ala Arg Ala Cys Gln Leu Pro Ser Glu Trp Arg Pro Leu Ser

```
                    20                  25                  30
Glu Gly Cys Arg Ala Glu Leu Ala Glu Thr Ile Val Tyr Ala Arg Val
            35                  40                  45

Leu Ala Leu His Pro Glu Ala Pro Gly Leu Tyr Asn His Leu Pro Trp
 50                  55                  60

Gln Tyr His Ala Gly Gln Gly Leu Phe Tyr Ser Ala Glu Val Glu
 65                  70                  75                  80

Met Leu Cys Asp Gln Ala Trp Gly Ser Met Leu Glu Val Pro Ala Gly
                    85                  90                  95

Ser Arg Leu Asn Leu Thr Gly Leu Gly Tyr Phe Ser Cys His Ser His
                100                 105                 110

Thr Val Val Gln Asp Tyr Ser Tyr Phe Phe Phe Leu Arg Met Asp Glu
                115                 120                 125

Asn Tyr Asn Leu Leu Pro His Gly Val Asn Phe Gln Asp Ala Ile Phe
            130                 135                 140

Pro Asp Thr Gln Glu Asn Arg Arg Met Phe Ser Ser Leu Phe Gln Phe
145                 150                 155                 160

Ser Asn Cys Ser Gln Gly Gln Gln Leu Ala Thr Phe Ser Ser Asp Trp
                165                 170                 175

Glu Ile Gln Glu Asp Ser Arg Leu Met Cys Ser Ser Val Gln Lys Ala
                180                 185                 190

Leu Phe Glu Glu Asp His Val Lys Lys Leu Gln Gln Lys Val Ala
                195                 200                 205

Thr Leu Glu Lys Arg Asn Arg Gln Leu Arg Glu Arg Val Lys Lys Val
            210                 215                 220

Lys Arg Ser Leu Arg Gln Ala Arg Lys Lys Gly Arg His Leu Glu Leu
225                 230                 235                 240

Ala Asn Gln Lys Leu Ser Glu Lys Leu Ala Ala Gly Ala Leu Pro His
                245                 250                 255

Ile Asn Ala Arg Gly Pro Val Arg Pro Pro Tyr Leu Arg Gly
                260                 265                 270

<210> SEQ ID NO 4
<211> LENGTH: 273
<212> TYPE: PRT
<213> ORGANISM: Mus musculus

<400> SEQUENCE: 4

Met Pro Leu Pro Leu Leu Leu Ala Ala Leu Cys Leu Ala Ser Pro
 1                   5                  10                  15

Ala Pro Ala Arg Ala Cys Gln Leu Pro Ser Glu Trp Arg Pro Leu Ser
                    20                  25                  30

Glu Gly Cys Arg Ala Glu Leu Ala Glu Thr Ile Val Tyr Ala Lys Val
            35                  40                  45

Leu Ala Leu His Pro Glu Val Pro Gly Leu Tyr Asn Tyr Leu Pro Trp
 50                  55                  60

Gln Tyr Gln Ala Gly Glu Gly Gly Leu Phe Tyr Ser Ala Glu Val Glu
 65                  70                  75                  80

Met Leu Cys Asp Gln Ala Trp Gly Ser Met Leu Glu Val Pro Ala Gly
                    85                  90                  95

Ser Arg Leu Asn Leu Thr Gly Leu Gly Tyr Phe Ser Cys His Ser His
                100                 105                 110

Thr Val Val Gln Asp Tyr Ser Tyr Phe Phe Phe Val Arg Met Asp Glu
                115                 120                 125

Asn Tyr Asn Leu Leu Pro His Gly Val Asn Phe Gln Asp Ala Ile Phe
```

```
            130                 135                 140
Pro Asp Thr Gln Glu Asn Arg Arg Met Phe Ser Ser Leu Phe Gln Phe
145                 150                 155                 160

Ala Asn Cys Ser Gln Gly Gln Gln Leu Thr Thr Phe Ser Ser Asp Trp
            165                 170                 175

Glu Val Gln Glu Asp Asn Arg Leu Met Cys Ser Ser Val Gln Lys Ala
            180                 185                 190

Leu Phe Glu Glu Asp His Val Lys Lys Leu Gln Gln Lys Val Ala
            195                 200                 205

Thr Leu Glu Lys Arg Asn Arg Gln Leu Arg Glu Arg Val Lys Val
210                 215                 220

Lys Arg Ser Leu Arg Gln Ala Arg Lys Asn Ser Arg His Leu Glu Leu
225                 230                 235                 240

Val Asn Gln Lys Leu Asn Glu Lys Leu Gly Ala Ser Ser Ala Gln Gln
            245                 250                 255

His Ile Asn Ala Leu Gly Arg Glu Pro Val Arg Ala Pro Tyr Leu His
            260                 265                 270

Gly

<210> SEQ ID NO 5
<211> LENGTH: 19
<212> TYPE: RNA
<213> ORGANISM: Artificial Sequence
<220> FEATURE:
<223> OTHER INFORMATION: siRNA #1, sense strand r
<220> FEATURE:
<221> NAME/KEY: modified_base
<222> LOCATION: (19)..(19)
<223> OTHER INFORMATION: Modified by gdTdTh

<400> SEQUENCE: 5
gacacaugau acugauaaa                                              19

<210> SEQ ID NO 6
<211> LENGTH: 19
<212> TYPE: RNA
<213> ORGANISM: Artificial Sequence
<220> FEATURE:
<223> OTHER INFORMATION: siRNA #1, antisense strand r
<220> FEATURE:
<221> NAME/KEY: modified_base
<222> LOCATION: (19)..(19)
<223> OTHER INFORMATION: Modified by gdTdGh

<400> SEQUENCE: 6
uuuaucagua ucauguguc                                              19

<210> SEQ ID NO 7
<211> LENGTH: 19
<212> TYPE: RNA
<213> ORGANISM: Artificial Sequence
<220> FEATURE:
<223> OTHER INFORMATION: siRNA #2, sense strand r
<220> FEATURE:
<221> NAME/KEY: modified_base
<222> LOCATION: (19)..(19)
<223> OTHER INFORMATION: Modified by gdTdTh

<400> SEQUENCE: 7
gaaagauguu aagacuuaa                                              19

<210> SEQ ID NO 8
<211> LENGTH: 19
<212> TYPE: RNA
```

```
<213> ORGANISM: Artificial Sequence
<220> FEATURE:
<223> OTHER INFORMATION: siRNA #2, antisense strand r
<220> FEATURE:
<221> NAME/KEY: modified_base
<222> LOCATION: (19)..(19)
<223> OTHER INFORMATION: Modified by gdAdGh

<400> SEQUENCE: 8
uuaagucuua acaucuuuc                                                      19

<210> SEQ ID NO 9
<211> LENGTH: 19
<212> TYPE: RNA
<213> ORGANISM: Artificial Sequence
<220> FEATURE:
<223> OTHER INFORMATION: siRNA #3, sense strand r
<220> FEATURE:
<221> NAME/KEY: modified_base
<222> LOCATION: (19)..(19)
<223> OTHER INFORMATION: Modified by gdTdTh

<400> SEQUENCE: 9
gaaguauuug cauaacaaa                                                      19

<210> SEQ ID NO 10
<211> LENGTH: 19
<212> TYPE: RNA
<213> ORGANISM: Artificial Sequence
<220> FEATURE:
<223> OTHER INFORMATION: siRNA #3, antisense strand r
<220> FEATURE:
<221> NAME/KEY: modified_base
<222> LOCATION: (19)..(19)
<223> OTHER INFORMATION: Modified by gdTdAh

<400> SEQUENCE: 10
uuuguuaugc aaauacuuc                                                      19

<210> SEQ ID NO 11
<211> LENGTH: 21
<212> TYPE: DNA
<213> ORGANISM: Artificial Sequence
<220> FEATURE:
<223> OTHER INFORMATION: Forward primer for amplifying G6Pase

<400> SEQUENCE: 11
tgcgtgccat aggactcatc a                                                   21

<210> SEQ ID NO 12
<211> LENGTH: 21
<212> TYPE: DNA
<213> ORGANISM: Artificial Sequence
<220> FEATURE:
<223> OTHER INFORMATION: Reverse primer for amplifying G6Pase

<400> SEQUENCE: 12
agcaaacaat tgcccaccgt a                                                   21

<210> SEQ ID NO 13
<211> LENGTH: 24
<212> TYPE: DNA
<213> ORGANISM: Artificial Sequence
<220> FEATURE:
<223> OTHER INFORMATION: Forward primer for amplifying Rps18

<400> SEQUENCE: 13
aagtttcagc acatcctgcg agta                                                24
```

<210> SEQ ID NO 14
<211> LENGTH: 24
<212> TYPE: DNA
<213> ORGANISM: Artificial Sequence
<220> FEATURE:
<223> OTHER INFORMATION: Reverse primer for amplifying Rps18

<400> SEQUENCE: 14
ttggtgaggt caatgtctgc tttc                                        24

<210> SEQ ID NO 15
<211> LENGTH: 22
<212> TYPE: DNA
<213> ORGANISM: Artificial Sequence
<220> FEATURE:
<223> OTHER INFORMATION: Forward primer for amplifying mouse CCDC3 gene
      in real-time quantitative PCR

<400> SEQUENCE: 15
tggttcatcg cctctaatgg tg                                          22

<210> SEQ ID NO 16
<211> LENGTH: 23
<212> TYPE: DNA
<213> ORGANISM: Artificial Sequence
<220> FEATURE:
<223> OTHER INFORMATION: Reverse primer for amplifying mouse CCDC3 gene
      in real-time quantitative PCR

<400> SEQUENCE: 16
tggaatgggt tctaggtggt caa                                         23

<210> SEQ ID NO 17
<211> LENGTH: 21
<212> TYPE: DNA
<213> ORGANISM: Artificial Sequence
<220> FEATURE:
<223> OTHER INFORMATION: Forward primer for amplifying mouse 36B4 gene
      in real-time quantitative PCR

<400> SEQUENCE: 17
caacggcagc atttataacc c                                           21

<210> SEQ ID NO 18
<211> LENGTH: 21
<212> TYPE: DNA
<213> ORGANISM: Artificial Sequence
<220> FEATURE:
<223> OTHER INFORMATION: Reverse primer for amplifying mouse 36B4 gene
      in real-time quantitative PCR

<400> SEQUENCE: 18
cccattgatg atggagtgtg g                                           21

<210> SEQ ID NO 19
<211> LENGTH: 33
<212> TYPE: DNA
<213> ORGANISM: Artificial Sequence
<220> FEATURE:
<223> OTHER INFORMATION: CCDC3 EcoRI-F3 primer

<400> SEQUENCE: 19
gcgaattcta gccgtgcacc cagctctccg gag                              33

<210> SEQ ID NO 20
<211> LENGTH: 35
<212> TYPE: DNA

```
<213> ORGANISM: Artificial Sequence
<220> FEATURE:
<223> OTHER INFORMATION: CCDC3 BamHI-R3 primer

<400> SEQUENCE: 20
gcggatccta gagcttgcgg ttgttctcag tcagc                              35

<210> SEQ ID NO 21
<211> LENGTH: 33
<212> TYPE: DNA
<213> ORGANISM: Artificial Sequence
<220> FEATURE:
<223> OTHER INFORMATION: CCDC3 Kozak-F primer

<400> SEQUENCE: 21
gcgaattcca ccatgccgct cccgctgctg ctc                                33

<210> SEQ ID NO 22
<211> LENGTH: 29
<212> TYPE: DNA
<213> ORGANISM: Artificial Sequence
<220> FEATURE:
<223> OTHER INFORMATION: CCDC3 STOP-R primer

<400> SEQUENCE: 22
gcggatccct acccatgcag atagggggc                                     29

<210> SEQ ID NO 23
<211> LENGTH: 20
<212> TYPE: DNA
<213> ORGANISM: Artificial Sequence
<220> FEATURE:
<223> OTHER INFORMATION: CCDC3-F1 primer

<400> SEQUENCE: 23
ggagagggag ggctcttcta                                               20

<210> SEQ ID NO 24
<211> LENGTH: 20
<212> TYPE: DNA
<213> ORGANISM: Artificial Sequence
<220> FEATURE:
<223> OTHER INFORMATION: CCDC3-R1 primer

<400> SEQUENCE: 24
gttctcctgg gtgtctggaa                                               20

<210> SEQ ID NO 25
<211> LENGTH: 24
<212> TYPE: DNA
<213> ORGANISM: Artificial Sequence
<220> FEATURE:
<223> OTHER INFORMATION: CCDC3-QPCR-F primer

<400> SEQUENCE: 25
gctcaacctt actggtctgg gcta                                          24

<210> SEQ ID NO 26
<211> LENGTH: 24
<212> TYPE: DNA
<213> ORGANISM: Artificial Sequence
<220> FEATURE:
<223> OTHER INFORMATION: CCDC3-QPCR-R primer

<400> SEQUENCE: 26
catcttggaa attgactccg tgtg                                          24
```

<210> SEQ ID NO 27
<211> LENGTH: 20
<212> TYPE: DNA
<213> ORGANISM: Artificial Sequence
<220> FEATURE:
<223> OTHER INFORMATION: mGAPDH-QPCR-F primer

<400> SEQUENCE: 27
aaatggtgaa ggtcggtgtg                                               20

<210> SEQ ID NO 28
<211> LENGTH: 18
<212> TYPE: DNA
<213> ORGANISM: Artificial Sequence
<220> FEATURE:
<223> OTHER INFORMATION: mGAPDH-QPCR-R primer

<400> SEQUENCE: 28 tgaagggtc gttgatgg                                                  18

<210> SEQ ID NO 29
<211> LENGTH: 12
<212> TYPE: PRT
<213> ORGANISM: Homo sapiens

<400> SEQUENCE: 29

Ala Arg Gly Pro Val Arg Pro Pro Tyr Leu Arg Gly
1               5                   10

<210> SEQ ID NO 30
<211> LENGTH: 119
<212> TYPE: PRT
<213> ORGANISM: Homo sapiens

<400> SEQUENCE: 30

Gln Ile Gln Leu Val Gln Ser Gly Pro Glu Leu Lys Lys Pro Gly Glu
1               5                   10                  15

Thr Val Lys Ile Ser Cys Lys Ala Ser Gly Tyr Thr Phe Thr Asn Tyr
            20                  25                  30

Gly Met Ile Trp Val Lys Gln Ala Pro Gly Lys Asp Leu Lys Trp Met
        35                  40                  45

Ala Trp Ile Asn Thr Tyr Ser Gly Glu Pro Thr Cys Ala Asp Asp Phe
    50                  55                  60

Lys Gly Arg Phe Ala Phe Ser Leu Glu Thr Ser Ala Ser Thr Ala Tyr
65                  70                  75                  80

Leu Gln Ile Asn Asn Leu Lys Asn Glu Asp Met Ala Thr Tyr Phe Cys
                85                  90                  95

Ala Arg Asp Asp Gly Tyr Tyr Gly Tyr Phe Asp Tyr Trp Gly Gln Gly
            100                 105                 110

Thr Thr Leu Thr Val Ser Ser
        115

<210> SEQ ID NO 31
<211> LENGTH: 5
<212> TYPE: PRT
<213> ORGANISM: Homo sapiens

<400> SEQUENCE: 31

Asn Tyr Gly Met Ile
1               5

<210> SEQ ID NO 32

```
<211> LENGTH: 17
<212> TYPE: PRT
<213> ORGANISM: Homo sapiens

<400> SEQUENCE: 32

Trp Ile Asn Thr Tyr Ser Gly Glu Pro Thr Cys Ala Asp Asp Phe Lys
1               5                   10                  15

Gly

<210> SEQ ID NO 33
<211> LENGTH: 10
<212> TYPE: PRT
<213> ORGANISM: Homo sapiens

<400> SEQUENCE: 33

Asp Asp Gly Tyr Tyr Gly Tyr Phe Asp Tyr
1               5                   10

<210> SEQ ID NO 34
<211> LENGTH: 114
<212> TYPE: PRT
<213> ORGANISM: Homo sapiens

<400> SEQUENCE: 34

Asp Val Val Met Thr Gln Thr Pro Leu Ser Leu Pro Val Ser Leu Gly
1               5                   10                  15

Asp Gln Ala Ser Ile Ser Cys Arg Ser Ser Gln Thr Leu Val His Ser
            20                  25                  30

Asp Gly Asn Thr Tyr Leu His Trp Tyr Leu Gln Lys Pro Gly Gln Ser
        35                  40                  45

Pro Lys Leu Leu Ile Tyr Lys Ile Ser Asn Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Leu Gly Val Tyr Phe Cys Ser Gln Ser
                85                  90                  95

Thr His Val Pro Pro Thr Phe Gly Gly Gly Thr Lys Leu Glu Ile Lys
            100                 105                 110

Arg Ala

<210> SEQ ID NO 35
<211> LENGTH: 16
<212> TYPE: PRT
<213> ORGANISM: Homo sapiens

<400> SEQUENCE: 35

Arg Ser Ser Gln Thr Leu Val His Ser Asp Gly Asn Thr Tyr Leu His
1               5                   10                  15

<210> SEQ ID NO 36
<211> LENGTH: 7
<212> TYPE: PRT
<213> ORGANISM: Homo sapiens

<400> SEQUENCE: 36

Lys Ile Ser Asn Arg Phe Ser
1               5

<210> SEQ ID NO 37
<211> LENGTH: 10
<212> TYPE: PRT
<213> ORGANISM: Homo sapiens
```

<400> SEQUENCE: 37

Ser Gln Ser Thr His Val Pro Pro Thr Phe
1               5                   10

<210> SEQ ID NO 38
<211> LENGTH: 118
<212> TYPE: PRT
<213> ORGANISM: Homo sapiens

<400> SEQUENCE: 38

Gln Val Gln Leu Gln Gln Pro Gly Ala Glu Leu Val Arg Pro Gly Ala
1               5                   10                  15

Ser Val Lys Met Ser Cys Lys Ala Ser Gly Tyr Thr Phe Ser Ser Tyr
                20                  25                  30

Leu Met Asp Trp Val Lys Gln Arg Pro Gly Gln Gly Phe Glu Cys Ile
            35                  40                  45

Gly Asn Ile Asn Pro Asn Thr Gly Ser Thr Ile Tyr Asn Glu Arg Phe
        50                  55                  60

Lys Gly Lys Ala Lys Leu Thr Val Asp Lys Ser Ser Ser Thr Ala Tyr
65                  70                  75                  80

Met Gln Leu Ile Ser Leu Thr Ser Glu Asp Ser Ala Val Tyr Tyr Cys
                85                  90                  95

Ala Ala Asp Gly Tyr Tyr Ala Pro Phe Thr Tyr Trp Gly Gln Gly Thr
                100                 105                 110

Leu Val Thr Val Ser Ala
            115

<210> SEQ ID NO 39
<211> LENGTH: 5
<212> TYPE: PRT
<213> ORGANISM: Homo sapiens

<400> SEQUENCE: 39

Ser Tyr Leu Met Asp
1               5

<210> SEQ ID NO 40
<211> LENGTH: 17
<212> TYPE: PRT
<213> ORGANISM: Homo sapiens

<400> SEQUENCE: 40

Asn Ile Asn Pro Asn Thr Gly Ser Thr Ile Tyr Asn Glu Arg Phe Lys
1               5                   10                  15

Gly

<210> SEQ ID NO 41
<211> LENGTH: 9
<212> TYPE: PRT
<213> ORGANISM: Homo sapiens

<400> SEQUENCE: 41

Asp Gly Tyr Tyr Ala Pro Phe Thr Tyr
1               5

<210> SEQ ID NO 42
<211> LENGTH: 114
<212> TYPE: PRT
<213> ORGANISM: Homo sapiens

<400> SEQUENCE: 42

```
Asp Ile Val Met Thr Gln Ala Ala Pro Ser Val Pro Val Thr Pro Gly
1               5                   10                  15

Glu Ser Val Ser Ile Ser Cys Arg Ser Ser Lys Ser Leu Leu His Asn
            20                  25                  30

Asn Gly Asn Thr Tyr Leu Tyr Trp Phe Leu Gln Arg Pro Gly Gln Ser
        35                  40                  45

Pro Gln Leu Leu Ile Tyr Arg Met Ser Asn Leu Ala Ser Gly Val Pro
    50                  55                  60

Asp Arg Phe Ser Gly Ser Gly Ser Gly Thr Ala Phe Thr Leu Arg Ile
65              70                  75                  80

Ser Arg Val Glu Ala Glu Asp Val Gly Val Tyr Tyr Cys Met Gln His
                85                  90                  95

Leu Glu Tyr Pro Phe Thr Phe Gly Ala Gly Thr Lys Leu Glu Leu Lys
            100                 105                 110

Arg Ala
```

<210> SEQ ID NO 43
<211> LENGTH: 16
<212> TYPE: PRT
<213> ORGANISM: Homo sapiens

<400> SEQUENCE: 43

```
Arg Ser Ser Lys Ser Leu Leu His Asn Asn Gly Asn Thr Tyr Leu Tyr
1               5                   10                  15
```

<210> SEQ ID NO 44
<211> LENGTH: 7
<212> TYPE: PRT
<213> ORGANISM: Homo sapiens

<400> SEQUENCE: 44

```
Arg Met Ser Asn Leu Ala Ser
1               5
```

<210> SEQ ID NO 45
<211> LENGTH: 10
<212> TYPE: PRT
<213> ORGANISM: Homo sapiens

<400> SEQUENCE: 45

```
Met Gln His Leu Glu Tyr Pro Phe Thr Phe
1               5                   10
```

<210> SEQ ID NO 46
<211> LENGTH: 123
<212> TYPE: PRT
<213> ORGANISM: Homo sapiens

<400> SEQUENCE: 46

```
Gln Val Gln Leu Gln Gln Ser Gly Pro Glu Leu Val Lys Pro Gly Ala
1               5                   10                  15

Ser Val Lys Ile Ser Cys Lys Ala Ser Gly Tyr Ser Phe Arg Ser Tyr
            20                  25                  30

Tyr Ile His Trp Met Lys Gln Ser Pro Gly Gln Gly Leu Glu Trp Ile
        35                  40                  45

Ala Trp Ile Tyr Pro Gly Gly Gly Lys Ile Tyr Tyr Asn Asp Asn Glu
    50                  55                  60

Lys Phe Lys Asp Lys Val Thr Leu Thr Ala Asp Thr Ser Ser Ser Thr
65              70                  75                  80
```

Ala Tyr Met Gln Leu Thr Gly Leu Thr Ser Glu Asp Ser Ala Val Tyr
                85                  90                  95

Phe Cys Ala Arg Trp Gly Gly Tyr Tyr Val Gly Ser Ile Leu Asp Tyr
            100                 105                 110

Trp Gly Gln Gly Thr Ser Val Thr Val Ser Ser
        115                 120

<210> SEQ ID NO 47
<211> LENGTH: 5
<212> TYPE: PRT
<213> ORGANISM: Homo sapiens

<400> SEQUENCE: 47

Ser Tyr Tyr Ile His
1               5

<210> SEQ ID NO 48
<211> LENGTH: 19
<212> TYPE: PRT
<213> ORGANISM: Homo sapiens

<400> SEQUENCE: 48

Trp Ile Tyr Pro Gly Gly Gly Lys Ile Tyr Tyr Asn Asp Asn Glu Lys
1               5                   10                  15

Phe Lys Asp

<210> SEQ ID NO 49
<211> LENGTH: 12
<212> TYPE: PRT
<213> ORGANISM: Homo sapiens

<400> SEQUENCE: 49

Trp Gly Gly Tyr Tyr Val Gly Ser Ile Leu Asp Tyr
1               5                   10

<210> SEQ ID NO 50
<211> LENGTH: 111
<212> TYPE: PRT
<213> ORGANISM: Homo sapiens

<400> SEQUENCE: 50

Asp Gly Asp Ile Val Met Thr Gln Ser Gln Lys Phe Leu Ser Thr Ser
1               5                   10                  15

Val Gly Asp Arg Val Ser Val Thr Cys Lys Ala Ser Gln Asn Val Asp
            20                  25                  30

Asn Asn Val Ala Trp Tyr Gln Gln Arg Pro Gly Gln Ser Pro Lys Pro
        35                  40                  45

Leu Ile Tyr Leu Thr Ser Ser Arg Tyr Ser Gly Val Pro Asp Arg Phe
    50                  55                  60

Thr Gly Ser Gly Ser Gly Thr Asp Phe Thr Leu Thr Ile Thr Asn Val
65                  70                  75                  80

Gln Ser Glu Asp Leu Ala Glu Tyr Phe Cys Gln Gln Tyr Lys Thr Tyr
                85                  90                  95

Pro Leu Thr Phe Ser Val Gly Thr Lys Leu Glu Leu Lys Arg Ala
            100                 105                 110

<210> SEQ ID NO 51
<211> LENGTH: 11
<212> TYPE: PRT
<213> ORGANISM: Homo sapiens

<400> SEQUENCE: 51

```
<210> SEQ ID NO 52
<211> LENGTH: 7
<212> TYPE: PRT
<213> ORGANISM: Homo sapiens

<400> SEQUENCE: 52

Lys Ala Ser Gln Asn Val Asp Asn Val Ala
1               5                   10

<210> SEQ ID NO 52
<211> LENGTH: 7
<212> TYPE: PRT
<213> ORGANISM: Homo sapiens

<400> SEQUENCE: 52

Leu Thr Ser Ser Arg Tyr Ser
1               5

<210> SEQ ID NO 53
<211> LENGTH: 12
<212> TYPE: PRT
<213> ORGANISM: Homo sapiens

<400> SEQUENCE: 53

Gln Gln Tyr Lys Thr Tyr Pro Leu Thr Phe Ser Val
1               5                   10
```

TEST AGENT FOR VISCERAL OBESITY AND USE THEREOF

CROSS-REFERENCE TO RELATED APPLICATIONS

This application is a national stage entry under 35 U.S.C. §371 of International Application No. PCT/JP2010/058097, filed May 13, 2010, which claims priority to Japanese Patent Application No. 2009-116323, filed May 13, 2009.

TECHNICAL FIELD

The present invention relates to visceral obesity test drugs useful for the diagnosis of visceral obesity. More specifically, the present invention relates to test drugs useful as a tool for determining visceral obesity in a subject and detecting visceral obesity individuals, and to methods for detecting (diagnosing) visceral obesity with the test drugs. The present invention also concerns pharmaceutical compositions for ameliorating visceral obesity, or for preventing metabolic disease or cardiovascular disease such as metabolic syndrome that develops from visceral obesity, and methods (screening methods) for searching for an active ingredient of such pharmaceutical compositions.

Further, the present invention relates to pharmaceutical compositions effective for ameliorating diabetes by suppressing hepatic glucose output, and for preventing diabetes complications such as diabetic neuropathy that develop from diabetes, and to methods (screening methods) for searching for an active ingredient of such pharmaceutical compositions.

BACKGROUND ART

The increasing incidence of metabolic syndrome (hereinafter, also referred to simply as "MS") arising from visceral obesity has become a social issue. MS refers to conditions were visceral obesity occurs in an individual with accumulations of other conditions such as impaired glucose tolerance, hyperlipidemia, and high-blood pressure, though the symptoms may be minor. The importance of MS has thus been recognized as the background of arteriosclerotic disease onset. According to the increasingly and internationally accepted MS diagnosis criteria introduced by the US National Cholesterol Education Program (NCEP), Adult Treatment Panel III (ATP III), MS is determined when at least three of the following criteria are met: (1) visceral fat diagnosed from a circumference at navel, (2) hypertriglyceridemia, (3) low HDL cholesteremia, (4) high-blood pressure, and (5) impaired glucose tolerance (NPL 1). MS diagnosis for Japanese is based on the criteria published by The Japanese Society of Internal Medicine in 2005. These criteria include visceral obesity as the essential item, and MS is determined when two or more of the following are met: high-blood pressure, abnormal lipid metabolism (hypertriglyceridemia and/or low HDL-cholesteremia), and fasting hyperglycemia (NPL 2).

The proposed criteria for determining visceral obesity as the essential conditions for MS include (a) a visceral fat area of 100 $cm^2$ or more in computed tomography (CT), and (b) an abdominal circumference of 85 cm or more for men, and 90 cm or more for women in abdominal circumference measurement (NPL 3). CT measurement of visceral fat area can only be carried out in limited facilities, and involves cost and exposure problems. For these reasons, many facilities adopt abdominal circumference measurement for the determination of visceral obesity.

However, while the abdominal circumference measurement is simple, it is not necessarily sufficient in terms of measurement error and accuracy (NPL 4, 5), and development of newer diagnosis criteria is waited.

There are many reports concerning the involvement of genetic factors in MS (for example, NPL 6, 7, and PTL 1 to 4). NPL 6 introduces chromosomal sites related to MS. Further, PTL 1 describes a method for detecting specific polymorphism in Klotho gene as a method of determining the possibility of developing MS. PTL 2 describes a method for detecting specific polymorphism in angiopoietin-1 gene. PTL 3 describes a method for detecting specific polymorphism in McKusick-Kaufman syndrome gene. PTL 4 describes a method for detecting specific polymorphism in myosin IXA (AY09A) gene. However, a link to coiled-coil domain containing protein 3 (hereinafter, "CCDC3") gene is not known.

PTL 5 reports FARS1 gene having the same sequence as the CCDC3 gene. It is also reported that increased diet in mice increases the body weight and FARS1 mRNA levels.

The anatomical location of the liver makes the liver the first target organ of the insulin secreted by the pancreas, and an organ that first uses the sugar that has entered the portal vein after absorption in the digestive tract. The liver also has contradictory functions synthesizing glycogen through the uptake of sugar during ingestion, and, on the other hand, producing and releasing sugar through glycogen decomposition and gluconeogenesis during a period of fasting. These functions are regulated in an effort to maintain the homeostasis in sugar metabolism. It is known that the sugar production in liver is modulated through activation of the insulin-induced glycogen synthesis in the hyperglycemia state, and through activation of glycogen decomposition and gluconeogenesis by the effects of substances such as glucagon, catecholamine, and cortisol in the hypoglycemic state.

While the sugar production and release in liver are regulated in this manner, there have been reports that liver glucose release amounts increase in cases of diabetes, an abnormal sugar metabolism disease. Specifically, an about 2-fold increase is confirmed in gluconeogenesis and liver glucose release amount in the diabetes model animal db/db mice (NPL 8), and an about 1.9-fold increase in liver glucose release amount is confirmed in human diabetes patients. It has been revealed that while 70% of liver glucose release amount originates in glycogen decomposition and 30% in gluconeogenesis in healthy individuals, 56% of the liver glucose release amount originates in gluconeogenesis in diabetes patients. These represent a strong indication that the increased liver glucose release amounts due to the acceleration of the gluconeogenesis system are involved in the hyperglycemia state of diabetes (NPL 9). Taken together, regulation of liver glucose release amount can be an important factor in considering diabetes therapy.

CITATION LIST

Patent Literature

PTL 1: JP-T-2003-514513
PTL 2: JP-A-2007-54002
PTL 3: JP-A-2009-27985
PTL 4: JP-A-2009-27986
PTL 5: Published US Patent Application, No. 20030113889

Non-Patent Literature

NPL 1: Expert Panel on Detection, Evaluation, and Treatment of High Blood Cholesterol in Adults: Executive Summary of The Third Report of The National Cholesterol Education Program (NCEP) Expert Panel on Detection, Evaluation, and Treatment of High Blood Cholesterol in Adults (Adult Treatment Panel III). JAMA 285: 2486-2497, 2001.

NPL 2: Metabolic Syndrome Diagnose Criteria Exploratory Committee: Definition and Diagnose Criteria of Metabolic Syndrome, The Japanese Society of Internal Medicine 94: 794-809, 2005

NPL 3: The Examination Committee of Criteria for 'Obesity Disease' in Japan, Japan Society for the Study of Obesity: New criteria for 'obesity disease' in Japan. Circ J 66: 987-992, 2002.

NPL 4: S Yamada, Y Tsukamoto, J Irie: Waist circumference in metabolic syndrome. Lancet 370: 1541-42, 2007.

NPL 5: S Yamamoto, T Nakagawa, S Kusano, M Takamura, K Hattori, M Irokawa: Development of the Automated Diagnosis System CT Screening for Visceral Obesity MEDIX 41: 15-20, 2004

NPL 6: Nat Clin Pract Cardiovasc Med 3:482-489 (2006)

NPL 7: Obesity Research 13:381-490 (2005)

NPL 8: Aoki et al: Dehydroepiandrosterone decreases elevated hepatic glucose production in C57BL/KsJ-db/db mice. Life Sciences 74: 3075-3084, 2004

NPL 9: Consoli et al: Predominant Role of Gluconeogenesis in Increased Hepatic Glucose Production in NIDDM. Diabetes 38: 550-557, 1989

SUMMARY OF INVENTION

Technical Problem

As described above, there are implications that visceral obesity represents a pathological component underlying the metabolic syndrome (MS) that increases the chance of the onset of cardiovascular diseases such as myocardial infarction. Accordingly, there is a strong need for appropriately diagnosing visceral obesity for early amelioration, and for preventing the onset of MS, and, in turn, cardiovascular disease. Conventional diagnoses for visceral obesity are either complicated or inaccurate, and a detection marker that can accurately and conveniently determine visceral obesity is needed. There is also a need for a pharmaceutical composition effective at ameliorating visceral obesity, and for a pharmaceutical composition that effectively ameliorates diabetes caused by visceral obesity and prevents diabetes complications.

In view of these problems, it is an object of the present invention to provide a visceral obesity test drug that can accurately determine visceral obesity by specifically reflecting the disease. Another object is to provide a visceral obesity detection method that uses the test drug.

Yet another object of the present invention is to provide a pharmaceutical composition effectively at ameliorating visceral obesity or diabetes, and preventing the onset of MS and cardiovascular disease, or preventing diabetes complications. It is still another object of the present invention to provide a method (screening method) for searching for a substance that can be used as an active ingredient of the pharmaceutical composition.

Solution to Problem

The present inventors conducted intensive studies to achieve the foregoing objects, and found a gene (coiled-coil domain containing protein 3 (CCDC3) gene) that resides in the visceral adipose tissue of visceral obesity individuals and shows high expression specific to visceral obesity individuals. It was also found that the gene, while having increased expression specific to the visceral fat of visceral obesity individuals, did not show high expression in subcutaneous fat. It was confirmed that the gene was a gene (visceral obesity-related gene) closely associated with visceral obesity. The protein encoded by the gene had increased expression specific to the visceral adipose cells in visceral obesity, and was identified as a secretory protein secreted outside of the cells. It was thus confirmed that the CCDC3 gene and the product protein (hereinafter, referred to as "CCDC3 protein" to distinguish from the gene) were useful as detection markers for detecting visceral obesity. The CCDC3 protein was found to be particularly useful as a detection marker for a blood test sample.

The present inventors also found that CCDC3 protein stimulations increase glucose output from liver cells, and that CCDC3 protein stimulations significantly increase the mRNA expression amounts of the gluconeogenesis rate-limiting enzymes glucose-6-phosphatase (hereinafter, "G6 Pase") and phosphoenolpyruvate carboxykinase (hereinafter, "PEPCK"). It was thus confirmed that the CCDC3 protein has a glucose output promoting effect in liver. Further, the present inventors found that the body weight and glucose level of a transgenic mouse designed to overexpress CCDC3 gene increase by overexpression of CCDC3 mRNA. This suggest that the CCDC3 (hereinafter, collectively refers to "CCDC3 gene" and "CCDC3 protein") is strongly involved in visceral obesity and in metabolic syndrome (MS) caused by visceral obesity, particularly in the onset of diabetes and diabetes complications.

These findings assured that the CCDC3 gene was a visceral obesity-related gene deeply involved in visceral obesity and the resulting MS and cardiovascular disease, and that the CCDC3 gene could be used as a target gene useful for the development of a method for ameliorating visceral obesity or preventing MS and cardiovascular disease. It was therefore considered that a substance with the effect to suppress CCDC3 gene expression or CCDC3 protein function (activity) could be used as an active ingredient for ameliorating visceral obesity or preventing MS and cardiovascular disease, or as an active ingredient for ameliorating diabetes or preventing diabetes complications resulting from the progression of the disease. Further, it was assured that a screening system using these as an index would provide a new mechanism for the effective development of a pharmaceutical composition effective for ameliorating visceral obesity or preventing metabolic disease and cardiovascular disease such as MS, or a pharmaceutical composition effective for ameliorating diabetes or preventing diabetes complications.

The present invention has been completed based on these findings, and includes the following specific aspects.

(I) Visceral Obesity Test Drug and Use Thereof (I-1)(1) A visceral obesity test drug, comprising:

(1) a polynucleotide with at least 15 contiguous bases of a base sequence of CCDC3 gene, and/or a polynucleotide complementary to the polynucleotide; or (2) a polynucleotide of at least 15 bases that hybridizes under stringent conditions with the CCDC3 gene base sequence or with a base sequence complementary to the CCDC3 gene base sequence.

(I-2) A visceral obesity test drug that includes an antibody that recognizes CCDC3 protein.

(I-3) A visceral obesity test drug of (1-2) in which the antibody that recognizes CCDC3 protein is any one of the following antibodies (i) to (vi):

(i) an antibody having amino acid sequences of SEQ ID NOS:31, 32, and 33 for the CDR1, CDR2, and CDR3, respectively, of the heavy-chain variable domain, and amino acid sequences of SEQ ID NOS:35, 36, and 37 for the CDR1, CDR2, and CDR3, respectively, of the light-chain variable domain;

(ii) an antibody having amino acid sequences of SEQ ID NOS:39, 40, and 41 for the CDR1, CDR2, and CDR3, respectively, of the heavy-chain variable domain, and amino acid sequences of SEQ ID NOS:43, 44, and 45 for the CDR1, CDR2, and CDR3, respectively, of the light-chain variable domain;

(iii) an antibody having amino acid sequences of SEQ ID NOS:47, 48, and 49' for the CDR1, CDR2, and CDR3, respectively, of the heavy-chain variable domain, and amino acid sequences of SEQ ID NOS:51, 52, and 53 for the CDR1, CDR2, and CDR3, respectively, of the light-chain variable domain;

(iv) an antibody of (i) having an amino acid sequence of SEQ ID NO:30 for the heavy-chain variable domain, and an amino acid sequence of SEQ ID NO:34 for the light-chain variable domain;

(v) an antibody of (ii) having an amino acid sequence of SEQ ID NO:38 for the heavy-chain variable domain, and an amino acid sequence of SEQ ID NO:42 for the light-chain variable domain; and (vi) an antibody of (iii) having an amino acid sequence of SEQ ID NO:46 for the heavy-chain variable domain, and an amino acid sequence of SEQ ID NO:50 for the light-chain variable domain.

(II) Visceral Obesity Detection Method (II-1) A visceral obesity detection method that uses as an index the CCDC3 mRNA expression amount or the amount of the product CCDC3 protein in a test sample collected from a subject.

(II-2)(1) A visceral obesity detection method according to (II-1), comprising the steps of:

(1) measuring the amount of CCDC3 mRNA expression or the amount of the product CCDC3 protein in the test sample collected from the subject;

(2) comparing the measured CCDC3 mRNA expression amount (subject expression amount) or the measured amount of the product CCDC3 protein (subject production amount) with the CCDC3 mRNA expression amount (control expression amount) or the amount of the product CCDC3 protein (control production amount) in a control sample collected from a non-visceral obesity individual; and (3) determining visceral obesity in the subject by using a higher subject expression amount or a higher subject production amount than the control expression amount or the control production amount as an index.

(II-3) A visceral obesity detection method according to (II-1) or (II-2), wherein the CCDC3 mRNA expression amount is measured by using the test drug of (I-1).

(II-4) A visceral obesity detection method according to (II-1) or (II-2), wherein the CCDC3 production amount (subject production amount) is measured by using the test drug of (1-2) or (1-3).

(III) Visceral Obesity Ameliorating Agent or Preventing Agent for Diseases that Develop from Visceral Obesity (III-1) A visceral obesity ameliorating agent or a preventing agent for diseases that develop from visceral obesity (hereinafter, collectively referred to as "anti-visceral obesity agent") that includes as an active ingredient a nucleic acid that suppresses CCDC3 gene expression or CCDC3 protein function, or a neutralizing antibody against the CCDC3 protein.

(III-2) An anti-visceral obesity agent according to (III-1), wherein the nucleic acid that suppresses CCDC3 gene expression or CCDC3 protein function is a siRNA that specifically suppresses CCDC3 gene expression.

(III-3) A nucleic acid that suppresses CDC3 gene expression or CCDC3 protein function, or a neutralizing antibody against the CCDC3 protein, for use in ameliorating visceral obesity or preventing diseases that develop from visceral obesity.

(III-4) A nucleic acid that suppresses CCDC3 gene expression or CCDC3 protein function according to (III-3), wherein the nucleic acid is a siRNA that specifically suppresses CCDC3 gene expression.

(III-5) A method for ameliorating visceral obesity or preventing diseases that develop from visceral obesity, the method comprising the step of administering to a visceral obesity individual a nucleic acid that suppresses CDC3 gene expression or CCDC3 protein function, or a neutralizing antibody against the CCDC3 protein.

(III-6) A method according to (III-5), wherein the nucleic acid that suppresses CCDC3 gene expression or CCDC3 protein function is a siRNA that specifically suppresses CCDC3 gene expression.

(IV) Diabetes Therapeutic Agent or Diabetes Complication Preventing Agent (IV-1) A diabetes therapeutic agent or a diabetes complication preventing agent (hereinafter, collectively referred to as "antidiabetic agent") that includes as an active ingredient a nucleic acid that suppresses CCDC3 gene expression or CCDC3 protein function, or a neutralizing antibody against the CCDC3 protein.

(IV-2) An antidiabetic agent according, to (IV-1) wherein the nucleic acid that suppresses CCDC3 gene expression or CCDC3 protein function is a siRNA that specifically suppresses CCDC3 gene expression.

(IV-3) A nucleic acid that suppresses CDC3 gene expression or CCDC3 protein function, or a neutralizing antibody against the CCDC3 protein, for use in treating diabetes or preventing diabetes complications.

(IV-4) A nucleic acid that suppresses CCDC3 gene expression or CCDC3 protein function according to (IV-3), wherein the nucleic acid is a siRNA that specifically suppresses CCDC3 gene expression.

(IV-5) A method for treating diabetes or preventing diabetes complications, comprising the step of administering to a diabetes patient a nucleic acid that suppresses CDC3 gene expression or CCDC3 protein function, or a neutralizing antibody against the CCDC3 protein.

(IV-6) A method according to (IV-5), wherein the nucleic acid that suppresses CCDC3 gene expression or CCDC3 protein function is a siRNA that specifically suppresses CCDC3 gene expression.

(V) Method for Screening for a Component Effective for Preventing or Treating Visceral Obesity and Diabetes (V-1) A screening method for a substance that suppresses CCDC3 gene expression or CCDC3 protein production, the method comprising the steps of:

(1) contacting a test substance to a CCDC3 gene expressible cell or to a cell capable of producing CCDC3 protein;

(2) measuring the CCDC3 gene expression amount or the amount of the product CCDC3 protein in the cell contacted to the test substance; and (3) selecting a test substance that makes the measured CCDC3 gene expression amount or the measured amount of the product CCDC3 protein smaller than, in a control cell not brought into contact with the test substance.

(V-2) A screening method according to (V-1), wherein the CCDC3 gene expressible cell or the cell capable of producing CCDC3 protein is a visceral adipose cell.

(V-3) A method for screening a substance that suppresses CCDC3 protein function or activity, the method comprising the steps of:
  (1') contacting a test substance, a cell that reacts with CCDC3 protein, and CCDC3 protein;
  (2') detecting the CCDC3 protein function or activity in the cell contacted to the test substance; and
  (3') selecting a test substance that makes the measured CCDC3 protein function or activity lower than the CCDC3 protein function or activity in a control cell contacted to the CCDC3 protein but not to the test substance.
(V-4) A screening method according to (V-3), wherein the cell that reacts with CCDC3 protein is a liver-derived cell.
(V-5) A screening method according to (V-3) or (V-4), wherein the CCDC3 protein function or activity is a glucose output promoting effect.
(V-6) A screening method according to (V-3) or (V-4), wherein the CCDC3 protein function or activity is an effect of increasing the mRNA level of a gluconeogenesis rate-limiting enzyme gene.
(V-7) A screening method according to any one of (V-1) to (V-6), wherein the method searches for an active ingredient for ameliorating visceral obesity or preventing diseases that develop from visceral obesity.
(V-8) A screening method according to any one of (V-1) to (V-6), wherein the method searches for an active ingredient for ameliorating diabetes or preventing diabetes complications.
(V-9) A method for screening an active ingredient for ameliorating visceral obesity or for preventing diseases that develop from visceral obesity, or an active ingredient for ameliorating diabetes or preventing diabetes complications, the method comprising the steps of:
  (a) administering a test substance to a CCDC3 transgenic mouse overexpressing CCDC3 gene;
  (b) measuring the body weight (subject weight) or glucose level (subject glucose level) of the test substance-administered CCDC3 transgenic mouse over a time course, and comparing the measured body weight or glucose level with the body weight (control body weight) or glucose level (control glucose level) measured over a time course for a CCDC3 transgenic mouse not administered With the test substance; and
  (c) selecting a test substance that makes the subject weight or subject glucose level lower, than the control body weight or control glucose level, the test substance being selected as an active ingredient that ameliorates visceral obesity or diabetes.
(VI) Antibody that Recognizes CCDC3 Protein
(VI-1) An antibody that recognizes CCDC3 protein, and is selected from the group of the following antibodies (i) to (iii):
  (i) an antibody having amino acid sequences of SEQ ID NOS:31, 32, and 33 for the CDR1, CDR2, and CDR3, respectively, of the heavy-chain variable domain, and amino acid sequences of SEQ ID NOS:35, 36, and 37 for the CDR1, CDR2, and CDR3, respectively, of the light-chain variable domain;
  (ii) an antibody having amino acid sequences of SEQ ID NOS:39, 40, and 41 for the CDR1, CDR2, and CDR3, respectively, of the heavy-chain variable domain, and amino acid sequences of SEQ ID NOS:43, 44, and 45 for the CDR1, CDR2, and CDR3, respectively, of the light-chain variable domain; and
  (iii) an antibody having amino acid sequences of SEQ ID NOS:47, 48, and 49 for the CDR1, CDR2, and CDR3, respectively, of the heavy-chain variable domain, and amino acid sequences of SEQ ID NOS:51, 52, and 53 for the CDR1, CDR2, and CDR3, respectively, of the light-chain variable domain.
(VI-2) An antibody according to (VI-1), wherein the antibody is an antibody selected from the group of the following antibodies (iv) to (vi):
  (iv) an antibody having an amino acid sequence of SEQ ID NO:30 for the heavy-chain variable domain, and an amino acid sequence of SEQ ID NO:34 for the light-chain variable domain;
  (v) an antibody having an amino acid sequence of SEQ ID NO:38 for the heavy-chain variable domain, and an amino acid sequence of SEQ ID NO:42 for the light-chain variable domain; and
  (vi) an antibody having an amino acid sequence of SEQ ID NO:46 for the heavy-chain variable domain, and an amino acid sequence of SEQ ID NO:50 for the light-chain variable domain.
(VI-3) An antibody that binds to an epitope bound to the antibody of (VI-1) or (VI-2).

Advantageous Effects of Invention

The test drug and test method provided by the present invention enable accurate detection of visceral obesity in a subject by in vitro testing, without using conventional, complicated and inaccurate measurement methods such as visceral fat area measurement using computed tomography, and abdominal circumference measurement. Further, by using the test drug and detection method of the present invention, visceral obesity can easily be detected in a subject in vitro, without having the need to have the expert knowledge of physicians or other specialists.

The subject having visceral obesity (visceral obesity patient) found by the method of the present invention is given the chance to take appropriate measures to ameliorate and eliminate the visceral obesity by being informed of the disease. The present invention is therefore very useful as a test method for ameliorating visceral obesity at early stages, and for preventing the progression of visceral obesity into metabolic disease and cardiovascular disease such as metabolic syndrome (MS).

Further, the anti-visceral obesity agent provided by the present invention can be effectively used as a pharmaceutical composition effective for ameliorating visceral obesity, and thus preventing the progression of visceral obesity into metabolic disease and cardiovascular disease such as MS. Further, the antidiabetic agent provided by the present invention can be effectively used as a pharmaceutical composition effective for suppressing glucose release in liver and ameliorating the hyperglycemia state, and thus preventing progression into diabetes, and preventing diabetes complications.

Further, the screening method of the present invention makes it possible to obtain a component effective for ameliorating visceral obesity, and preventing the progression of the disease into metabolic disease and cardiovascular disease such as MS, or a component effective for ameliorating the hyperglycemia state, and preventing diabetes and diabetes complications caused by the progression of diabetes. Specifically, the method can be effectively used for the development of a novel medicinal agent effective for ameliorating visceral obesity and preventing metabolic disease and cardiovascular disease, and a novel medicinal agent effective for ameliorating diabetes and preventing diabetes complications.

DESCRIPTION OF EMBODIMENTS

Figure 1:
FIG. 1 represents the result of the comparison of CCDC3 gene (mRNA) expression amount between the visceral adipose tissue and subcutaneous adipose tissue of non-visceral obesity individuals (5 cases) and visceral obesity individuals (5 cases). The CCDC3 gene expression amount in the visceral obesity individuals is presented as the relative ratio with respect to the expression amount 1 of the non-visceral obesity individuals. The CCDC3 gene expression amount in the visceral fat of the visceral obesity individuals had a 3.2-fold increase over the expression amount in the visceral adipose tissue of the non-visceral obesity individuals (Example 1).

1. Definitions of the Terms Used in the Present Invention

The abbreviations representing the base sequences (nucleotide sequences), nucleic acids, and other elements used herein follow the rules of IUPAC-IUB [IUPAc-IUB communication on Biological Nomenclature, Eur. J. Biochem., 138; 9 (1984)], *The Guideline for Preparation of Minute Descriptions of Compounds Including Base Sequence or Amino Acid Sequence* (Japan Patent Office), and the conventional notation used in the art.

As used herein, "CCDC3 gene" encompasses not only human-derived CCDC3 gene represented by SEQ ID NO:1, but genes, including ortholog genes conserved among different biological species such as humans, mice, and rats, that encode proteins (for example, homologs (including splice variants), mutants, and derivatives) having biologically equivalent functions as the human-derived protein (CCDC3 protein). For example, the genes that encode the homologs of the human-derived CCDC3 protein may be the genes of other biological species such as mice and rats, corresponding to the human CCDC3 gene that encodes the CCDC3 protein. These genes (homologs) can be identified from HomoloGene (http://www.ncbi.nlm.nih.gov/HomoloGene/). Specifically, human gene data are found by searching specific human gene names (CCDC3 gene) or base sequence accession numbers (GenBank Accession No. NM_031455) in LocusLink (http://www.ncbi.nlm.nih.gov/LocusLink/). The genes of other biological species such as mice and rats, corresponding to the human CCDC3 gene can then be selected as the genes (homologs) of interest from a list of the gene homolog correlation between other biological species and human genes displayed by accessing the HomoloGene in the data link menu. A specific example of a mouse homolog of human CCDC3 gene (GenBank Accession No. NM_031455; SEQ ID NO:1) is the mouse CCDC3 gene (GenBank Accession No. NM_028804) represented by SEQ ID NO:2.

Further, the "gene" as used herein does not distinguish between regulatory region, coding region, exon, and intron, unless otherwise stated.

As used herein, "DNA" encompasses double-stranded DNAs including human genomic DNA, single-stranded DNAs (sense strands) including cDNA and synthetic DNA, single-stranded DNAs (antisense strands) having complementary sequences to the sense strands, and fragments thereof, unless otherwise stated. As used herein, "RNA" is intended to include not only single-stranded RNAs, but single-stranded RNAs having complementary sequences, and double-stranded RNAs formed from such RNAs, unless otherwise stated. The RNA includes synthetic RNAs such as total RNA, mRNA, rRNA, and siRNA.

Further, as used herein "nucleotide", "oligonucleotide", and "polynucleotide" have the same meaning as the nucleic acid, and include both DNA and RNA. These may be double-stranded or single-stranded. By "nucleotide (or oligonucleotide, polynucleotide) of a certain sequence", it inclusively means a nucleotide (or oligonucleotide, polynucleotide) having a complementary sequence, unless otherwise stated. Further, when the "nucleotide" (or "oligonucleotide", "polynucleotide") is an RNA, the letter "T" in the bases of the Sequence Listing should be read as "U".

As used herein, "CCDC3 protein" encompasses not only human-derived CCDC3 protein represented by SEQ ID NO:3, but proteins translated from the ortholog genes conserved among different biological species such as humans, mice, and rats, and homologs (including splice variants), mutants, derivatives, and amino acid-modified products, provided that such equivalents have the same biological functions as such proteins. Examples of such homologs include proteins of other biological species such as mice and rats, corresponding to the human CCDC3 protein (SEQ ID NO:3), and these can be deductively identified from the base sequences of the genes identified in HomoloGene (http://www.ncbi.nlm.nih.gov/HomoloGene/). The mutants may be naturally occurring allele mutants, not naturally occurring mutants, and mutants having amino acid sequences artificially modified through deletion, substitution, addition, and insertion. Note that the mutants may have at least 70%, preferably 80% or more, more preferably 85% or more, further preferably 90% or more, even more preferably 95% or more, particularly preferably 97% or more amino acid sequence identify with unmutated proteins. An example of a mouse homolog of the human CCDC3 protein is the mouse CCDC3 protein represented by SEQ ID NO:4. Note that the term "CCDC3" is also used to collectively refer to the CCDC3 gene and the CCDC3 protein, without distinguishing the two.

As used herein, the nucleic acid that suppresses CCDC3 gene expression means a nucleic acid that has the effect to suppress mRNA expression from the CCDC3 gene or suppress translation of CCDC3 mRNA into CCDC3 protein, and encompasses not only siRNAs for the CCDC3 gene, but miRNAs, antisense poly(oligo)nucleotides, ribozymes, and decoys.

Further, as used herein, the nucleic acid that suppresses the function of the CCDC3 protein means a nucleic acid that has the effect to suppress the function of CCDC3 protein, and encompasses aptamers for CCDC3 protein.

As used herein, "antibody" encompasses polyclonal antibodies, monoclonal antibodies, chimeric antibodies, single-stranded antibodies, including antigen binding parts such as Fab fragments, and fragments created from a Fab expression library.

Obesity has two types: visceral obesity that involves fat accumulation in the gut and the surrounding area, and subcutaneous obesity that involves more subcutaneous fat and less visceral fat. As used herein, "visceral obesity" refers to the former, a type of obesity characterized by accumulation of large fat in the gut and the surrounding area. The diagnosis criteria for visceral obesity involve a visceral fat area of 100 $cm^2$ or more at the navel height in a CT measurement.

As used herein, "metabolic syndrome (MS)" refers to conditions such as high-blood pressure, abnormal sugar metabolism, and abnormal lipid metabolism, stemming from visceral obesity. Conventionally, metabolic syndrome is diagnosed when a person with an abdominal circumference (waist circumference) of 85 cm or more for men and 90 cm or more for women (equivalent of a visceral fat area of 100 $cm^2$ or more) satisfies two or more of the following: (1) abnormal serum lipid level (triglyceride value of 150 mg/dL or more, or an HDL cholesterol value of less than 40 mg/dL), (2) high blood pressure (maximum blood pressure of 130 mmHg or more, or minimum blood pressure of 85 mmHg or more), and (3) hyperglycemia (fasting glucose level of 110 mg/dL).

As used herein, "cardiovascular disease" means conditions that involve a disturbed blood flow in the heart due to cardiovascular abnormalities, lowered heart functions, and lesions. Specific examples include diseases such as angina, myocardial infarction, and heart failure. Further, as used herein, "metabolic disease" means disorders caused by the excess or deficient accumulation of metabolites in blood or in specific organs as a result of failures, innate or acquired, in various stages of the metabolic pathway. Aside from MS, other specific examples include diseases such as hyperlipidemia, diabetes, and obesity.

As used herein, "diabetes complication" means diseases and symptoms that develop from the diabetes itself. Specific examples include diseases such as diabetic retinopathy, diabetic nephropathy, and diabetic neuropathy.

Further, as used herein, "test drug" means agents directly or indirectly used to determine the presence or absence of visceral obesity, or to diagnose the extent of visceral obesity, and agents directly or indirectly used for the screening of a candidate substance effective for ameliorating visceral obesity or preventing the progress of visceral obesity. In relation to visceral obesity, the test drug encompasses (poly)(oligo) nucleotides and antibodies that can specifically recognize and bind to the CCDC3 gene that has increased expression in an organism, particularly in the visceral adipose tissue, or to the expression product (CCDC3 protein). The (poly)(oligo) nucleotides and antibodies of these properties can be effectively used as probes for detecting the CCDC3 gene and CCDC3 protein, either in vivo or in vitro, expressed in the tissues and cells of an organism. The (poly)(oligo)nucleotides also can be effectively used as primers for amplifying the gene expressed in the organism.

As used herein, the "organism tissue" and "organism sample" under diagnosis encompass tissues that show increased expression of the CCDC3 gene (mRNA) of the present invention in visceral obesity, and tissues (including blood) in which the gene expression product (CCDC3 protein) is produced or secreted. Preferred examples include visceral adipose tissue and blood.

The following describes specific uses of the CCDC3 gene (polynucleotide), the expression product (CCDC3 protein), and their derivatives.

2. Visceral Obesity Test Drug

The present invention provides a test drug suitably used for detecting visceral obesity in a subject. The test drug is also used in a screening method (described later) for searching for an active ingredient (candidate substance) of an ameliorating agent for visceral obesity, or of a preventing agent for metabolic disease and cardiovascular disease such as MS. The test drug also has use in searching for an active ingredient (candidate substance) of a diabetes ameliorating agent, or of a preparation for preventing diabetes progression and diabetes complications.

(1) Poly(or Oligo)Nucleotide

In the present invention, the detection (diagnosis) of visceral obesity, is performed by evaluating the presence or absence of an increase in CCDC3 gene (mRNA) expression, or the expression level (expression amount) of CCDC3 gene (mRNA) in the tissues, particularly the visceral adipose tissue, of a subject organism. Here, the test drug of the present invention can be used as a primer that recognizes and amplifies the RNA produced by the expression of the gene, or the polynucleotide derived from the RNA. The test drug also can be used as a probe for specifically detecting the RNA, or the polynucleotide derived from the RNA.

The test drug of the present invention may be a polynucleotide with the base sequence (full-length sequence) of the CCDC3 gene, or a polynucleotide having a complementary sequence thereof, provided that it selectively (specifically) recognizes CCDC3 gene or a polynucleotide derived from the gene. Further, the test drug may be a polynucleotide with a partial sequence of the full-length sequence, or a polynucleotide with a partial sequence of the complementary sequence. In this case, the partial sequence may be a polynucleotide with a length of at least 15 contiguous bases arbitrarily selected from the base sequence of the full-length sequence or of the complementary sequence.

Note that the phrase "selectively (specifically) recognize" means, for example, specifically detecting CCDC3 gene or a polynucleotide derived from CCDC3 gene in northern blotting, or specifically producing CCDC3 gene or a polynucleotide derived from CCDC3 gene in a RT-PCR method. However, the meaning of the phrase is not limited to this, as long as the detected product or the product obtained can be determined as being derived from CCDC3 gene by a skilled artisan.

Specifically, the test drug of the present invention includes a polynucleotide having at least 15 contiguous bases, and/or a polynucleotide complementary thereto, in the base sequence of CCDC3 gene. As used herein, "complementary polynucleotide (complementary strand, opposite strand)" means a polynucleotide with the base complementarity, based on base pairing such as A:T and G:C, to the full-length sequence of the polynucleotide with the CCDC3 gene base sequence, or to the partial sequence having a base sequence with a length of at least 15 contiguous bases of the base sequence (the full-length sequence and the partial sequences will be referred to as "plus strands" for convenience). It should be noted that the complementary strand is not limited to forming a completely complementary sequence to the base sequence of the plus strand of interest, and may have complementarity sufficient to hybridize with the plus strand of interest under stringent conditions. Note that stringent conditions may be decided based on the melting temperature (Tm) of the conjugate or the nucleic acid bound to a probe, as taught by Berger and Kimmel (1987, Guide to Molecular Cloning Techniques Methods in Enzymology, Vol. 152, Academic Press, San Diego Calif.). For example, typical post-hybridization washing conditions may involve roughly 1×SSC, 0.1% SDS, and 37° C. Preferably, the complementary strand remains hybridized with the target plus strand even after washing under these conditions. More severe hybridization conditions may involve washing under roughly 0.5×SSC, 0.1% SDS, and 42° C., even more severely under roughly 0.1×SSC, 0.1% SDS, and 65° C., though the hybridization conditions are not limited to these. Specific examples of such complementary strands include strands with the base sequences completely complementary to the base sequences of the target plus strands, and strands with the base sequences having at least 90%, preferably 95% homology to such strands.

The test drug of the present invention may be designed, for example, based on the base sequence of the human-derived CCDC3 gene represented by SEQ ID NO:1, using, for example, a vector NTI (Infomax). Specifically, a primer or probe candidate sequence, or a sequence that includes at least such a candidate sequence, obtained by processing the CCDC3 gene base sequence with vector NTI software, may be used as a primer or a probe.

As described above, the test drug of the present invention has a length of at least 15 contiguous bases. However, the length may be appropriately selected and set according to the specific use of the test drug.

The test drug of the present invention may be used as a primer or a probe according to an ordinary method in the known methods of specifically detecting specific genes, including northern blotting, RT-PCR method, and in situ hybridization. The use of the test drug enables evaluation of the presence or absence of a CCDC3 gene expression, or the expression level (expression amount) of CCDC3 gene in the visceral adipose tissue of a subject.

The measurement sample (biological sample) may be selected according to the type of the detection method used. For example, the measurement sample may be a total RNA prepared according to an ordinary method from the collected specimen, which may be blood, or a part of the visceral adipose tissue collected from a subject by biopsy. Various polynucleotides prepared from the RNA also may be used as the measurement sample.

When the test drug of the present invention is used as a primer for the detection (gene diagnosis) of visceral obesity, for example, a polynucleotide of typically 15 bp to 100 bp, preferably 15 bp to 50 bp, more preferably 15 bp to 35 bp may be used as the polynucleotide having at least 15 contiguous bases of the base sequence of the CCDC3 gene, and/or a complementary polynucleotide thereof. For use as a detection probe, the test drug may be, for example, a polynucleotide of a length from typically 15 bp to the whole base sequence, preferably 15 bp to 1 kb, more preferably 100 bp to 1 kb.

The test drug of the present invention (probe or primer) may include suitable labels, for example, such as fluorescent dyes, enzymes, proteins, radioisotopes, chemiluminescence substances, and biotins, added to the test drug for the detection of CCDC3 gene.

The fluorescent dye used in the present invention may be those generally used for the labeling and the detection or quantification of nucleic acids. Non-limiting examples include HEX (4,7,2',4',5',7'-hexachloro-6-carboxyl fluorescein, green fluorescent dye), fluorescein, NED (commercially available from Applied Biosystems; yellow fluorescent dye), 6-FAM (commercially available from Applied Biosystems; yellow-green fluorescent dye), and rhodamins or derivatives thereof [for example, tetramethyl rhodamin (TMR)]. The nucleotide may be labeled with a fluorescent dye using a method suitably selected from known methods [see Nature Biotechnology, 14, 303-308 (1996)]. Commercially available fluorescence labeling kits also may be used (for example, the oligonucleotide ECL 3'-oligolabeling system from Amersham Pharmacia).

Further, the probe (oligo or polynucleotide) may be used by being immobilized on any solid phase. Accordingly, the test drug of the present invention may be provided in the form of an immobilized probe obtained by immobilizing the probe (oligo or polynucleotide) (for example, a probe-immobilized DNA chip, cDNA microarray, oligo DNA array, and membrane filter; hereinafter collectively referred to as "DNA chips").

The solid phase used for immobilization is not particularly limited, as long as the oligo or polynucleotide can be immobilized. For example, glass plates, nylon membranes, microbeads, silicon chips, capillaries, and other substrates can be used. The oligo or polynucleotide may be immobilized on a solid phase by placing the oligo or polynucleotide thereon after being synthesized, or by synthesizing the oligo or polynucleotide of interest on a solid phase. The immobilization method is known in the art, and can be selected according to the type of immobilized probe [for example, in situ synthesis of oligonucleotide using a photolithographic technique (Affymetrix) or inkjet technique (Rosetta Inpharmatics)]. For example, in the case of a DNA microarray, the probe may be immobilized using a commercially available spotter (Amersham).

The DNA chips immobilizing the test drug (probe) of the present invention may be hybridized with the labeled DNA or RNA prepared from the RNA collected from a biological tissue, and the resulting conjugate formed by the hybridization of the probe with the labeled DNA or RNA may be detected using the label of the labeled DNA or RNA as an index. The presence or absence of CCDC3 gene expression, or the expression level (expression amount) of the CCDC3 gene in a biological tissue can then be evaluated.

The DNA chips may include one or more test drugs (probes) of the present invention that can bind to the CCDC3 gene. By using DNA chips that include more than one test drug (probe), the presence or absence of more than one gene, or the expression level of these genes can be simultaneously evaluated for a single biological sample.

The test drug of the present invention is useful for the detection of visceral obesity in a subject (the presence or absence of obesity, or the diagnosis of the extent of the disease). Specifically, the test drug can be used to diagnose visceral obesity by determining the difference in the CCDC3 gene expression level between the biological tissue of a subject and the biological tissue or sample of a normal individual (non-visceral obesity individual). In this case, because the CCDC3 gene has increased expression in the visceral fat of visceral obesity individuals, the biological tissue or sample of the subject has increased expression of the gene (mRNA). Thus, the subject has a high possibility of having visceral obesity when the expression amount of the gene in the subject is higher than that in the biological tissue or sample of the normal individual (non-visceral obesity individual) by 50% or more, preferably 10.0% or more, more preferably 200% or more.

(2) Antibody

The present invention provides an antibody that can be used as a test drug to specifically recognize CCDC3 protein. A specific example of the antibody is an antibody that can specifically recognize the human-derived CCDC3 protein having the amino acid sequence of SEQ ID NO:3.

As described above, the present invention is based on the finding that CCDC3 gene expression specifically increases in the visceral adipose tissue of visceral obesity individuals; and the underlying idea of the invention is that visceral obesity or the extent of visceral obesity can be detected in a subject by detecting the presence or absence of a CCDC3 protein production increase, or the extent of the increase in the subject.

Thus, the antibody can be used as a tool (test drug) with which visceral obesity or the extent of visceral obesity can be diagnosed in a subject through the detection of the presence or absence of a CCDC3 protein production increase, or the extent of the increase in the subject.

The form of the antibody of the present invention is not particularly limited, and the antibody may be a polyclonal antibody that uses the CCDC3 protein as the immunogen, or may be a monoclonal antibody. The antibody of the present invention also encompasses antibodies that show antigen binding to a polypeptide of typically at least 8 contiguous amino acids, preferably 15 contiguous amino acids, more preferably 20 contiguous amino acids of the CCDC3 amino acid sequence.

Producing methods of such antibodies are known, and the antibody of the present invention can be produced using these ordinary methods (Current protocols in Molecular Biology, Chapter 11.12 to 11.13 (2000)). Specifically, when the antibody of the present invention is a polyclonal antibody, the antibody can be obtained according to an ordinary method from the serum of an immunized animal produced by immunizing a non-human animal such as house rabbit with the CCDC3 protein purified after being expressed in, for example, *Escherichia coli* using an ordinary method, or with an oligopeptide synthesized using an ordinary method and including a partial amino acid sequence of the CCDC3 protein. In the case of monoclonal antibody, the antibody can be obtained from the hybridoma cells prepared by fusing the spleen cells and myeloma cells obtained by immunizing a non-human animal such as mouse with the CCDC3 protein purified after being expressed in, for example, *Escherichia coli* using an ordinary method, or with an oligopeptide synthesized using an ordinary method and including a partial amino acid sequence of the protein (Current protocols in Molecular Biology edit. Ausubel et al. (1987) Publish. John Wiley and Sons. Section 11.4 to 11.11).

The CCDC3 protein used as an immunogen for the production of the antibody can be obtained according to procedures such as DNA cloning, construction of plasmids, host transfection, culturing the transformant, and collection of the protein from the culture, based on the gene sequence information (for example, SEQ ID NO:1 or 2) provided by the present invention. These procedures can be performed according to methods known to skilled artisan, or previous methods (for example, Molecular Cloning, T. Maniatis et al., CSH Laboratory (1983), DNA Cloning, D M. Glover, IRL PRESS (1985)).

Specifically, the protein as an immunogen for the production of the antibody of the present invention can be obtained by producing a recombinant vector (expression vector) that allows the CCDC3 protein coding gene to be expressed in a desired host cell. The recombinant vector is then introduced into the host cell to obtain a transformant. The transformant is cultured, and the target protein is collected from the resulting culture. The partial peptide of CCDC3 protein can be produced using a common chemical synthesis (peptide synthesis) technique based on the amino acid sequence information (SEQ ID NO:3, 4) provided by the present invention.

Note that the CCDC3 protein of the present invention encompasses not only the proteins concerning the amino acid sequence of SEQ ID NO:3 or NO:4, but homologues thereof. An example of such homologues is a protein that has the amino acid sequence of SEQ ID NO:3 or NO:4 with the deletion, substitution, or addition of one or more amino acids, and that has immunologically the same activity as the protein represented by SEQ ID NO:3 or NO:4.

Examples of the protein with the same immunological activity include proteins that induce specific immune reaction in a suitable animal or in cells thereof, and that are capable of specifically binding to the antibody against the CCDC3 protein.

The number of amino acid mutations, and the mutation sites in the protein are not limited, as long as the immunological activity is maintained. The index as to which and how many amino acid residues should be substituted, inserted, or deleted without losing the immunological activity can be found by using a computer program known to skilled artisan, for example, such as DNA Star software. For example, the number of mutations is typically within 10%, preferably within 5%, further preferably within 1% of the all amino acids. Substituted amino acids are not particularly limited, as long as the protein resulting from the substitution maintains the immunological activity of the CCDC3 protein. From the standpoint of maintaining the protein structure, the substituted amino acids are preferably those similar in properties, such as the reside polarity, charge, solubility, hydrophobicity, hydrophilicity, and amphipathicity, to the amino acids before the substitution. For example, amino acids can be classified into nonpolar amino acids (Ala, Val, Leu, Ile, Pro, Met, Phe, Trp), uncharged amino acids (Gly, Ser, Thr, Cys, Tyr, Asn, Gln), acidic amino acids (Asp, Glu), and basic amino acids (Lys, Arg, His). Amino acids belonging to the same group can thus be appropriately selected using this classification as an index.

The antibody of the present invention may be one prepared by using an oligopeptide having a partial amino acid sequence of CCDC3 protein. The oligo(poly)peptide used to produce the antibody does not need to have a functional biological activity, but should desirably have immunogen properties similar to those of the CCDC3 protein. A preferred example is an oligo(poly)peptide that has such immunogen properties, and that includes at least 8 contiguous amino acids, preferably 15 contiguous amino acids, more preferably 20 contiguous amino acids of the CCDC3 protein amino acid sequence.

The antibody against the oligo(poly)peptide also may be produced by enhancing the immunological reaction with various adjuvants selected according to the type of host. Non-limiting examples of the adjuvants include Freund's adjuvant, mineral gel such as aluminum hydroxide, surface active materials such as lysolecithin, pluronic polyol, polyanion, peptide, oil emulsion, keyhole lympet hemocyanin, and dinitrophenol, and human adjuvants such as BCG (Bacille de Calmette et Guerin) and *corynebacterium parvum*.

The antibody that recognizes the CCDC3 protein concerned with the present invention includes, but is not limited to, the following antibodies (i) to (iii).
(i) Antibody having the amino acid sequences of SEQ ID NOS:31, 32, and 33 for CDR1, CDR2, and CDR3, respectively, of the heavy-chain variable domain, and the amino acid sequences of SEQ ID NOS:35, 36, and 37 for CDR1, CDR2, and CDR3, respectively, of the light-chain variable domain.

Non-limiting examples of the antibody include preferably an antibody that has a heavy-chain variable domain with the amino acid sequence represented by SEQ ID NO:30, and a variable light domain with the amino acid sequence represented by SEQ ID NO:34.
(ii) Antibody having the amino acid sequences of SEQ ID NOS:39, 40, and 41 for CDR1, CDR2, and CDR3, respectively, of the heavy-chain variable domain, and the amino acid sequences of SEQ ID NOS:43, 44, and 45, respectively, of the light-chain variable domain.

Non-limiting examples of the antibody include preferably an antibody that has a heavy-chain variable domain with the amino acid sequence of SEQ ID NO:38, and a variable light domain with the amino acid sequence of SEQ ID NO:42.
(iii) Antibody having the amino acid sequences of SEQ ID NOS:47, 48, and 49 for CDR1, CDR2, and CDR3, respectively, of the heavy-chain variable domain, and the amino acid sequences of SEQ ID NOS:51, 52, and 53 for CDR1, CDR2, and CDR3, respectively, of the light-chain variable domain.

Non-limiting examples of the antibody include preferably an antibody that has a heavy-chain variable domain with the amino acid sequence of SEQ ID NO:46, and a variable light domain with the amino acid sequence of SEQ ID NO:50.'

The antibody that recognizes the CCDC3 protein concerned with the present invention also includes antibodies that bind to the epitope bound to the antibodies (i) to (iii).

The antibody of the present invention has the property to specifically bind to the CCDC3 protein, and thus can be used to specifically detect the CCDC3 protein expressed in the tissue of a subject, or the CCDC3 protein secreted into the blood. That is, the antibody is useful as a probe for detecting the presence or absence of CCDC3 protein, or the extent of CCDC3 protein in the biological tissue or biological sample (including blood) of a subject.

Specifically, the antibody of the present invention can be used as a probe, using an ordinary method, for the detection of CCDC3 protein according to a known detection method, for example, such as western blotting and ELISA, using a tissue extract of protein prepared according to an ordinary method from the collected specimen, which may be blood collected from a subject, or a part of the subject's visceral adipose tissue obtained by biopsy or some other procedure.

Visceral obesity can be diagnosed by determining the difference in the amount of CCDC3 protein between the biological tissue or biological sample of a subject and the biological tissue or biological sample of a normal individual (non-visceral obesity). Specifically, because the CCDC3 gene has higher expression in the visceral adipose tissue of a visceral obesity individual than in the visceral adipose tissue of a normal individual (non-visceral obesity), visceral obesity is suspected when the amount of CCDC3 protein in the biological tissue of a subject, or the amount of CCDC3 protein secreted into a biological sample (such as blood) is higher than in the biological tissue or biological sample of a normal individual (non-visceral obesity) by 50% or more, preferably 100% or more, more preferably 200% or more.

(3) Test Drug Kit

The present invention provides a test drug kit that includes the test drug and is used for the detection or diagnosis of visceral obesity. The detection kit includes at least one of the oligo or polynucleotide used as a probe or a primer (may be labeled, or may be immobilized on a solid phase), and the antibody above. In addition to the probe and primer, the test drug kit of the present invention may appropriately include reagents, instruments, and other components required for performing the method of the present invention, including hybridization reagents, probe labels, label detectors, and buffers, as required.

3. Visceral Obesity Detection Method (Diagnosis Method)

The present invention provides a visceral obesity detection method (diagnosis method) that uses the test drug of the present invention.

Specifically, the detection method (diagnosis method) of the present invention detects the gene (mRNA) expression levels of the visceral obesity-associated CCDC3 gene contained in the biological sample collected from a subject, and the protein (CCDC3 protein) derived from the gene, and measures the mRNA expression amount or the amount of the product protein to detect (diagnose) the presence or absence of visceral obesity in the subject, or the extent of visceral obesity.

The detection method of the present invention includes the following steps (1) and (2).

(1) The step of measuring the CCDC3 mRNA expression amount or the amount of the product CCDC3 protein in a biological sample (test sample) collected from a subject.

(2) The step of comparing the measured mRNA expression amount (subject expression amount) or the measured amount of the product CCDC3 protein (subject production amount) of CCDC3 with the mRNA expression amount (control expression amount) or the amount of the product CCDC3 protein (control production amount) of CCDC3 in a biological sample (control sample) collected from a non-visceral obesity individual.

The subject can be determined as having visceral obesity when the subject expression amount or subject production amount is higher than the control expression amount or control production amount as measured by the method.

Examples of the biological sample include samples prepared from the biological tissue (e.g., visceral adipose tissue) collected from a subject, and samples prepared from blood. Specific examples include RNA-containing samples prepared from such tissues, samples containing polynucleotides prepared from RNA-containing samples, and samples containing proteins prepared from the tissues. The RNA-, polynucleotide-, and protein-containing samples can be prepared according to an ordinary method from the collected specimen, which may be blood, or a part of the subject's visceral adipose tissue collected by methods such as biopsy.

Specifically, the detection method of the present invention is performed using the following procedures, according to the type of the biological sample used as the measurement target.

(1) Use of RNA as Measured Biological Sample

When RNA is used as the measurement target, visceral obesity can be detected specifically by a method that includes the following steps (a), (b), and (c).

(a) The step of binding the test drug (polynucleotide) of the present invention to the RNA prepared from a biological sample (test sample) of a subject, or to a complementary polynucleotide transcribed from the RNA.

(b) The step of measuring the test sample-derived RNA or the complementary polynucleotide transcribed from the RNA by using the test drug as an index after binding the test drug to the RNA or the complementary polynucleotide.

(c) The step of comparing the measurement result (subject result) from (b) with the result (control result) obtained in the same manner in steps (a) and (b) for a biological sample (control sample) derived from a non-visceral obesity individual.

The detection method (diagnosis method) is performed by detecting and measuring the CCDC3 gene expression level in the RNA. Specifically, the method can be performed using a known method such as northern blotting, RT-PCR method, DNA chip analysis, and in situ hybridization analysis, using the polynucleotide test drug (polynucleotide) of the present invention as a primer or a probe.

When using northern blotting, the test drug of the present invention can be used as a probe to detect and measure the presence or absence of CCDC3 gene expression in the RNA, or the expression level of CCDC3. As a specific example, the test drug of the present invention (complementary strand) is labeled with a radioisotope ($^{32}$P, $^{33}$P: RI) or a fluorescence substance, and hybridized with the biological tissue-derived RNA of a subject after transferring the RNA to a nylon membrane or the like using an ordinary method. The resulting test drug (DNA) and RNA double strand is then used for the detection and measurement of signals from the test drug labels (labeling substance such as RI or fluorescence substance) using a detector such as a radiation detector (BAS-1800II, Fuji Film) or a fluorescence detector. In another exemplary method, the test drug (probe DNA) is labeled according to the protocol of the AlkPhos Direct Labelling and Detection System (Amersham Pharmacia Biotech), and hybridized with the biological tissue-derived RNA of a subject. Signals from the test drug labels can then be detected and measured using a multi bio-imager STORM 860 (Amersham Pharmacia Biotech).

When using a RT-PCR method, the test drug of the present invention can be used as a primer for the detection and measurement of the presence or absence of CCDC3 gene expression in the RNA, or the expression level of CCDC3. As a specific example, cDNA is prepared from the biological tissue-derived RNA of a subject using an ordinary method. The cDNA is then hybridized with a pair of primers (a plus strand that binds to the cDNA (−strand), and an opposite strand that bind to the +strand) prepared from the test drug of the present invention, in a manner allowing the target CCDC3 gene region to be amplified using the cDNA as the template. A PCR method is then performed according to an ordinary method, and the resulting amplified double-stranded DNA is detected. Note that the amplified double-stranded DNA may be detected, for example, by detecting the labeled double-stranded DNA produced by PCR with primers labeled beforehand with RI or fluorescence substance, or by detecting the hybridization product of a labeled test drug (probe) and the product double-stranded DNA transferred to a nylon membrane or the like using an ordinary method. Note that the labeled double-stranded DNA product may be measured using devices such as Agilent 2100 bioanalyzer (Yokogawa Analytical Systems). Further, a RT-PCR reaction mixture may be prepared according to the protocol of the SYBR Green RT-PCR Reagents (Applied Biosystems), and the product of the reaction performed with ABI PRISM 7700 Sequence Detection System (Applied Biosystems) may be detected.

When using DNA chip analysis, detection may be performed by a method in which a DNA chip carrying the test drug of the present invention as a DNA probe (single-stranded or double-stranded) is prepared and hybridized with the cRNA prepared from the biological tissue-derived RNA of a subject using an ordinary method, and in which the resulting DNA and cRNA double-strand is bound to the labeled probe prepared from the test drug of the present invention. The DNA chip may be one capable of detecting and measuring the CCDC3 gene expression level.

(2) Use of Protein as Measured Biological Sample

When protein is used as the measurement target, the visceral obesity detection method (diagnosis method) of the present invention is performed by detecting the CCDC3 protein in a biological sample, and measuring the amount of the detected protein. Specifically, the method can be performed by using a method that includes the following steps (a), (b), and (c).

(a) The step of binding the CCDC3 protein in a biological sample (test sample) of a subject to the test drug of the present invention (antibody that recognizes the CCDC3 protein) concerning the antibody.

(b) The step of measuring the CCDC3 protein bound to the test drug in the test sample, using the test drug as an index.

(c) The step of comparing the measured result (subject result) from (b) with the result (control result) obtained in the same manner in steps (a) and (b) for a biological sample (control sample) derived from a non-visceral obesity individual.

More specifically, the detection method may be performed by using a method that detects and quantifies the CCDC3 protein using a known method such as western blotting, using the antibody (antibody that recognizes the CCDC3 protein) as the test drug of the present invention.

Western blotting may be performed using the primary antibody and the secondary antibody, for which the test drug of the present invention, and a labeled antibody (antibody that binds to the primary antibody) labeled with a radioisotope (such as $^{125}$I), a fluorescence substance, or an enzyme (such as horseradish peroxidase (HRP)) are used, respectively. Signals from the radioisotope, fluorescence substance, or other labeling substances for the labeled compound can then be detected and measured using devices such as a radiation measurement device (for example, BAS-1800II; Fuji Film), and a fluorescence detector. It is also possible to use the test drug of the present invention as the primary antibody, and then perform detection according to the protocol of the ECL Plus Western Blotting Detection System (Amersham Pharmacia Biotech), followed by measurement with a multi bio-imager STORM 860 (Amersham Pharmacia Biotech).

Note that the measured CCDC3 protein has a glucose output effect in liver cells, and the effect to increase the expression of a rate-limiting enzyme gene in gluconeogenesis, as will be described later in Example 5. There is a certain correlation between protein amount and protein function and activity. Thus, the detection (diagnosis) of visceral obesity according to the present invention also can be performed by measuring the protein function or activity, instead of measuring the amount of the product CCDC3 protein. Specifically, the detection method of the present invention also encompasses a visceral obesity detection (diagnosis) method that involves measurement and detection according to the measurement method disclosed in the present application, using the function or activity of the CCDC3 protein as an index.

(3) Determination of the Presence or Absence of Visceral Obesity (Diagnosis)

Visceral obesity can be diagnosed by comparing and determining the difference between the gene (mRNA) expression level of the CCDC3 gene in a biological tissue (such as visceral adipose tissue and blood) of a subject, or the production amount or the function or activity of the gene expression product protein (CCDC3 protein) (hereinafter, also collectively referred to as "protein levels"), and the gene expression level (mRNA expression amount) or the protein level (amount of the product CCDC3 protein) in a biological tissue (such as visceral adipose tissue and blood) of a normal individual (non-visceral obesity individual).

The procedure requires a biological sample (RNA or protein) collected from the biological tissue of a normal individual (non-visceral obesity individual). Such samples can be collected from the biological tissue (such as visceral adipose tissue and blood) of a non-visceral obesity individual by using methods such as biopsy and blood collection. As used herein, "non-visceral obesity individual" means an individual diagnosed as not having visceral obesity as measured by at least conventional test methods, for example, such as visceral fat area measurement by computed tomography (CT), and abdominal circumference measurement. In the specification, "non-visceral obesity individual" is also referred to as simply "normal individual" or "non-visceral obesity individual".

The comparison of the gene expression level (mRNA expression amount) or protein amount (amount of the product CCDC3 protein) between a subject's biological tissue and a normal individual's biological tissue may be performed by concurrently performing measurement for the subject's biological sample and the normal individual's biological sample. When measurement is not performed concurrently, the mean value or statistical intermediate value of the gene expression levels (mRNA expression amount) of the CCDC3 gene, or of the amounts of the gene expression product protein (amounts or levels of the product CCDC3 protein) measured under uniform measurement conditions using a plurality of (at least two, preferably 3 or more, more preferably 5 or more) normal biological tissues may be used for comparison as the gene expression level (mRNA expression amount) or protein amount (amount of the product CCDC3 protein) of the normal individual.

In determining whether the subject has visceral obesity, visceral obesity is determined or suspected in the subject when the gene expression level of the CCDC3 gene, or the protein level of the expression product CCDC3 protein in the biological tissue of the subject is significantly higher than the levels in the normal individual. Specifically, an increase from the normal individual levels by 50% or more, preferably 100% or more, more preferably 200% or more can be used as an index.

4. Method for Screening Components Effective for Ameliorating Visceral Obesity or Diabetes As will be described later in Examples, the present inventors found strong involvement of CCDC3 protein in visceral obesity or in the progression of visceral obesity, based on the findings that CCDC3 gene expression increases specific to the visceral fat of visceral obesity individuals, and that the CCDC3 protein increases the liver glucose release, and the expression of the rate-limiting enzyme in gluconeogenesis. Knowing that the CCDC3 protein is involved in the onset or progression of visceral obesity and diabetes, it is considered that the substance that can suppress the CCDC3 gene expression (mRNA expression) or CCDC3 protein function and can thus suppress the liver glucose release or gluconeogenesis is useful as a component that effectively ameliorates visceral obesity or diabetes, or as an active ingredient that prevents MS, cardiovascular disease, or diabetes complications caused by progression of visceral obesity.

The screening method of the present invention described below screens test substances for a substance that has any of the following properties, using these as an index.

(3-1) suppression of CCDC3 gene expression (mRNA expression)

(3-2) decrease in the amount of CCDC3 protein production (3-3) decrease in CCDC3 protein activity By searching for such a substance, the method intends to obtain an active ingredient of visceral obesity ameliorating agents, or an active ingredient of preventing agents (anti-visceral obesity agents) for metabolic disease and cardiovascular disease, such as MS, caused by progression of visceral obesity. The method also intends to obtain an active ingredient of diabetes ameliorating agents, or an active ingredient of preventing agents (antidiabetic agents) for diabetes complications caused by progression of diabetes.

Examples of the candidate substance for the active ingredient of anti-visceral obesity agents or antidiabetic agents include nucleic acids, peptides, proteins, organic compounds (including low-molecular compounds and high-molecular compounds), and inorganic compounds. The screening method of the present invention can be performed for samples that contain such candidate substances (will be collectively referred to as "test substances"). Examples of samples that contain candidate substances include cell extracts, gene library expression products, microorganism culture supernatants, bacterial components, and fungal components.

(1) Screening Method for Substance Having CCDC3 Gene Expression Suppressing Activity The method screens test substances for a substance that has CCDC3 gene expression suppressing effect, using the CCDC3 mRNA expression amount as an index, and obtains the substance as an active ingredient of anti-visceral obesity agents or antidiabetic agents.

Specifically, the method can be performed by performing the following steps (1) to (3).

(1) The step of contacting test substances to cells capable of expressing CCDC3 gene.

(2) The step of measuring the CCDC3 gene expression amount in the cells contacted to the test substances.

(3) The step of selecting a test substance that makes the CCDC3 gene expression amount lower than in control cells (control expression amount) not brought into contact with the test substances.

Any cells, endogenous or exogenous, may be used for the screening, as long as the CCDC3 gene can be expressed. The origin of CCDC3 gene is not particularly limited either, and the CCDC3 gene may originate in humans (SEQ ID NO:1), or in other biological species, including non-human mammals such as mice. Preferably, human-derived CCDC3 gene is used. Specific examples of the cells include CCDC3 gene-containing visceral adipose tissue cells (including cells from humans and other biological species), and primary culture cells of isolated visceral adipose tissue cells. It is also possible to use transformed cells prepared to be capable of CCDC3 mRNA expression by introducing a CCDC3 gene cDNA-containing expression vector according to an ordinary method. Tissue, as a collection of cells, also falls within the definition of the cells used for screening.

In step (1) of the screening method of the present invention, the contact conditions for the test substances and the CCDC3 gene expressible cells are not particularly limited. Preferably, culture conditions (such as temperature, pH, and medium composition) that do not cause cell death and that allow for expression of the CCDC3 gene are selected.

Screening of the candidate substances may be performed by contacting the test substances and the CCDC3 gene expressible cells, for example, under the foregoing conditions, in order to search for a substance that suppresses CCDC3 gene expression and lowers the mRNA expression amount. Specifically, the CCDC3 mRNA expression amount in the CCDC3 gene expressible cells cultured in the presence of the test substances is used as an index when it is lower than the CCDC3 mRNA expression amount (control expression amount) in the corresponding CCDC3 gene expressible cells cultured in the absence of the test substances. The test substances contacted to the cells can then be screened for a substance that has a CCDC3 gene expression suppressing effect, or for a candidate substance of an active ingredient of anti-visceral obesity agents or antidiabetic agents.

The measurement (detection, quantification) of the CCDC3 mRNA expression amount can be performed by measuring the CCDC3 mRNA expression amount in the CCDC3 gene expressible cells with, for example, an oligonucleotide (the test drug of the present invention) having a complementary sequence of the CCDC3 mRNA base sequence, using known methods such as northern blotting, RT-PCR method, and real-time quantitative PCR method.

The measurement of the CCDC3 mRNA expression amount also can be performed by using a method that uses a DNA array.

The detection and quantification of the CCDC3 gene expression level also can be performed by measuring the activity of a marker gene-derived protein, using a cell line obtained by introducing a fused gene prepared by attaching a marker gene, for example, such as a luciferase gene to the gene region (expression regulatory region) that regulates CCDC3 gene expression. The screening method for a CCDC3 gene expression control substance according to the present invention encompasses a method that searches for a target substance using the expression amount of the marker gene as an index. In this regard, the concept of the "CCDC3 gene" used in the screening method of the present invention includes a fused gene of the CCDC3 gene expression regulatory region and the marker gene.

Preferably, the marker gene is a structural gene of an enzyme that catalyzes luminescent reaction or color reaction. Aside from the luciferase gene, other specific examples include reporter genes, such as alkaliphosphatase gene, chloramphenicol acetyltransferase gene, β glucuronidase gene, β galactosidase gene, and aequorin gene. Production of the fused gene, and the measurement of the marker gene-derived activity may be performed by using known methods.

The substance selected by the screening method of the present invention can position itself as a gene expression suppressing agent for the CCDC3 gene. The substance suppressing the CCDC3 gene (mRNA) expression becomes a strong candidate substance for visceral obesity ameliorating medicaments, or for medicaments that suppress disease progression and thus prevent the progression of the disease into metabolic disease and cardiovascular disease such as MS. Further, the substance suppressing the CCDC3 gene (mRNA) expression becomes a strong candidate substance for medicaments that ameliorate diabetes through amelioration of the hyperglycemia state, or for medicaments that suppress disease progression and thus prevent the progression of the disease into diabetes complications.

(2) Substance Screening Method Using CCDC3 Production Lowering Activity as Index The method screens test substances for a substance having a CCDC3 protein production lowering effect, using a decrease in the amount of CCDC3 protein production as an index, and obtains the substance as an active ingredient of anti-visceral obesity agents or antidiabetic agents.

Specifically, the method can be performed by performing the following steps (1') to (3').

(1') The step of contacting test substances to cells capable of producing CCDC3 protein.

(2') The step of measuring the amount of the product CCDC3 protein in the cells contacted to the test substances.

(3') The step of selecting a test substance that makes the CCDC3 production amount lower than in control cells (cells capable of CCDC3 production; control production amount) not brought into contact with the test substances.

Any cells, endogenous or exogenous, may be used for the screening (including control cells), as long as the CCDC3 gene can be expressed and CCDC3 protein is produced. The origin of CCDC3 gene is not particularly limited either, and the CCDC3 gene may originate in humans, or in other biological species, including non-human mammals such as mice. Preferably, human-derived CCDC3 gene is used. Specific examples of the cells include CCDC3 gene-containing visceral adipose tissue cells (including cells from humans and other biological species), and primary culture cells of isolated visceral adipose tissue cells.

It is also possible to use transformed cells prepared to be capable of CCDC3 protein production by introducing a CCDC3 gene cDNA-containing expression vector according to an ordinary method. Tissue, as a collection of cells, also falls within the definition of the cells used for screening.

In step (1') of the screening method (3-2) of the present invention, the contact conditions for the test substances and the cells capable of CCDC3 protein production are not particularly limited. Preferably, culture conditions (such as temperature, pH, and medium composition) that do not cause cell death and that allow for production of the CCDC3 protein are selected.

Screening of the candidate substances may be performed by contacting the test substances and the cells capable of CCDC3 protein production, for example, under the foregoing conditions, in order to search for a substance that lowers the amount of the CCDC3 protein produced. Specifically, the amount of the CCDC3 protein produced in the cells capable of CCDC3 protein production cultured in the presence of the test substances is used as an index when it is lower than the CCDC3 production amount (control production amount) in the corresponding cells capable of CCDC3 protein production cultured in the absence of the test substances. The test substances contacted to the cells can then be screened for a substance that has a CCDC3 protein production lowering effect, or for a candidate substance of an active ingredient of anti-visceral obesity agents or antidiabetic agents.

The measurement (detection, quantification) of the CCDC3 protein production amount can be performed by measuring the CCDC3 protein amount from the cells capable of producing CCDC3 protein, using the antibody (anti-CCDC3 antibody; the test drug of the present invention) for the CCDC3 protein according to a known method such as western blotting, immunoprecipitation, and ELISA. Specifically, western blotting may be performed using the primary antibody and the secondary antibody, for which the test drug of the present invention, and a labeled antibody (antibody that binds to the primary antibody) labeled with a radioisotope (such as $^{125}$I), a fluorescence substance, or an enzyme (such as horseradish peroxidase (HRP)) are used, respectively. Signals from these labeling substances can then be measured using devices such as a radiation measurement device (for example, BAS-1800II; Fuji Film), and a fluorescence detector. It is also possible to use the test drug of the present invention as the primary antibody, and then perform detection according to the protocol of the ECL Plus Western Blotting Detection System (Amersham Pharmacia Biotech), followed by measurement with a multi bio-imager STORM 860 (Amersham Pharmacia Biotech).

The substance selected by the screening method of the present invention can position itself as a CCDC3 protein production suppressing agent. The substance suppressing the CCDC3 protein production becomes a strong candidate substance for visceral obesity ameliorating medicaments, or for medicaments that suppress disease progression and thus prevent the progression of the disease into metabolic disease and cardiovascular disease such as MS.

(3) Substance Screening Method Using CCDC3 Protein Function or Activity Lowering Effect as Index The method screens test substances for a substance having a CCDC3 protein function or activity lowering effect, using a decrease in the CCDC3 protein effect as an index, and obtains the substance as an active ingredient of anti-visceral obesity agents or antidiabetic agents.

Specifically, the method can be performed by performing the following steps (1") to (3").

(1") The step of contacting test substances, cells that react with CCDC3 protein, and CCDC3 protein to one another.

(2") The step of detecting CCDC3 protein function or activity in the cells.

(3") The step of selecting a test substance that makes the detected function or activity lower than the CCDC3 protein function or activity of the control cells (cells that react with CCDC3 protein) contacted to CCDC3 protein but not to the test substances.

The cells used for screening that react with CCDC3 protein are cells that show some biological activity in contact with CCDC3 protein. Specific examples of such cells include liver-derived cell lines, and isolated primary cultured cells of the liver. Tissue, as a collection of cells, also falls within the definition of the cells used for screening.

Screening of the candidate substances may be performed by contacting the test substances to the cells that react with CCDC3 protein, or to the cell fractions thereof, for example, under the foregoing conditions, in order to search for a substance that lowers the CCDC3 protein effect. Specifically, the CCDC3 protein function or activity in the CCDC3 protein reacting cells cultured with CCDC3 protein in the presence of the test substances is used as an index when it is lower than the CCDC3 protein function or activity (control function or activity) in the corresponding CCDC3 protein reacting cells cultured with CCDC3 protein in the absence of the test substances. The test substances can then be screened for a substance that has a CCDC3 protein function or activity lowering effect, or for a candidate substance of an active ingredient of anti-visceral obesity agents or antidiabetic agents.

Examples of the CCDC3 protein function or activity include the glucose output promoting effect from the liver cells in response to the CCDC3 protein added to the liver cells, and the effect of increasing the mRNA expression amounts of the gluconeogenesis rate-limiting enzymes glucose-6-phosphatase (G6 Pase) and phosphoenolpyruvate carboxykinase (PEPCK). These functions and activities can be measured using the methods described in Example 5.

(4) Screening Method Using CCDC3 Transgenic Mice

The method screens for test substances for a substance (candidate substance) that can be used as an active ingredient of anti-visceral obesity agents or antidiabetic agents, using, as an index, a decrease in the body weight or glucose level of CCDC3 transgenic mice (CCDC3 Tg mice) transformed to express CCDC3 mRNA and produce CCDC3 protein at high levels.

Specifically, the method can be performed by performing the following steps (a) to (c).

(a) The step of administering a test substance to CCDC3 Tg mice.

(b) Measuring the body weight (subject weight) or glucose level (subject glucose level) of the test substance-administered CCDC3 Tg mice over a time course, and comparing the result with the time-course body weight (control body weight) or glucose level (control glucose level) of CCDC3 Tg mice that did not receive the test substance.

(c) The step of selecting a test substance that makes the subject weight or subject glucose level lower than the control body weight or control glucose level, the test substance being selected as an active ingredient that ameliorates visceral obesity or diabetes.

Figure 7:
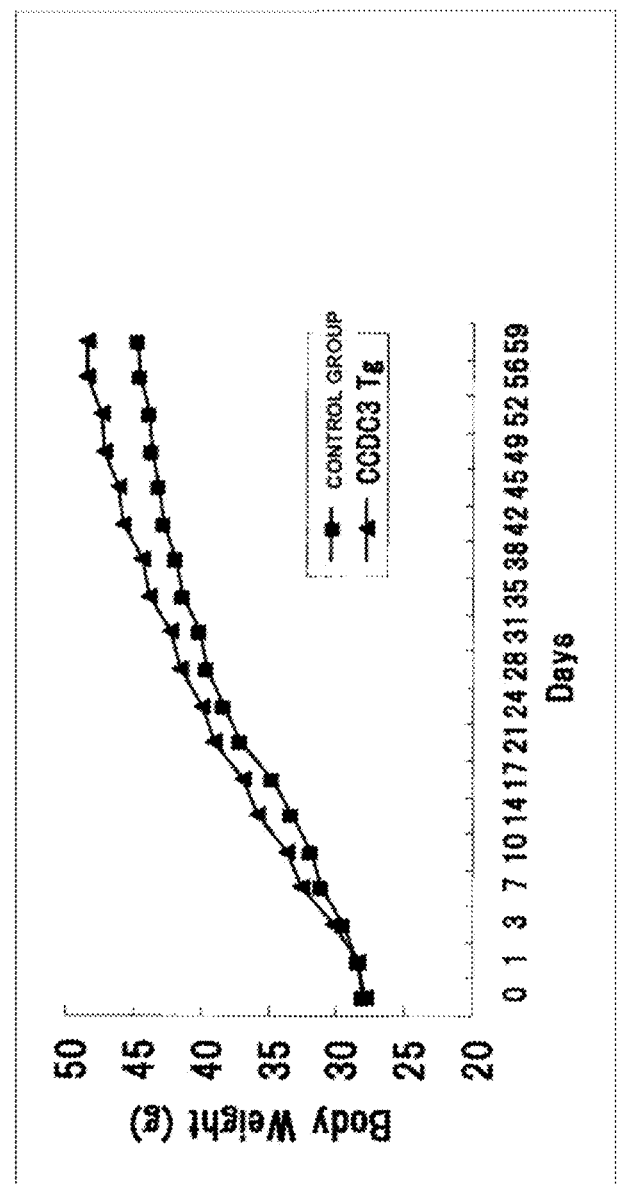
FIG. 7 represents time-dependent changes in body weight under high-fat diet (HFD) in transgenic mice (CCDC3 Tg mice) expressing CCDC3 gene in 4 times or greater amounts and in control group mice (Example 7).
Figure 8:
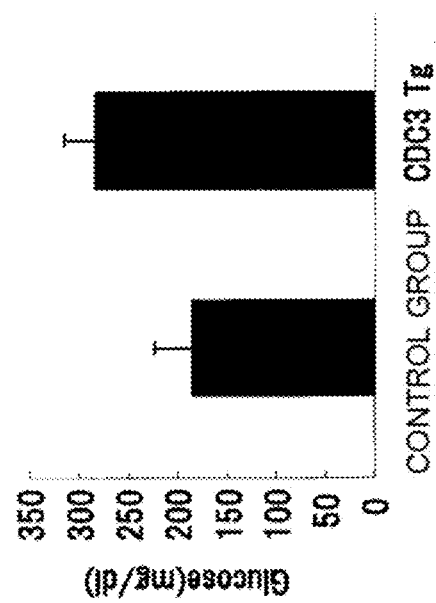
FIG. 8 represents glucose levels (mg/dl) of the blood collected from CCDC3 Tg mice and control group mice on day 52 of HFD ingestion (Example 7).

The CCDC3 Tg mice used for screening are mice artificially transformed to express CCDC3 mRNA at high levels, and can be produced using various methods, including a method involving DNA microinjection into the pronucleus of a fertilized egg, and a method that produces chimeric mice after introduction of DNA into an embryonic stem cell (Mouse Laboratory Manual, 2nd ed., Tokyo Metropolitan Institute of Medical Science, Test Animal Research Department, ed., Springer Japan (2005)). The methods described in Example 7 below also may be used to produce the mice. The mice are characterized by their significantly increased body weights and high glucose levels compared to normal mice even on the same diet (FIGS. 7 and 8).

Screening of the candidate substances can be performed by serially measuring the body weights and glucose levels of the test substance-administered CCDC3 Tg mice (subject mice) and the test substance-free CCDC3 Tg mice (control mice) grown in the same environment. The test substance that significantly lowers the body weights of the subject mice compared with the control mice can then be selected as an active ingredient that ameliorates visceral obesity. The test substance that significantly lowers the glucose levels of the subject mice compared to the control mice can be selected as an active ingredient that ameliorates diabetes.

The substance screened for by the screening methods (1) to (4) has the effect to suppress increased (enhanced) expression of CCDC3 gene in visceral adipose tissue cells and thus suppress liver glucose release or gluconeogenesis. The substance can thus be used as an active ingredient of compositions (anti-visceral obesity agents) that ameliorate visceral obesity or prevent metabolic disease cardiovascular disease, such as MS, caused by progression of the disease. The substance also can be used as an active ingredient of compositions (antidiabetic agents) that ameliorate diabetes or prevent progression of the disease (including onset of diabetes complications).

The candidate substance screened for by the screening method can be further screened using pathological non-human animals having visceral obesity, or pathological non-human animals having metabolic disease or cardiovascular disease such as MS, or diabetes. The candidate substance so screened also can be used in an efficacy test or safety test using pathological non-human animals having visceral obesity or diabetes, or pathological non-human animals having metabolic disease or cardiovascular disease such as MS. It is also possible to use the candidate substance in a clinical test for visceral obesity individuals (humans), or for individuals (humans) in the stage prior to disease onset or individuals suffering from metabolic disease or cardiovascular disease, such as MS, caused by the progression of the disease. More practical active ingredients for anti-visceral obesity agents and antidiabetic agents can be screened and obtained through these tests.

The substance so screened may be industrially produced by using chemical synthesis, biological synthesis (including fermentation), and genetic procedures, depending on the type of substance, after performing structure analysis, as required. The product substance can then be used for the preparation of anti-visceral obesity agents and antidiabetic agents.

5. Anti-Visceral Obesity Agent, Antidiabetic Agent

CCDC3 gene siRNA can suppress CCDC3 mRNA expression in CCDC3 gene-introduced cells, as will be described later in Example 6. The siRNA can be used as an active ingredient of visceral obesity ameliorating agents, or an active ingredient of medicinal agents (anti-visceral obesity agents) for preventing progression of metabolic disease and cardiovascular disease, such as MS, caused by the progression of the disease. The siRNA also has use as an active ingredient of diabetes ameliorating agents, or an active ingredient of medicinal agents (antidiabetic agents) for preventing progression of diabetes complications caused by the progression of the disease.

The present invention thus provides an anti-visceral obesity agent that includes siRNA as an active ingredient for suppressing CCDC3 gene expression. The present invention also provides an antidiabetic agent that includes siRNA as an active ingredient for suppressing CCDC3 gene expression.

The siRNA concerned with the present invention is double-stranded, and is formed by hybridization of a sense strand (a sequence complementary to the target sequence of CCDC3 gene) and an antisense strand complementary to the sense strand. The double strand may be a siRNA (shRNA) molecule of a closed-end structure, for example, a hairpin structure. The siRNA is not particularly limited, as long as it can suppress CCDC3 gene expression. Examples of mouse CCDC3 gene siRNA include:

siRNA #1 that targets the 2236-2256 region of a mouse CCDC3 gene base sequence (SEQ ID NO:2): sense strand r (gacacaugauacugauaaa)dTdT (SEQ ID NO:5), antisense strand r (uuuaucaguaucauguguc)dTdG (SEQ ID NO:6), siRNA #2 that targets the 1506-1526 region: sense strand r (gaaagauguuaagacuuaa)dTdT (SEQ ID NO:7), antisense strand r (uuaagucuuaacaucuuuc)dAdG (SEQ ID NO:8), and siRNA #3 that targets the 2011-2131 region: sense strand r (gaaguauuugcauaacaaa)dTdT (SEQ ID NO:9), antisense strand r (uuuguuaugcaaauacuuc)dTdA (SEQ ID NO:10).

Human CCDC3 gene siRNA can be constructed in the same manner.

The active ingredient of anti-visceral obesity agents or antidiabetic agents of the present invention is not limited to the siRNA that suppresses CCDC3 gene expression, and a nucleic acid that suppresses CCDC3 gene also can be used as the active ingredient of anti-visceral obesity agents or antidiabetic agents. Examples of nucleic acid include miRNA, antisense poly(oligo)nucleotides, ribozymes, aptamers, and decoys for the CCDC3 gene. The antisense poly(oligo)nucleotide has a base sequence complementary to or substantially complementary to the CCDC3 gene base sequence, or has a part of such a sequence, and hybridizes with the CCDC3 gene RNA to inhibit the synthesis or function of the RNA, or modulate or regulate CCDC3 gene expression through interaction with the RNA. Any antisense poly(oligo)nucleotide, including, for example, antisense RNA and antisense DNA, may be used, as long as it has the foregoing effects.

The antisense poly(oligo)nucleotide is configured from typically about 10 to 1,000 bases, preferably about 15 to 500 bases, further preferably about 16 to 30 bases. In order to prevent degradation due to hydrolase such as nuclease, the phosphate residues (phosphates) of the nucleotides forming the antisense DNA may be substituted with chemically modified phosphate residues, for example, such as phosphorothioate, methylphosphonate, and phosphorothioate. The antisense poly(oligo)nucleotide can be produced by using a known device such as a DNA synthesizer.

The active ingredient of anti-visceral obesity agents or antidiabetic agents according to the present invention is not limited to the nucleic acid that suppresses CCDC3 gene, and substances having the effect to suppress the CCDC3 protein function also can be used as the active ingredient of anti-visceral obesity agents or antidiabetic agents. Examples of such substances include antibodies against CCDC3 protein, particularly neutralizing antibodies.

As used herein, neutralizing antibodies mean antibodies having the properties of inhibiting the intrinsic functions or activities of antigens upon binding to the antigens. Neutralizing antibodies against CCDC3 protein mean antibodies having the properties of inhibiting the functions or activities of CCDC3 protein upon binding to the CCDC3 protein.

In addition to the active ingredient (including siRNA, antisense poly(oligo)nucleotide, and antibody) that suppresses CCDC3 gene expression or CCDC3 functions, the anti-visceral obesity agent or antidiabetic agent of the present invention may also include any types of carriers and additives, for example, pharmaceutically acceptable carriers and additives.

Non-limiting examples of pharmaceutically acceptable carriers and additives include excipients such as sucrose and starch; binders such as cellulose and methylcellulose; disintegrants such as starch and carboxymethylcellulose; lubricants such as magnesium stearate and aerosil; aromatizers such as citric acid and menthol; preservatives such as sodium benzoate and sodium bisulfite; stabilizers such as citric acid and sodium citrate; suspensions such as methylcellulose and polyvinylpyrrolidone; dispersants such as surfactants; diluents such as water and physiological saline; and base wax.

Examples of preparations suited for oral administration include liquid, capsule formulations, sachets, tablets, suspension agents, and emulsions. Examples of preparations suited for parenteral administration (for example, subcutaneous injection, intramuscular injection, local injection, intraperitoneal administration) include aqueous and non-aqueous isotonic aseptic injections, which may contain an antioxidant agent, a buffer, an antibacterial agent, a tonicity agent, or other such components. Other examples of parenteral administration preparations include aqueous and non-aqueous aseptic suspension agents, which may contain a suspension, a solubilizer, a thickener, a stabilizer, an antiseptic, or other such components.

The dose of the preventative or therapeutic agent of the present invention varies depending on factors such as the body weight and age of the subject, and the seriousness of disease, and cannot be set definitively. For example, the agent may be given in several milligrams to several ten milligrams/kg body weight/day for adults in terms of an active ingredient amount, once a day, or in divided portions several times a day.

When the active ingredient is encoded by DNA, it is considered possible to perform a gene therapy by incorporating the DNA into a vector for gene therapy. Further, when the active ingredient is an antisense polynucleotide, a gene therapy can be performed by incorporating the antisense polynucleotide either directly or via a vector for gene therapy. As above, the dose of the gene therapy composition, and the administration method vary depending on factors such as the body weight, age, and symptom of a patient, and may be appropriately selected by a skilled artisan.

EXAMPLES

The present invention is described below based on Examples. Note, however, that the present invention is not limited to the following Examples. Further, in the Examples below, procedures such as gene modifications and cell cultures followed the methods described in, for example, Molecular Cloning: A Laboratory Manual, Second Edition (1989) (Cold Spring Harbor Laboratory Press), Current Protocols in Molecular Biology (Greene Publishing Associates and Wiley-Interscience), unless otherwise stated.

Example 1

Microarray Analysis Using Human Adipose Tissue (1) Obesity Patients Adipose Tissue Used in DNA Microarray Analysis Abdominal visceral adipose tissue and abdominal subcutaneous adipose tissue were donated by patients arranged to undergo surgical operation at Shiga University of Medical Science Hospital, after explaining the content of the research and obtaining their consent. A total of 10 patients, male, from age 55 to 75 were categorized into two groups: non-visceral obesity individuals (normal glucose tolerance) with abdominal circumferences of less than 85 cm (5 cases, average abdominal circumference of 78.5 cm±2.5 cm), and visceral obesity individuals (normal glucose tolerance) with abdominal circumferences of 85 cm and higher (5 cases, average abdominal circumference of 90.7 cm±3.6 cm).

(2) Search for Genes that Show Varying Expression Specific to Obesity Patients Visceral Adipose Tissue The frozen visceral adipose tissue and frozen subcutaneous adipose tissue of the five non-visceral obesity individuals and the five visceral obesity individuals were sliced into about a 5 mm×5 mm size, and homogenized in QIAzol Lysis Reagent (Qiagen) using TissueLyser (Qiagen). Chloroform was added and mixed with the resulting homogenate, and the aqueous layer was collected by centrifugation. Total RNA was isolated and purified from the aqueous layer using RNeasy Lipid Tissue Mini Kit (Qiagen), according to the protocol attached to the Kit. The purified total RNA was quantified at 260 nm absorbance, and checked for the absence of RNA degradation using an Agilent 2100 Bioanalyzer (Agilent Technologies).

This was followed by labeled cRNA synthesis, which was performed using a Low RNA Input Linear Amplification Kit (Agilent Technologies) according to the single-dye method experiment protocol attached to the Kit. cDNA was synthesized with 500 ng of the purified total RNA by reverse transcription reaction, using oligo-dT primers that included T7 promoter added to the 5' end. By using the cDNA as a template, labeled cRNA was synthesized by in vitro transcription performed with T7 RNA Polymerase in the presence of Cy3-labeled UTP (PerkinElmer). The resulting labeled cRNA was purified with RNeasy Mini Kit (Qiagen), and the yield was quantified at 260 nm absorbance.

After fragmenting the Cy3-labeled cRNA, hybridization was performed at 65° C. for 17 hours using Whole Human Genome Oligo Microarray (Agilent Technologies). The microarray was washed and dried, and a Cy3 wavelength fluorescence image was obtained using a DNA microarray scanner (Agilent Technologies). The fluorescence signal of each probe was then quantified using Feature Extraction Software (Agilent Technologies). Data were analyzed using GeneSpring version 7.0 (Agilent Technologies). The microarrays were normalized by setting the same median value for the signals of the all probes on the array.

The analysis revealed the presence of the coiled-coil domain containing protein 3 (CCDC3) gene, whose expression in the visceral adipose tissue of the visceral obesity individuals was higher than in the visceral adipose tissue of the non-visceral obesity individuals by a factor of 3.2 (left-hand side in FIG. 1). In contrast, in the subcutaneous adipose tissue, CCDC3 gene expression was only slightly higher in the visceral obesity individuals than in the non-visceral obesity individuals (right-hand side in FIG. 1). There results

Example 2

CCDC3 Expression Analysis in Obesity Model db/db Mice (1) Real-time PCR was performed to examine whether the increased CCDC3 gene expression in the visceral fat of the obesity patients changes in the adipose tissue of obesity pathological model mice (db/db mice). For the analysis, db/db male mice (CLEA Japan), 15 weeks old were used, and db/m mice (CLEA Japan) were used as a control group.

Figure 2:
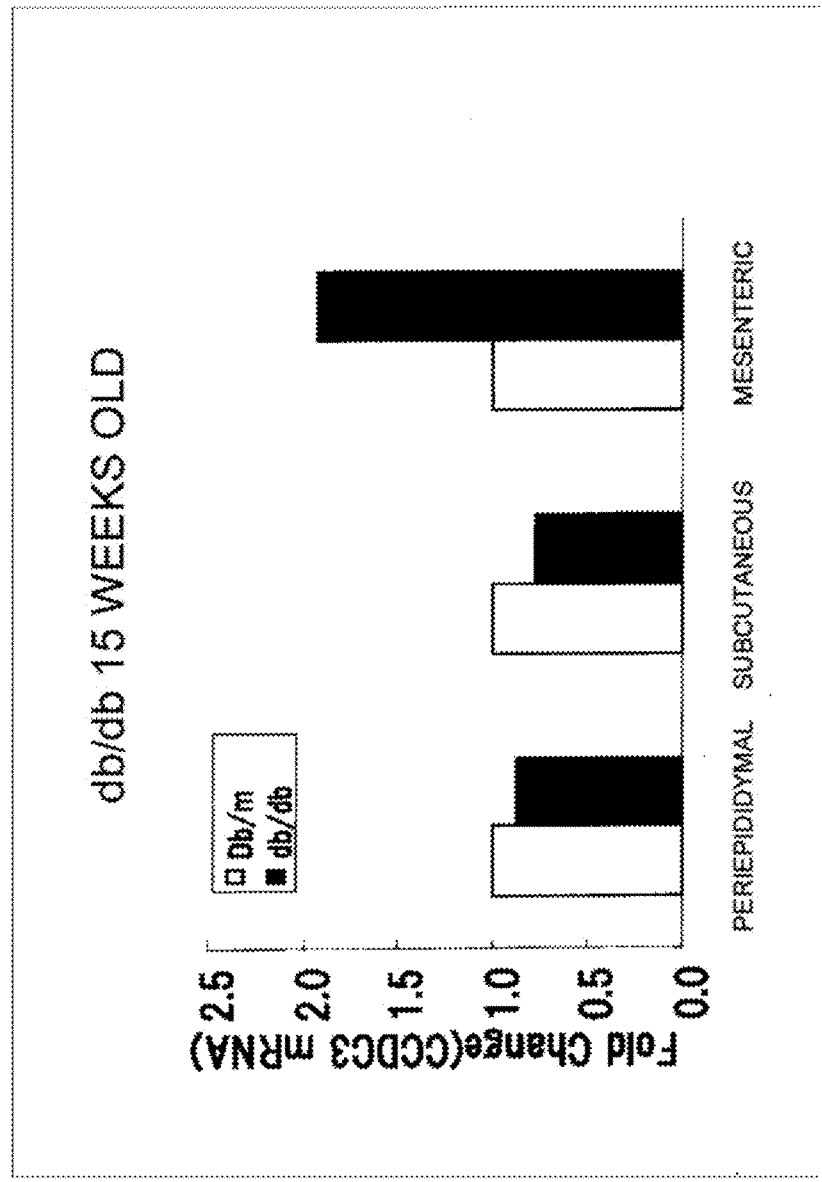
FIG. 2 represents the result of the comparison of CCDC3 gene (mRNA) expression amount between the mesenteric adipose tissue, subcutaneous adipose tissue, and periepididymal adipose tissue of obesity model mice (db/db mice) and db/m mice (control group). The CCDC3 gene expression amount in the obesity model mice (db/db mice) is presented as the relative ratio with respect to the expression amount 1 of the control group. The CCDC3 gene expression amount in the mesenteric adipose tissue of the obesity model mice had a 2.1-fold increase over the expression amount in the mesenteric adipose tissue of the control group (Example 2).

The mesenteric adipose tissue (visceral adipose tissue), and the subcutaneous adipose tissue and periepididymal adipose tissue (both for comparison) were collected from five mice in each group, and RNA was prepared. The RNAs of the five mice in each group were pooled as a total RNA sample for microarray analysis. The methods of Example 1(2) were used for the RNA preparation, cDNA synthesis, microarray analysis, and detection. Note, however, that a Whole Mouse Genome Oligo Microarray for mice (Agilent Technologies) was used as the microarray. The analysis confirmed a 2.1-fold increase in CCDC3 gene expression in the mesenteric fat of the obesity model mice (db/db mice) over the control groups (FIG. 2).

The results of the microarray analysis of the humans and the obesity model mice suggested that a CCDC3 gene expression amount could be used as an index to determine obesity, particularly visceral obesity.

(2) The obesity pathological model mice DIO (Diet-Induced Obese) mice, 20 weeks old, were used for experiment that compared high expression genes (2-fold or more, vs CE-2 diet mice) and low expression genes (0.5-fold or more, vs CE-2 diet mice) in the mesenteric fat and periepididymal fat. Note that the DIO mice were produced from C57BL/6J Jcl male mice (CLEA Japan), 7 weeks old, that had the high-fat diet (HFD) 58Y1DIO P.D. 60% Energy From Fat-Blue (Japan SLC) for 13 weeks. As a control group, mice produced from C57BL/6J Jcl male mice (CLEA Japan), 7 weeks old, that had CLEA Rodent Diet CE-2 (CLEA Japan) for 13 weeks were used. An investigation found that the number of genes that showed expression changes under a high-fat diet load was 1,241 (338±229=567 high expression genes, 360±314=674 low expression genes) in the mesenteric fat, and 3,205 (1,349±229=1,578 high expression genes, 1,313±314=1,627 low expression genes) in the periepididymal fat (Table 1), demonstrating that expression varies in greater numbers of genes in the periepididymal fat. However, only a few genes showed expression changes in the both mesenteric and periepididymal adipose tissues (229 high expression genes, 314 low expression genes), revealing that these adipose tissues show different-gene expression changes, even though the both are white adipose tissues (see Table 1).

TABLE I

|  | Number of high expression genes | Number of low expression genes |
|---|---|---|
| Mesenteric fat only | 338 | 360 |
| Epididymal fat only | 1349 | 1313 |
| Mesenteric fat and epididymal fat | 229 | 314 |

Example 3

Confirmation for Secretory Protein

The amino acid sequence of CCDC3 protein was analyzed by using two algorithms, Neural Network (NN) and Hidden Markov Model (HMM) of SignalP 3.0, a webtool for predicting the signal sequence site and its cleavage site in an amino acid sequence. The both algorithms suggested the possibility that the CCDC3 protein is a protein with a signal sequence, and it was inferred that its cleavage site was between amino acid residues 21 and 22.

Figure 3:
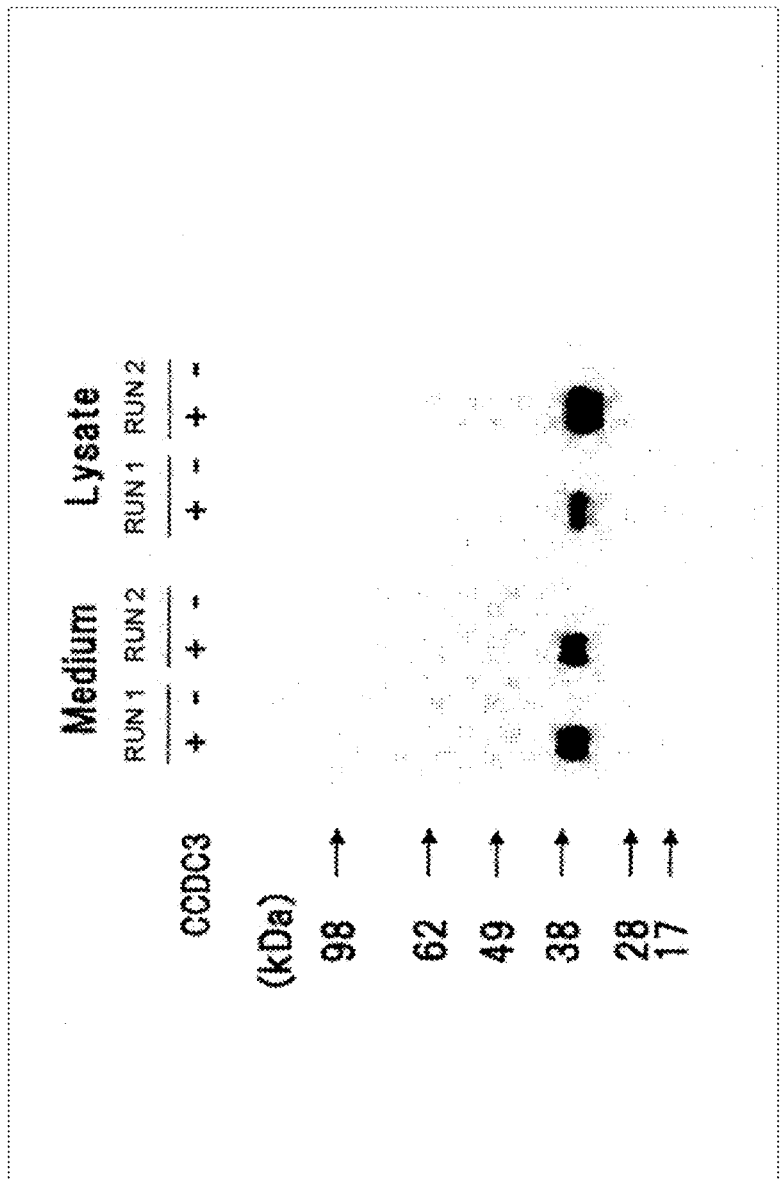
FIG. 3 represents the result of the western blotting detection of CCDC3 protein secreted into medium from HEK293T cells that had human CCDC3 overexpression vector pReceiver-CCDC3 introduced into the cells. The CCDC3 protein signals recognized in the medium suggested that CCDC3 protein was a secretory protein (Example 3).

To confirm this, human CCDC3 overexpression vector pReceiver-CCDC3 was introduced into HEK293T cells, and the CCDC3 protein secreted into a medium was detected by western blotting. Specifically, CCDC3 expression vector pReceiver-CCDC3 was introduced into HEK293T cells cultured to about 80% confluence in a 10-cm petri dish, according to the manual attached to Lipofectamine 2000 (Invitrogen). After 40 hours from the introduction, the culture and a cell extract dissolved in 1-mL Lysis buffer (25 mmol/L Tris-HCl (pH 8) containing 0.1 mol/L NaCl, 1% Triton X-100, and protein inhibitor) were collected, and subjected to western blotting in 10 μL and 0.8 μL, respectively (reduced state). For the detection, anti-FLAG M2-HRP antibodies (SIGMA) and ECL plus (GE Healthcare Biosciences) were used. The results are presented in FIG. 3.

The analysis results confirmed the CCDC3 protein signal in the culture (medium), suggesting that the CCDC3 protein is a secretory protein.

Example 4

Purification of Human CCDC3 Recombinant Protein

A human CCDC3 expression vector pReceiver-M14-human CCDC3 with a 3×Flag tag fused on the C-terminus side was purchased from GeneCopoeia. The human CCDC3 expression vector was used as a template, and a plasmid with an inserted base sequence that encodes a 3×Flag tag cutting, thrombin-specific cut amino acid recognition sequence was constructed, and used for protein expression purification. The human CCDC3 expression vector was transfected into Freestyle293 cells using 293fectin (Invitorogen), according to an ordinary method. The cells were shake cultured in a Freestyle293 expression medium (Gibco) at 37° C. for 2 days, and the culture supernatant was collected by centrifugation. The culture supernatant was then applied to an ANTI-FLAG M2 Affinity Gel (Sigma) column equilibrated beforehand with a 0:5 M NaCl-containing 20 mM HEPES-Na buffer (pH 7.5) to adsorb the 3×Flag tag-fused CCDC3 protein. After being washed with the same buffer equivalent of the volume of five columns, the CCDC3 protein was eluted with the same buffer containing 0.1 mg/ml 3×FLAG Peptide (Sigma). The elution fraction was electrophoresed by SDS-PAGE, and a 3×Flag tag-fused CCDC3 protein with a molecular weight of 34 kDa was confirmed. The CCDC3 protein-containing fraction was concentrated with Amicon Ultra-15 Centrifugal Filter 10 k MWCO (Millipore), and 1 unit of thrombin (Sigma, T7513-100u) was added per about 10 μg of the CCDC3 protein to cut the 3×Flag tag in a 15-hour treatment at room temperature. After the cutting treatment, the liquid was applied to Benzamidine Sepharose 6B resin to remove the thrombin. As the final purification, the sample was applied to a Superdex 200 16/60 column (GE healthcare) equilibrated with the buffer, and the elution fraction was electrophoresed by SDS-PAGE to collect a CCDC3 protein with a molecular weight 31 kDa. The protein was obtained as a purified sample of the human CCDC3 recombinant protein.

Example 5

Influence on Human CCDC3 Recombinant Protein Stimulation on Liver Glucose Release (1) Isolation of Rat Liver Cells Wistar rats (10 weeks old, male) were anesthetized with pentobarbital, and the liver was perfused by cannulation with an about 350 mL of Liver Perfusion Medium (Invitrogen 17701-038) that contained 2% penicillinstreptomycin. Perfusion was continued further for about 10 min with Liver Digest Medium (Invitrogen 17703-034). The perfused liver was transferred to a 15-cm petri dish, and shaken in Hepatocyte Wash Medium (Invitrogen 17704-024) supplemented with 1% FBS (GIBCO) and 1% penicillinstreptomycin (GIBCO) to liberate the cells. The liver cells suspended in Hepatocyte Wash Medium was filtered through a gauze (4 layers), and collected into a 50-ml Falcon tube. After centrifugation at 400 rpm for 1 min at 4° C., the supernatant was discarded, and the precipitated liver cells were suspended in a new Hepatocyte Wash Medium, and centrifuged at 400 rpm for 1 min at 4° C. After removing the supernatant, the collected liver cells were suspended in an ice-cooled Hepatocyte Wash Medium supplemented with 10% FBS and 1% penicillinstreptomycin, and centrifuged (400 rpm, 2 min, 4° C.). The washing procedure was repeated twice. The resulting liver cells were suspended in an about 10-mL 10% FBS Hepatocyte Wash Medium, and counted after trypan blue staining. The cells were appropriately diluted with 10% FBS William's E Medium (SIGMA-ALDRICH, W4128), and used for the experiments below.

(2) Glucose output Measurement in Liver Cells

The liver cells isolated as above were inoculated on a 24-well collagen plate (BIOCOAT) in $2.5 \times 10^5$/well, and cultured for 4 hours. The cells were then cultured overnight in a William's medium E supplemented with 0.5% BSA (SIGMA) and 100 nM dexamethasone (SIGMA). On the next day, the medium was exchanged with a medium prepared by adding gluconeogenesis substrate (2 mM lactate (SIGMA-ALDRICH, L-1750) and 0.2 mM pyruvate (Nacalai tesque)) to glucose free DMEM (SIGMA, D5030), and assessment was made whether the human recombinant CCDC3 protein (100 nM) prepared in Example 4 has any influence on glucose output in the presence or absence of protein stimulation.

Figure 4:
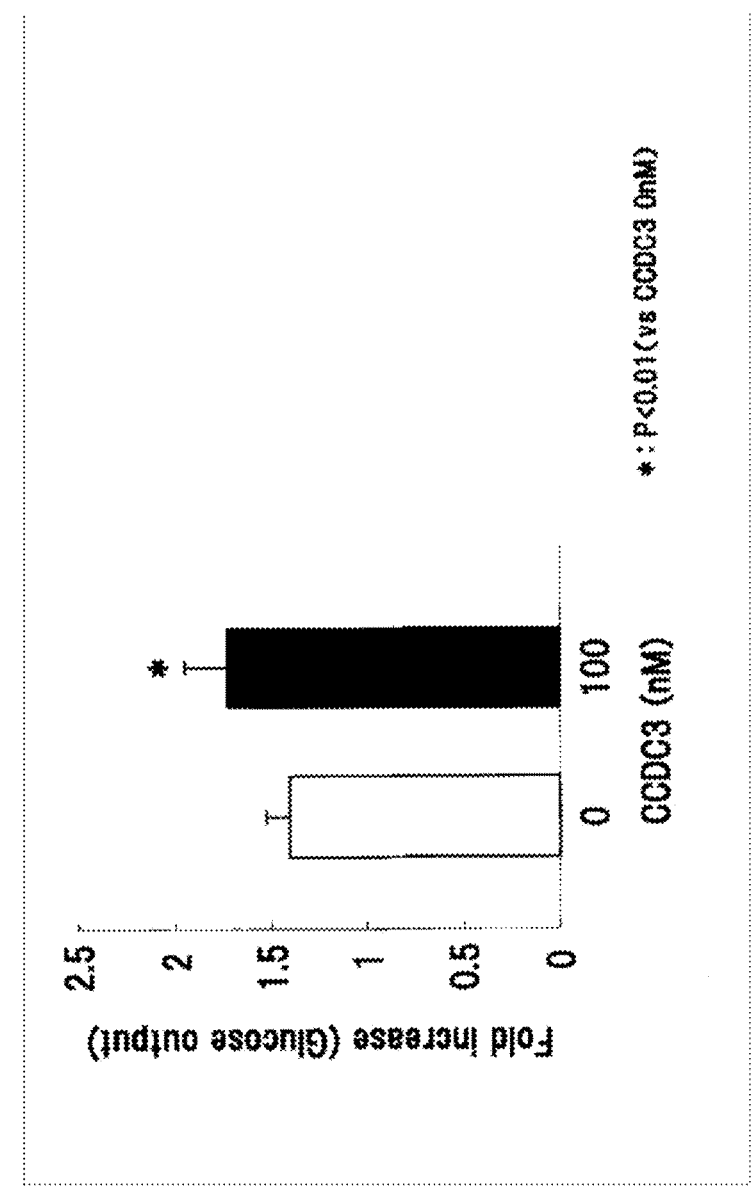
FIG. 4 represents the result of the examination of the influence of 100 nM human recombinant CCDC3 protein stimulations on glucose output using isolated liver cells from rats. Increased glucose output by 100 nM CCDC3 protein stimulation was confirmed (CCDC3 0 nM vs 100 nM, 1.2-fold increase, n=6, p<0.01) (Example 5(2)).

As a positive control of liver glucose release increase, 3 nM glucagon (Peptide Institute, 4098-s) was used. After medium exchange, the cells were cultured at 37° C. for 4 hours, and the supernatant was collected. The liver cells were washed with PBS(−), and dissolved in 0.25 N NaOH (250 μl). The glucose concentration in the supernatant, and the protein amount were quantified using a glucose C-II-test wako (WAKO, 437-90902), and a BCA protein assay kit (PIERCE 23225), respectively. The glucose concentration was corrected with the liver cell protein amount. The results are presented in FIG. 4. As shown in FIG. 4, it was confirmed that the glucose output increased by stimulation with 100 nM CCDC3 protein (CCDC3 protein 0 nM vs 100 nM, 1.2-fold increase, n=6, p<0.01).

(3) Measurement of Gluconeogenesis System Gene Expression

RNA was prepared from the rat liver cells cultured for 4 hours, using an RNeasy mini kit (QIAGEN) according to the attached manual. cDNA was synthesized from the total RNA (500 ng) using a High Capacity RNA-to-cDNA Kit (Applied Biosystems) according to the attached manual. By using the cDNA as a template, real-time quantitative PCR was performed to examine the mRNA expression amounts of the gluconeogenesis rate-limiting enzymes glucose-6-phosphatase (G6 Pase) and phosphoenolpyruvate carboxykinase (PEPCK). Ribosomal protein S18 (Rps18) was used as a correction gene. Quantification of mRNA amounts was performed by real-time quantitative PCR with SYBR Green I, using rat G6 Pase and rat Rps18 real-time quantitative PCR primers synthesized by Takara Bio.

```
G6Pase:
                                          (SEQ ID NO: 8)
Forward primer: 5'-TGCGTGCCATAGGACTCATCA-3', (SEQ ID NO: 9)
Reverse primer: 5'-AGCAAACAATTGCCCACCGTA-3'

Rps18:
                                         (SEQ ID NO: 10)
Forward primer: 5'-AAGTTTCAGCACATCCTGCGAGTA-3', (SEQ ID NO: 11)
Reverse primer: 5'-TTGGTGAGGTCAATGTCTGCTTTC-3'
```

POWER SYBR GREEN PCR MASTER MIX (Applied Biosystems) was used as the reaction reagent, and the quantification was performed by a reaction at 50° C. for 2 min, and then at 95° C. for 10 min, followed by 40 cycles of reaction at 95° C. for 15 sec and at 60° C. for 60 sec. PCR and fluorescence measurement were performed using 7500 Real time PCR System (Applied Biosystems). For the rat PEPCK, the real-time quantitative PCR was performed using Taqman probe Rn015290092_1 (Applied Biosystems). Taqman Universal PCR Master Mix (Applied Biosystems) was used as the reaction reagent, and the quantification was performed by a reaction at 50° C. for 2 min, and then at 95° C. for 10 min, followed by 40 cycles of reaction at 95° C. for 15 sec and at 60° C. for 1 min. PCR and fluorescence measurement were performed using 7500 Real time PCR System (Applied Biosystems).

Figure 5:
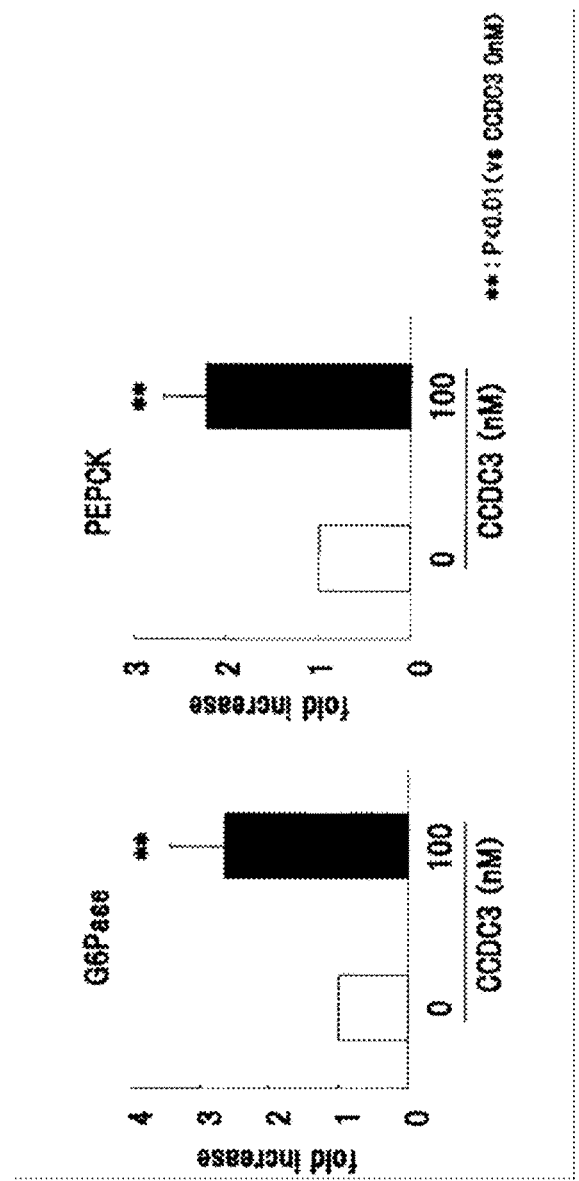
FIG. 5 represents the result of the examination of the influence of 100 nM CCDC3 protein stimulations on gene expression for the gluconeogenesis rate-limiting enzymes glucose-6-phosphatase (G6 Pase) and phosphoenolpyruvate carboxykinase (PEPCK). Significant increases in the mRNA expression of the gluconeogenesis rate-limiting enzymes G6 Pase and PEPCK by 100 nM CCDC3 protein stimulation were confirmed (CCDC3 0 nM vs 100 nM G6 Pase, 2.6-fold increase, PEPCK, 2.2-fold increase, n=5, p<0.01 for each enzyme) (Experiment Example 5(3)).

The results are presented in FIG. 5. As shown in FIG. 5, the analysis results confirmed that stimulation by 100 nM CCDC3 protein significantly increased the mRNA expression of the gluconeogenesis rate-limiting enzymes G6 Pase and PEPCK (CCDC3 protein 0 nM vs 100 nM: 2.6-fold increase in G6 Pase, 2.2-fold increase in PEPCK, n=5, p<0.01 for each enzyme). The results thus suggested that the CCDC3 protein increases liver glucose release by accelerating the gluconeogenesis system.

Example 6

CCDC3 Expression Suppression by Introduced siRNA (1) 3T3-L1 (Mouse Pre-Adipocyte) Culture 3T3-L1 cells (mouse pre-adipocyte) were cultured to confluence in a 10-cm petri dish (Biocoat CollagenI Cellware 100 mm Dish, BD Biosciences), and induced to differentiate in an exchanged differentiation medium D-MEM (+10% FBS, +1% Penicillin G/Streptomycin, 5 μg/ml insulin, 0.5 mM 3-isobutyl-1-methylxanthin, 1 μM dexamethasone). On day 2 of the induced differentiation, the medium was exchanged with D-MEM (+10% FBS, +1% Penicillin G/Streptomycin), and the cells were cultured until day 5 of the induced differentiation.

(2) CCDC3 siRNA Introduction Using Nucleofector (AMAXA)

The differentiated 3T3-L1 cells were detached from the petri dish with trypsin (GIBCO), suspended in D-MEM medium, and collected into a tube. After 5-min centrifugation at 500 rpm, the D-MEM medium was removed, and gently suspended in a Nucleofector Solution (200 μl/100-mm petri dish) attached to Cell Line Nucleofector Kit L (AMAXA). The prepared 100 μl of cell suspension was dispensed in a 1.5-ml tube, and 200 μmol CCDC3 siRNA (QIAGEN, HP GenomeWide siRNA (siRNA #1: sense strand r (gacacaugauacugauaaa)dTdT (SEQ ID NO:5), antisense strand r (uuuaucaguaucauguguc)dTdG (SEQ ID NO:6); siRNA #2: sense strand r (gaaagauguuaagacuuaa)dTdT (SEQ ID NO:7), antisense strand r (uuaagucuuaacaucuuuc)dAdG (SEQ ID NO:8); siRNA #3: sense strand r (gaaguauuugcauaacaaa) dTdT (SEQ ID NO:9), antisense strand r (uuuguuaugcaaauacuuc)dTdA (SEQ ID NO:10)), or control siRNA (QIAGEN, AllStars RNAi Controls) was added. The mixture was gently suspended, and transferred to a cuvette attached to the kit. Note that the CCDC3 siRNAs #1, #2, and #3 are siRNAs that target the 2236-2256, 1506-1526, and 2011-2131 regions, respectively, of the mouse CCDC3 gene base sequence. The cuvette was set on the main unit of Nucleofector, and electroporation was performed. Then, 500 μl of D-MEM (+10% FBS, +1% Penicillin G/Streptomycin) was added to the cuvette, and gently suspended using the attached dropper. The cell suspension was inoculated to the preincubated D-MEM (1.5 ml; +10% FBS, +1% Penicillin G/Streptomycin) on a 6-well plate (Biocoat CollagenI Cellware E-well plate, BD Biosciences), and RNA was prepared after culturing the cells for 2 days.

(3) RNA Preparation and CCDC3 Expression Analysis

RNA was prepared from the CCDC3 siRNA-introduced cells, using an RNeasy mini kit (QIAGEN) according to the attached manual. cDNA was synthesized from the total RNA using a SuperScript First-strand Synthesis System for RT-PCR (Invitrogen) according to the attached manual. By using the cDNA as a template, real-time quantitative PCR was performed to examine the CCDC3 mRNA expression amounts. 36B4 was used as the correction gene. Quantification of mRNA amounts was performed by real-time quantitative PCR with SYBR Green I, using the mouse CCDC3 real-time quantitative PCR primers synthesized by Takara Bio (Forward primer: 5'-TGGTTCATCGCCTCTAATG-GTG-3' (SEQ ID NO:15), Reverse primer: 51-TG-GAATGGGTTCTAGGTGGTCAA-3' (SEQ ID NO:16)), and the mouse 36B4 real-time quantitative PCR primers (Forward primer: 5'-CAACGGCAGCATTTATAACCC-3' (SEQ ID NO:17), Reverse primer: 5'-CCCATTGATGATGGAGT-GTGG-3' (SEQ ID NO:18)). POWER SYBR GREEN PCR MASTER MIX (Applied Biosystems) was used as the reaction reagent, and the quantification was performed by a reaction at 50° C. for 2 min, and then at 95° C. for 10 min, followed by 40 cycles of reaction at 95° C. for 15 sec and at 60° C. for 60 sec. PCR and fluorescence measurement were performed using 7500 Real time PCR System (Applied Biosystems).

Figure 6:
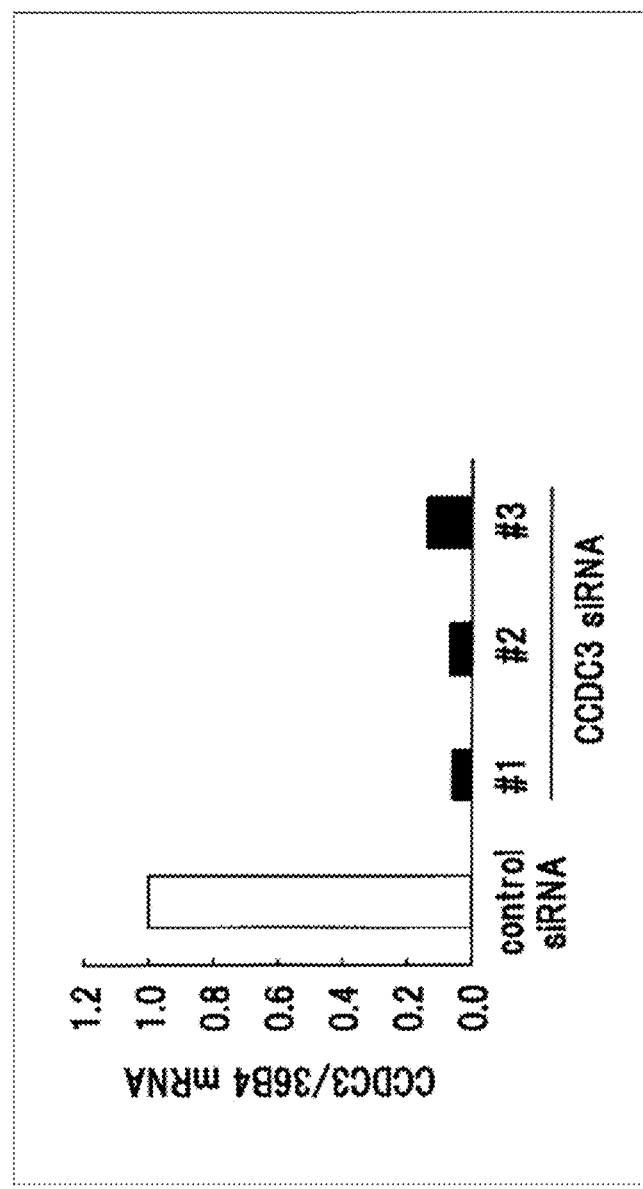
FIG. 6 represents the result of examination concerning suppression of CCDC3 gene (mRNA) expression by the introduction of three CCDC3 siRNAs (QIAGEN, HP GenomeWide siRNA (#1, #2, #3)). CCDC3 gene expression was suppressed by 80% or more by the siRNA introduction (Example 6).

The results are presented in FIG. 6. As shown in FIG. 6, it was confirmed that the introduction of the three types of CCDC3 siRNA suppressed CCDC3 mRNA expression by 80% or more.

Example 7

Production and Analysis of Transgenic (Tg) Mice Using Lentivirus (1) Construction of Plasmid for Producing CCDC3 Lentivirus Vector Total RNA was purified from the adipose tissue collected from wild-type C57BL/6 male mice, using TRIzol Reagent (Invitrogen), and cDNA was synthesized with oligo dT primers using SuperScript III Reverse transcriptase (Invitrogen). By using the cDNA as a template, PCR was performed with specific primers of the base sequences below using KOD FX (Toyobo). As a result, amplification fragments were obtained that had EcoRI and BamHI restriction enzyme sites introduced therein.

```
CCDC3 EcoRI-F3 primer:
                                (SEQ ID NO: 19)
gcgaattctagccgtgcacccagctctccggag CCDC3 BamHI-R3 primer:
                                (SEQ ID NO: 20)
gcggatcctagagcttgcggttgttctcagtcagc
```

The DNA amplification fragments were treated with EcoRI and BamHI restriction enzymes, and inserted and ligated at the EcoRI and BamHI cleavage sites of a pBluescript KS (Stratagene) to obtain a plasmid, which was then sequenced to confirm sequence. By using the plasmid as a template, PCR was performed with specific primers of the base sequences below to obtain a CCDC3 gene ORF sequence that had a kozak consensus sequence and a STOP codon.

```
CCDC3 Kozak-F primer:
                                (SEQ ID NO: 21)
gcgaattccaccatgccgctcccgctgctgctc CCDC3 STOP-R primer:
                                (SEQ ID NO: 22)
gcggatccctacccatgcagatagggggc
```

The DNA amplification fragments were treated with EcoRI and BamHI restriction enzymes, and inserted to the EcoRI and BamHI sites of pCDH1-MCS1 (System Biosciences) to produce a virus producing plasmid pCDH1-CMV-CCDC3. The virus producing plasmid pCDH1-CMV-CCDC3 was sequenced to confirm sequence.

(2) Preparation of CCDC3 Lentivirus Vector

293FT cells (Invitrogen) were cultured under 5% $CO_2$ 37° C. conditions using DMEM (high glucose) that contained 10% FCS (fetal bovine serum). The cells were transfected using FuGENE6 (Roche) according to the attached protocol, and the pCDH1-CMV-CCDC3 plasmid was introduced together with the packaging plasmids (pPACKH1-GAG, pPACKH1-REV, pVSV-G) of the pPACKH1 Lentivector Packaging Kit (System Biosciences). After 72 hours from the transfection, the culture supernatant was collected, filtered through a 0.45-μm filter (Millipore), and concentrated by ultracentrifugation (Beckman SW32Ti rotor; 19,400 rpm, 4° C., 2 hours). The supernatant was carefully discarded, and suspended in PBS. This was followed by purification using a sucrose density gradient method (Beckman SW55Ti rotor; 21,000 rpm, 4° C., 2 hours), and finally by suspension in PBS to prepare a concentrated lentivirus vector for transgenic mice production. The physical titer (number of particles) of the virus vector was measured using a p24 Antigen ELISA kit (ZeptoMetrix).

(3) Production of Transgenic Mice Using Lentivirus Vector

BDF1 female mice were administered with 51 U of PMSG (pregnant mare serum gonadotropin), and, 48 hours later, intraperitoneally with 51 U of hCG (chorionic gonadotrophin) using an ordinary method to induce multiple ovulation. The mice were then crossed with BDF1 male mice. On the next day of the crossing, the oviduct of a female mouse with a confirmed vaginal plug was collected after about 40 hours from the crossing, and perfused with 0.4% BSA-containing physiological saline. The collected two-cell embryo was cultured briefly in a KSOM medium (Ark Resource), and treated with acidic Tyrode (Ark Resource) for about 1 to 2 min to melt and remove the embryo transparent body. The embryo with successfully removed zona pellucida was washed in a KSOM medium, and cultured in the same medium until virus infection. The embryo after the removal of zona pellucida was virally infected by being cultured for 2 days with drops (6 μl/spot) of KSOM medium diluted to contain about 100 pg/μl, 333 pg/μl, or 1,000 pg/μl of virus particles. All embryos were cultured under 5% $CO_2$ 37° C. conditions. Following the virus infection, the embryo developed to the blastocyst or morula stage was transplanted into the uterus of a pseudopregnant mouse 2.5 days after checking the vaginal plug. After 17 days from the transplant, baby mice were obtained by natural birth or Caesarean section.

(4) Screening of CCDC3 Transgenic Mice

Genomic DNA was purified from the tail end of the baby mice collected after 3 weeks from birth, using a DNeasy Blood & Tissue Kit (QIAGEN). By using the purified DNA as a template, PCR was performed with the primer set of the following base sequences for genotyping.

```
                                            (SEQ ID NO: 23)
CCDC3-F1 primer: ggagagggagggctcttcta (SEQ ID NO: 24)
CCDC3-R1 primer: gttctcctgggtgtctggaa
```

Total RNA was purified from the tail end of the transgenic mice screened by PCR after 4 to 5 weeks from birth, using an RNeasy Plus Mini Kit (QIAGEN). By using the purified RNA as a template, CCDC3 gene expression analysis was performed with the primer set of the base sequences below, using a Quantitect SYBR Green RT-PCR Kit (QIAGEN). mGAPDH gene was used as an endogenous control gene in the expression analysis, and transgenic mice (CCDC3 Tg mice) with the CCDC3 gene expression amount four times or greater than that in the control group were screened for phenotyping.

```
                                            (SEQ ID NO: 25)
CCDC3-Q PCR-F primer: gctcaaccttactggtctgggcta (SEQ ID NO: 26)
CCDC3-Q PCR-R primer: catcttggaaattgactccgtgtg (SEQ ID NO: 27)
mGAPDH-Q PCR-F primer: aaatggtgaaggtcggtgtg (SEQ ID NO: 28)
mGAPDH-Q PCR-R primer: tgaaggggtcgttgatgg
```

(5) Phenotyping of CCDC3 Transgenic Mice

CCDC3 Tg mice and a virus infection control group, 8 weeks old, were given the high-fat diet (HFD) 58Y1 DIO P.D. 60% Energy From Fat-Blue (Japan SLC), and the body weights were measured over time (FIG. 7). On day 52 post HFD feeding, casual glucose levels were measured (FIG. 8). The casual glucose levels were measured with a Glucocard DIA meter α (Arkray), using trace amounts of blood collected by cutting the tail vein with a razor. For the virus infection control group, a lentivirus vector was used produced in the same manner as for the pCDH1-CMV-CCDC3, using a pCDH1-CMV-loxP-stop-loxP-EGFP plasmid.

The analysis confirmed increased body weights in the HFD CCDC3 Tg mice over the control group, as shown in FIG. 7. Further, as shown in FIG. 8, the CCDC3 Tg mice had increased casual glucose levels over the control group, as measured on day 52 post HFD feeding. These results suggested the possibility that CCDC3 has the effect to influence body weight and glucose level.

Example 8

Preparation of Monoclonal Antibodies that Recognize Human CCDC3 Protein

Human CCDC3 monoclonal antibodies were prepared as antibodies that recognize CCDC3, according to the method described in Immunochemistry in Practice (Blackwell Scientific Publications).

(1) Selection of Antigens

In order to acquire CCDC3-recognizing antibodies, the human recombinant CCDC3 prepared in the foregoing Examples, and its conjugates with KLH (keyhole limpet hemocyanin) were used as immunogens. Because the steric structure of human CCDC3 has not been elucidated, the C-terminus peptide of the amino acid sequence from position 259 to 270 of human CCDC3, having a high possibility of being exposed on the surface of the steric structure was selected as the immunogen.

(2) Immunogen Preparation

A human CCDC3 protein C-terminus partial peptide (259-270, 12 amino acid residues, ARGPVRPPYLRG: SEQ ID NO:29) was synthesized, and a sulfo-SMCC aqueous solution with 10 times the molar quantity was added to a 0.1 M phosphate buffer (pH 7.1) that contained 1.5 mg of the partial peptide. This was followed by reversed-phase HPLC (column: YMC-pack ODS-A, 6.0×150 mm, mobile phase: acetonitrile/0.1% trifluoroacetate aqueous solution) to separate 1.4 mg of a maleimidized peptide fraction. The maleimidized peptide fraction was freeze dried, and used in the conjugation described below. Separately, a Sulfo-SPDP (Thermo scientific) aqueous solution with 700 times the molar quantity was added to 2 mL of 0.1 M phosphate buffered saline (pH 7.2) that contained 20 mg of mariculture keyhole limpet hemocyanin (KLH, Thermo scientific). The mixture was left unattended at 4° C. for 16 hours, and then at room temperature for 30 min after adding 0.2 mL of a 0.1 M mercaptoethylamine aqueous solution. This was followed by gel filtration to separate SH group-introduced KLH, using a PD-10 column (GE Healthcare) equilibrated with 5 mM EDTA-containing 0.1 M phosphate buffer (pH 6.0). A freeze-dried powder (1.2 mg) of the maleimidized C-terminus peptide was added to the 5 mM EDTA-containing 0.1 M phosphate buffer (pH 6.0) that contained the SH group-introduced KLH (10 mg), and the mixture was allowed to react at room temperature for 1 hour, and at 4° C. overnight. The reaction mixture was dialyzed against purified water, freeze dried, and used as the immunogen (antigen 1).

Separately, a Sulfo-EMCS (Thermo scientific) was added to the human recombinant CCDC3 (1.1 mg) purified in Example 4 at a molar ratio of 5:1, and the mixture was allowed to react at room temperature for 3 hours to prepare maleimide human CCDC3. Then, 3.75 μM sulfo-LC-SPDS (Thermo scientific) was added to 20 mg of mariculture keyhole limpet hemocyanin (KLH, Thermo scientific). The mixture was allowed to react at room temperature for 3 hours to prepare a SH group-introduced KLH. The maleimide human CCDC3 (1 mg) and the SH group-introduced KLH (8 mg) were mixed, and reacted at 4° C. overnight. The reaction mixture was dialyzed against 10 mM PB (pH 7.5) and 0.5 M NaCl, preserved at −80° C., and used as the immunogen (antigen 2).

The three immunogens, including the two immunogens prepared above and the human recombinant CCDC3 (antigen3), were intraperitoneally administered (100 μg each) to Balb/c female mice, 4 weeks old, with a Freund's complete adjuvant (initial immunization). After 21, 42, 63, and 84 days, the immunogen (100 μg) was administered with a Freund's incomplete adjuvant for boosting. After 104 days, the immunogen (100 μg) suspended in 10 mM PB (pH 7.5) and 0.5 M NaCl (0.1 mL) was intraperitoneally administered for final immunization.

(3) Hybridoma Production

Spleen was removed after 3 days from the final immunization, and spleen cells were collected. The spleen cells were fused with mouse myeloma cells (p3×63-Ag8.U1, Tokyo Shuryu Kenkyusho) using 50% polyethyleneglycol 4000, and selected in a medium that contained hypoxanthine, aminopterin, and thymidine.

(4) Biotin Labeling of Peptide in Human CCDC3 Protein C-Terminus Region

An aqueous solution (32 μl) containing an equimolar (160 μg) PEO-maleimide activated biotin (PIERCE) was added to 5 mM EDTA-containing 0.1 M phosphate buffer (pH 6.0) that contained a 13 mer peptide (0.4 mg) obtained by adding a Cys residue to the N-terminus of the peptide (259-270, 12 amino acid residues) in the C-terminus region of human CCDC3 protein. The mixture was left unattended at room temperature for 2 hours, and the peptide of the biotin-labeled human CCDC3 protein C-terminus region was purified by reversed-phase HPLC (column: YMC-pack ODS-A, 6.0×150 mm, mobile phase: acetonitrile/0.1% trifluoroacetate aqueous solution).

(5) Biotin labeling of Recombinant Human CCDC3 Protein

Human recombinant CCDC3 protein (0.31 mg) dissolved in 0.31 ml of 10 mM phosphate buffer (pH 7.2), 0.5 M NaCl, and 0.01% Tween 20 was added to 4.1 μl of a 20 mM PEO-maleimide activated biotin (PIERCE) aqueous solution, and the mixture was allowed to react at 4° C. overnight. This was followed by gel filtration using a Superdex 75 (GE Healthcare Biosciences) equilibrated with 10 mM phosphate buffer (pH 7.2) and 0.5 M NaCl to purify the labeled human CCDC3.

(6) Selection of Human CCDC3 Monoclonal Antibodies

Specific antibody producing cells were screened 10 days after the cells were fused. Screening was performed by ELISA, as follows. A Tris buffer (50 mM Tris-HCl, pH 7.5, 35 μl) containing anti-mouse IgG antibodies (0.35 μg; Shibayagi Co., Ltd.) was added to each well of a 384-well microtiter plate (Nunc), and the antibodies were immobilized at 4° C. for 16 hours. The wells were washed once with 90 μl of washing liquid (physiological saline containing 0.01% Tween 20), and left unattended at room temperature for 2 hours for blocking after adding 200 μl of Block Ace (Dainippon Pharma) (anti-mouse IgG antibody-anchored plate). After washing each well once with washing liquid (90 μl), a hybridoma culture supernatant (15 μl) and buffer A (10 μl; 50 mM Tris buffer containing 0.5% bovine serum albumin, 0.01% Tween 80, 0.05% Proclin 150, and 0.5 M NaCl; pH 7.4) were added. When the immunogen was the peptide-KLH conjugate, buffer A (10 μl) containing 0.02 ng of the biotin-human CCDC3 protein C-terminus region peptide and 2 ng of Streptavidin-HRP (PIERCE) was added. When the immunogen was the human recombinant CCDC3 protein or its KLH-conjugate, buffer A (10 μl) containing 1 ng of the biotin-human recombinant CCDC3 protein and 4 ng of Streptavidin-HRP (PIERCE) was added. In either case, reaction was performed at 4° C. for 16 hours. After washing each well three times with washing liquid (90 μl), 25 μl of TMB+Substrate-Chromogen (DAKO) was added to develop color at room temperature for 30 min. The reaction was stopped by adding 25 μl of 0.5 M sulfuric acid, and absorbance at 450 nm was measured.

After the screening, three clones (3H6, 6G12, 11E10) with strong affinity to the human recombinant CCDC3 protein were obtained. Note that the 3H6, 6G12, and 11E10 antibodies were obtained from the mouse-derived hybridomas immunized with antigen 1, antigen 3, and antigen 2, respectively. The subclass of each antibody was determined using a mouse monoclonal antibody isotyping ELISA kit (BD biosciences). The antibodies 3H6 and 11E10 were of isotype IgG2b, and the antibody 6G12 was of IgG1.

(7) Antibody Affinity Evaluation by ELISA

Figure 9:
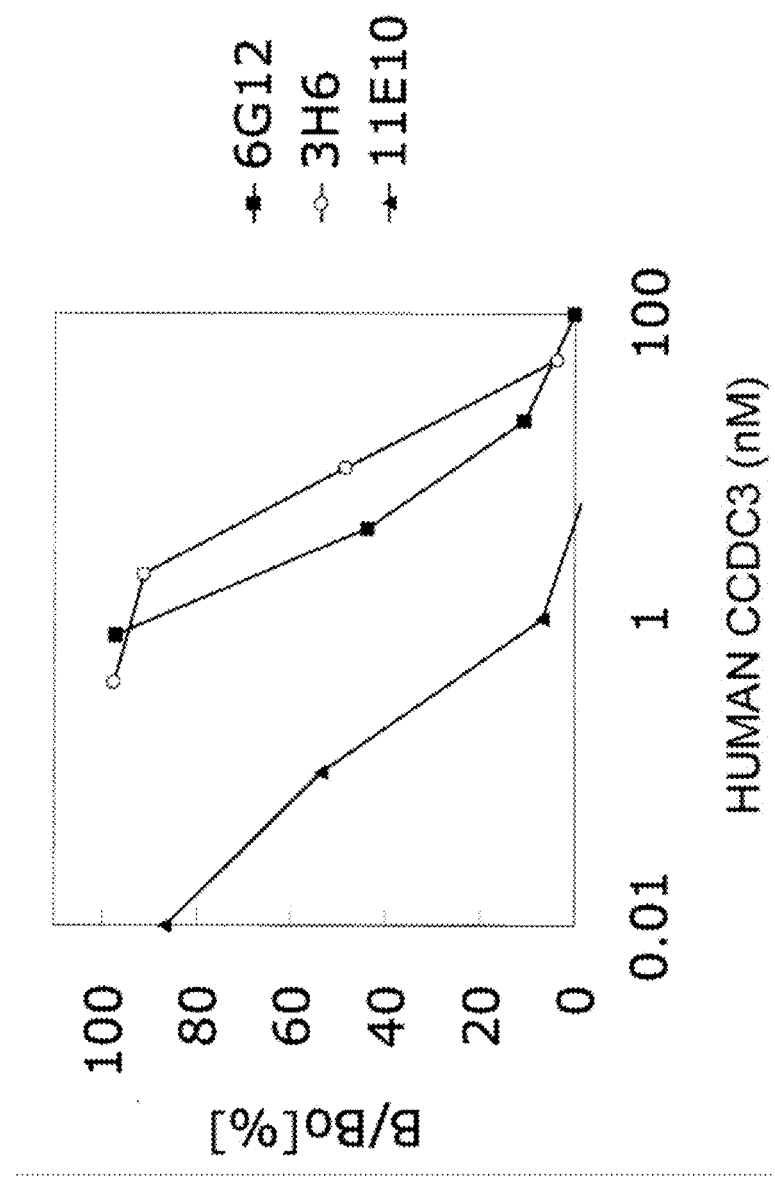
FIG. 9 represents human recombinant CCDC3 protein displacement curves for the binding of human anti-CCDC3 antibodies (6G12, 3H6, 11E10) to biotin-labeled human recombinant CCDC3 protein (Example 8).

A buffer A containing 10 μl of CCDC3 antibody was added to the anti-mouse IgG antibody-anchored plate, and 10 μl of 0.01 to 100 nM human recombinant CCDC3 was added. The mixture was allowed to react at 4° C. for 16 hours after adding buffer A (10 μl) that contained 1 ng of biotin-human recombinant CCDC3 protein and 4 ng of Streptavidin-HRP (PIERCE). Each well was washed three times with washing liquid (90 μl), and 25 μl of TMB+Substrate-Chromogen (DAKO) was added to develop color at room temperature for 30 min. The reaction was stopped by adding 25 μl of 0.5 M sulfuric acid, and absorbance at 450 nm was measured. The results are presented in FIG. 9.

As can be seen from the results, the $IC_{50}$ values of the antibodies against human CCDC3 protein were 9.4 nM, 3.2 nM, and 0.10 nM for the 3H6, 6G12, and 11E10 antibodies, respectively.

Example 9

Evaluation of Antibody Binding to Human CCDC3 Protein by Western Blotting

Figure 10:
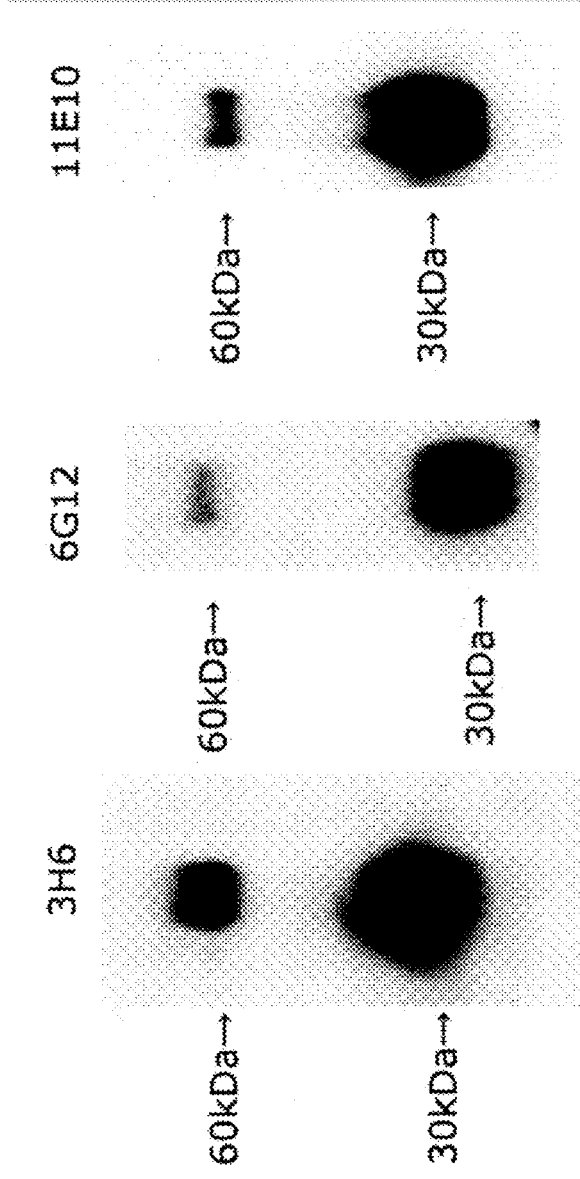
FIG. 10 is the result of western blotting representing the reactivity of human anti-CCDC3 antibodies (6G12, 3H6, 11E10) to human recombinant CCDC3 protein (Example 9). The proteins at 30 kDa and 60 kDa apparently correspond to the monomer and dimer, respectively, of the CCDC3 protein from the deduced molecular weight of the CCDC3 protein (also in FIG. 12).

Western blotting was performed using the 3H6, 6G12, and 11E10 antibodies. Human recombinant CCDC3 protein (50 ng) was subjected to SDS-PAGE (reduced state). For detection, anti-mouse IgG-HRP antibodies (GE Healthcare Biosciences) and ECL advance (GE Healthcare Biosciences) were used. The results are presented in FIG. 10. The results revealed that the all antibodies were positive in western blotting, and bound to the human recombinant CCDC3 protein.

Example 10

Determination of Antibody Sequence

The sequences of the heavy-chain variable domain and light-chain variable domain of the 3H6, 6G12, and 11E10 antibodies obtained in Example 8 were determined using an ordinary method.

(1) 3H6 Antibody

```
Heavy-chain variable domain
                                                      (SEQ ID NO: 30)
QIQLVQSGPELKKPGETVKISCKASGYTFTNYGMIWVKQAPGKDLKWMAWINTYSGEPTCADDFK

GRFAFSLETSASTAYLQINNLKNEDMATYFCARDDGYYGYFDYWGQGTTLTVSS
```

Note that the underlined regions in the heavy-chain variable domain correspond to CDR1 (SEQ ID NO:31), CDR2 (SEQ ID NO:32), and CDR3 (SEQ ID NO:33) from the N-terminus side (left).

```
Light-chain variable domain
                                                      (SEQ ID NO: 34)
DVVMTQTPLSLPVSLGDQASISCRSSQTLVHSDWTYLHWYLQKPGQSPKLLIYKISNRFSGVPD

RFSGSGSGTDFTLKISRVEAEDLGVYFCSQSTHVPPTFGGGTKLEIKRA
```

Note that the underlined regions in the light-chain variable domain correspond to CDR1 (SEQ ID NO:35), CDR2 (SEQ ID NO:36), and CDR3 (SEQ ID NO:37) from the N-terminus side (left).

(2) 6G12 Antibody

```
Heavy-chain variable domain
                                                      (SEQ ID NO: 38)
QVQLQQPGAELVRPGASVKMSOKASGYTFSSYLMDWVKQRPGQGFECIGNINPNTGSTIINERFK

GKAKLTVDKSSTAYMQLISLTSEDSAVYYCAADGYYAPFTYWGQGTLVTVSA
```

Note that the underlined regions in the heavy-chain variable domain correspond to CDR1 (SEQ ID NO:39), CDR2 (SEQ ID NO:40), and CDR3 (SEQ ID NO:41) from the N-terminus side (left).

```
Light-chain variable domain
                                                      (SEQ ID NO: 42)
DIVMTQAAPSVPVTPGESVSISCRSSKSLLHNNGNTYLYWFLQRPGQSPQLLIYRMSNLASGVPD

RFSGSGSGTAFTLRISRVEAEDVGVYYCMQHLEYPFTFGAGTKLELKRA
```

Note that the underlined regions in the light-chain variable domain correspond to CDR1 (SEQ ID NO:43), CDR2 (SEQ ID NO:44), and CDR3 (SEQ ID NO:45) from the N-terminus side (left).

(3) 11E10 Antibody

```
Heavy-chain variable domain
                                                      (SEQ ID NO: 46)
QVQLQQSGPELVKPGASVKISCKASGYSFRSYYIHWMKQSPGQGLEWIAWIYPGGGKIYYNDNEK

FKDKVTLTADTSSSTAYMQLTGLTSEDSAVYFCARWGGYYVGSILDYWGQGTSVTVSS
```

Note that the underlined regions in the heavy-chain variable domain correspond to CDR1 (SEQ ID NO:47), CDR2 (SEQ ID NO:48), and CDR3 (SEQ ID NO:49) from the N-terminus side.

```
Light-chain variable domain
                                                      (SEQ ID NO: 50)
DGDIVMTQSQKFLSTSVGDRVSVTCKASQNVDNNVAWYQQRPGQSPKPLIYLTSSRYSGVPDRFT

GSGSGTDFILTITNVQSEDLAEYFCQQYKTYPLTFSVGIKLELKRA
```

Note that the underlined regions in the light-chain variable domain correspond to CDR1 (SEQ ID NO:51), CDR2 (SEQ ID NO:52), and CDR3 (SEQ ID NO:53) from the N-terminus side (left).

Example 11

Preparation of Antibodies that Recognize Mouse CCDC3 Protein (1) Selection of Antigens A KLH conjugate of mouse recombinant CCDC3 protein prepared in the same manner as for the human recombinant CCDC3 protein prepared above was used as the immunogen. The peptide in the C-terminus region with the amino acid sequence from position 262 to 273 of mouse CCDC3 was selected as the immunogen.

(2) Immunogen Preparation

A peptide (13 amino acids) with a cysteine introduced to the C-terminus of the peptide (positions 262 to 273) in the C-terminus region of mouse CCDC3 protein was synthesized (Scrum Inc.). The synthetic peptide (2.9 mg) was dissolved in a 0.1 M phosphate buffer (PH 6.0) that contained 5 mM EDTA (0.29 mL), and an aqueous solution (1 mL) containing 10 mg of Inject Maleimide activated mariculture keyhole limpet hemocyanin (Thermo scientific) was added. The mixture was then allowed to react at room temperature for 1 hour, and then at 4° C. overnight. The reaction mixture was dialyzed against purified water, freeze dried, and used as the immunogen.

Separately, Sulfo-EMCS (Thermo scientific) was added at a molar ratio of 5:1 to 1.1 mg of mouse recombinant CCDC3 purified in the same manner as for the human CCDC3 protein. The mixture was allowed to react at room temperature for 3 hours to prepare maleimide mouse CCDC3. Then, 3.75 µM sulfo-LC-SPDS (Thermo scientific) was added to 20 mg of mariculture keyhole limpet hemocyanin (Thermo scientific), and reacted at room temperature for 3 hours to prepare SH group-introduced KLH. The maleimide mouse CCDC3 (1 mg) and the SH group-introduced KLH (8 mg) were mixed, and reacted at 4° C. overnight. The reaction mixture was dialyzed against 10 mM PB (PH 7.5) and 0.15 M NaCl, preserved at −80° C., and used as the immunogen.

The two immunogens prepared as above (100 µg each) were intraperitoneally administered to Balb/c female mice, 4 weeks old, together with a Freund's complete adjuvant (initial immunization). After 21, 42, 63, and 84 days, the immunogen (100 µg) was administered with a Freund's incomplete adjuvant for boosting. After 104 days, the immunogen (100 µg) suspended in physiological saline (0.1 mL) was intraperitoneally administered for final immunization.

(3) Hybridoma Production

Spleen was removed after 3 days from the final immunization, and spleen cells were collected. The spleen cells were fused with mouse myeloma cells (p3×63-Ag8.U1, Tokyo Shuryu Kenkyusho) using 50% polyethyleneglycol 4000, and selected in a medium that contained hypoxanthine, aminopterin, and thymidine.

(4) Biotin Labeling of Partial Peptide in Mouse CCDC3 Protein C-Terminus Region

An aqueous solution (40 µl) containing an equimolar (200 µg) PEO-maleimide activated biotin (PIERCE) Was added to 5 mM EDTA-containing 0.1 M phosphate buffer (pH 6.0) that contained a peptide (13 amino acids; 0.5 mg) obtained by introducing a Cys residue to the C-terminus of the partial peptide (amino acid sequence from position 262 to 273) in the C-terminus region of mouse CCDC3 protein. The mixture was left unattended at room temperature for 2 hours, and the partial peptide of the biotin-labeled mouse CCDC3 protein C-terminus region was purified by reversed-phase HPLC (column: YMC-pack ODS-A, 6.0×150 mm, mobile phase: acetonitrile/0.1% trifluoroacetate aqueous solution).

(5) Biotin Labeling of Mouse Recombinant CCDC3 Protein

Mouse recombinant CCDC3 protein (0.22 mg) dissolved in 0.20 ml of 10 mM phosphate buffer (pH 7.2), 0.5 M NaCl, and 0.01% Tween 20 was added to 3.2 µl of a 20 mM PEO-maleimide activated biotin (PIERCE) aqueous solution, and the mixture was allowed to react at 4° C. overnight. This was followed by gel filtration using a Superdex 75 (GE Healthcare Biosciences) equilibrated with 10 mM phosphate buffer (pH 7.2) and 0.5 M NaCl to purify the labeled mouse CCDC3.

(6) Selection of Anti-CCCD3 Antibodies

Specific antibody producing cells were screened 10 days after the cells were fused. Screening was performed by ELISA, as follows. A Tris buffer (50 mM Tris-HCl, pH 7.5, 35 µl) containing anti-mouse IgG antibodies (0.35 µg; Shibayagi Co., Ltd.) was added to each well of a 384-well microtiter plate (Nunc), and the antibodies were immobilized at 4° C. for 16 hours. The wells were washed once with 90 µl of washing liquid (physiological saline containing 0.01% Tween 20), and left unattended at room temperature for 2 hours for blocking after adding 200 µl of Block Ace (Dainippon Pharma) (anti-mouse IgG antibody-anchored plate). After washing each well once with washing liquid (90 µl), a hybridoma culture supernatant (15 µl) and buffer B (10 µl; 50 mM Tris buffer containing 0.5% bovine serum albumin, 0.01% Tween 80, 0.05% Proclin 150, and 0.15 M NaCl; pH 7.4) were added. When the immunogen was the peptide-KLH conjugate, buffer B (10 µl) containing 0.02 ng of the biotin-mouse CCDC3 protein C-terminus region partial peptide and 2 ng of Streptavidin-HRP (PIERCE) was added. When the immunogen was the mouse recombinant CCDC3 protein-KLH-conjugate, buffer B (10 µl) containing 1 ng of the biotin-mouse recombinant CCDC3 protein and 4 ng of Streptavidin-HRP (PIERCE) was added. In either case, reaction was performed at 4° C. for 16 hours. After washing each well three times with washing liquid (90 µl), 25 µl of TMB+Substrate-Chromogen (DAKO) was added to develop color at room temperature for 30 min. The reaction was stopped by adding 25 µl of 0.05 M sulfuric acid, and absorbance at 450 nm was measured.

After the screening, clones (13A8, 24F6) with strong affinity to the mouse recombinant CCDC3 protein were obtained. The subclass of each antibody was determined using a mouse monoclonal antibody isotyping ELISA kit (BD biosciences). The antibodies 13A8, 13D4, and 24F6 were of IgG1, IgG2a, and IgM, respectively.

(7) Antibody Affinity Evaluation by ELISA

Figure 11:
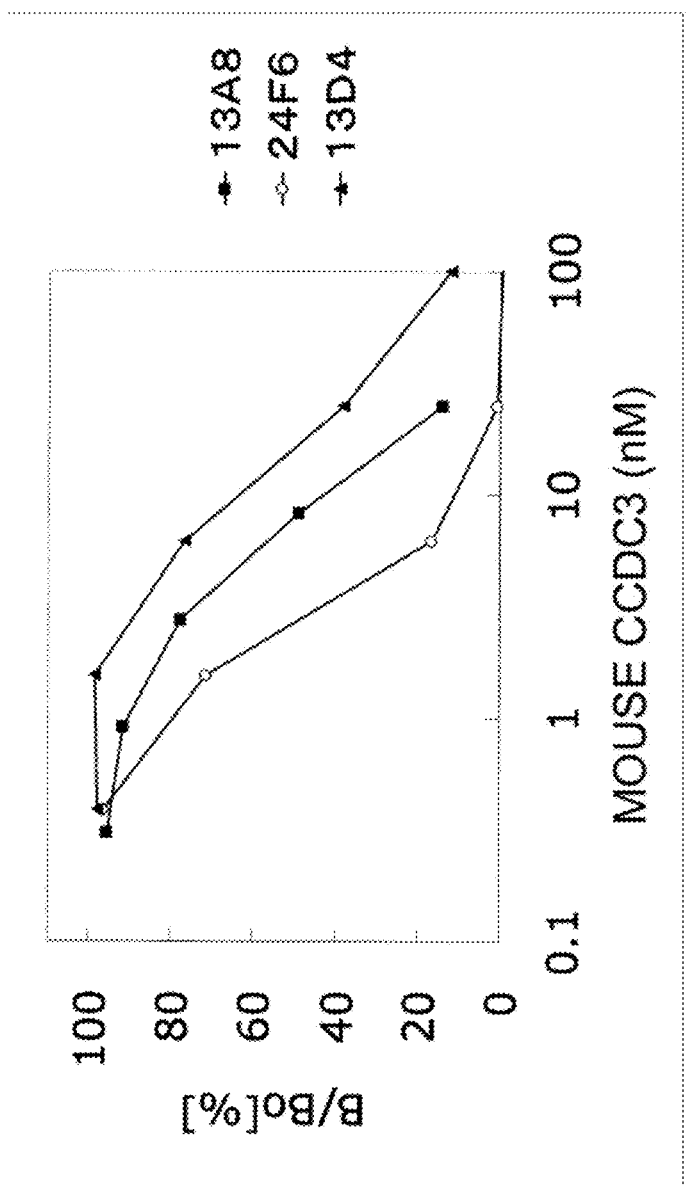
FIG. 11 represents mouse recombinant CCDC3 protein displacement curves for the binding of mouse anti-CCDC3 antibodies (13A8, 13D4, 24F6) to immunogen peptide or biotin: labeled mouse recombinant CCDC3 protein (Example 11).

A buffer A containing 10 µl of the selected anti-CCDC3 antibody was added to the anti-mouse IgG antibody-anchored plate, and 10 µl of 0.01 to 100 nM mouse recombinant CCDC3 protein was added. For the 13A8 antibody, a buffer B (10 µl) containing 1 ng of the C-terminus region partial peptide of biotin-mouse recombinant CCDC3 protein and 4 ng of Streptavidin-HRP (PIERCE) was added. For the 13D4 and 24F6 antibodies, a buffer B (10 µl) containing 0.02 ng of the biotin-mouse recombinant CCDC3 protein and 2 ng of Streptavidin-HRP (PIERCE) was added. Each was allowed to react at 4° C. for 16 hours. Each well was washed three times with washing liquid (90 µl), and 25 µl of TMB+Substrate-Chromogen (DAKO) was added to develop color at room temperature for 30 min. The reaction was stopped by adding 25 µl of 0.05 M sulfuric acid, and absorbance at 450 nm was measured. The results are presented in FIG. 11. As can be seen from the figure, the $IC_{50}$ values of the antibodies against the mouse CCDC3 protein were 7.4 nM, 17 nM, and 2.6 nM for the 13A8, 13D4, and 24F6 antibodies, respectively.

Example 12

Evaluation of Antibody Binding to Mouse CCDC3 Protein by Western Blotting

Figure 12:
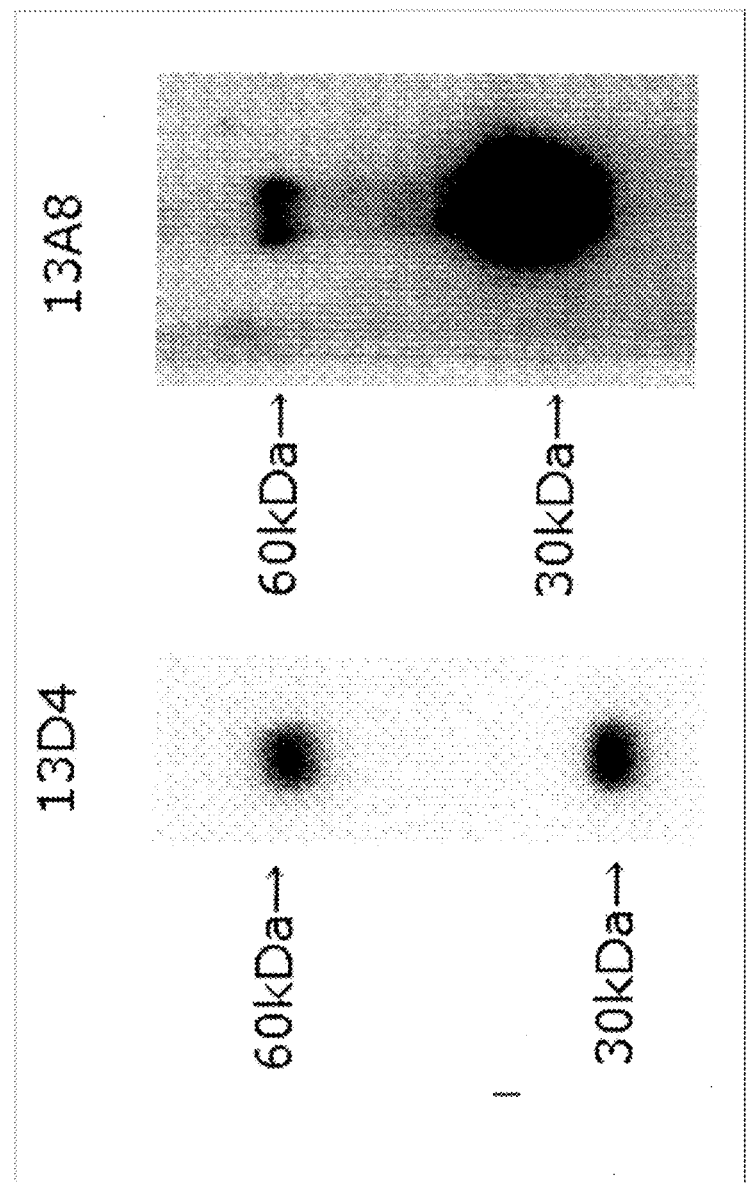
FIG. 12 is the result of western blotting representing the reactivity of mouse anti-CCDC3 antibodies (13A8, 13D4) to mouse recombinant CCDC3 protein (Example 12).

Western blotting was performed using the 13A8 antibodies. Mouse recombinant CCDC3 protein (50 ng) was subjected to SDS-PAGE (reduced state). For detection, anti-mouse IgG-HRP antibodies (GE Healthcare Biosciences) and ECL advance (GE Healthcare Biosciences) were used. The results are presented in FIG. 12. The results revealed that the all antibodies were positive in western blotting, and bound to the mouse recombinant CCDC3 protein (FIG. 12).

Example 13

Setting CCDC3 Concentration Measurement Method by Chemiluminescence Detection Sandwich ELISA in Human Blood Plasma Two sandwich ELISA methods were set using 6G12 antibodies against human CCDC3 protein, and 3H6 antibodies against the human CCDC3 protein C-terminus partial peptide (anchored antibodies), and using 11E10 antibodies against human CCDC3 protein (detection antibodies).
(1) Preparation of Biotin Labeled 6G12 and 3H6

The IgG fraction of the 6G12 or 3H6 antibodies was reacted with NHS-PEO-biotin (PIERCE) at a molar ratio of 1:10 in 0.1 M phosphate buffer. This was followed by gel filtration performed with a PD-10 column (GE Healthcare) equilibrated with 50 mM tris-HCL buffer (pH 7.5) to separate the biotinylated 6G12 or 3H6 fraction. In the sandwich ELISA, the biotinylated 6G12 or 3H6 antibodies were used by being immobilized on a 96-well microtiter plate that had been coated with goat anti-biotin antibodies.
(2) Preparation of Alkaliphosphatase-Labeled 11E10 Fab' Antibodies The detection antibodies were obtained by labeling the 11E10 antibody Fab' fraction with alkaliphosphatase (ALP, Roche, recombinant), and were prepared according to the following procedure. Pepsin (Roche, derived from pig gastric mucosa) was added to a 0.1 M sodium acetate buffer (pH 4.2) that contained the IgG fraction of the 11E10 antibodies (added in 40 µg per milligram of IgG1), and incubated at 37° C. for 16 hours. This was followed by high speed gel filtration (LC-6A system (Shimadzu Corporation) equipped with a TSK-GEL G3000 column (Tosoh) equilibrated with 5 mM EDTA-containing 0.1 M phosphate buffer, pH 6.0) to separate the F(ab')$_2$ fraction. Then, a 0.1 M mercaptoethylamine aqueous solution was added to the F(ab')$_2$ fraction in $\frac{1}{10}$ the volume of the F(ab')$_2$ solution. The mixture was allowed to react at 37° C. for 1.5 hours, and the Fab' fraction was separated by high speed gel filtration. Separately, sulfo-SMCC (PIERCE) was added to 0.2 mL of a 0.05 M borate buffer (pH 7.6, containing 1 mM MgCl$_2$ and 0.1 mM ZnCl$_2$ with ALP) in 5 times the molar quantity of ALP, and reacted at 30° C. for 30 min. This was followed by gel filtration with a PD-10 column (GE Healthcare) equilibrated with a 1.0 mM MgCl$_2$- and 0.1 mM ZnCl$_2$-containing 0.1 M tris-HCL buffer (pH 6.8) to collect the maleimidized ALP fraction. The maleimidized ALP fraction and the 11E10 Fab' fraction were mixed at a molar ratio of 1:3, and allowed to react at 4° C. overnight. This was followed by high speed gel filtration to separate the target ALP-labeled 11E10 Fab' fraction.

(3) Chemiluminescence Detection Sandwich ELISA

As a standard substance, the human recombinant CCDC3 protein was used by being diluted with buffer A (50 mM Tris buffer containing 1.0% bovine serum albumin, 0.1% Tween 80, 0.05% sodium azide, 0.5 M NaCl, 1 mM MgCl$_2$, and 0.1 mM ZnCl$_2$, pH 7.5°). A Tris buffer (50 mM Tris-HCl, pH 7.5, 100 µL) containing goat anti-biotin antibodies (1.0 µg; Bethyl) was added to each well of a 96-well white microtiter plate (NUNC, Maxi-Sorp), and the mixture was left unattended at 4° C. for 16 hours to immobilize the antibodies. The wells were washed once with 250 µL of washing liquid (physiological saline containing 0.01% Tween 20), and left unattended at room temperature for 2 hours for blocking after adding 150 µL of Block Ace (Dainippon Pharma). After washing each well once with 250 µL of washing liquid, a buffer A containing 100 ng of the biotinylated 6G12 antibodies or 3H6 antibodies was added, and the mixture was left unattended at room temperature for 1 to 2 hours. After washing each well three times with washing liquid, a 1 to 500 µM standard human recombinant CCDC3 protein solution or a biological solution sample (50 µL) and buffer A (50 µL) were added and mixed. The mixture was left unattended at 4° C. for 16 to 24 hours. After washing each well three times with washing liquid, a buffer A (100 µL) containing 10 ng of the ALP-labeled 11E10 Fab' fraction was added, and the mixture was left unattended at room temperature for 2 to 3 hours. After washing each well three times with washing liquid, a luminescent substrate CDP-Star®/Emerald II (100 µL; Applied Biosystems) was added, and the mixture was left unattended at room temperature. After 20 minutes from adding the substrate, luminescence intensity was measured with a multilabel counter ARVO® (PerkinElmer).

Figure 13:
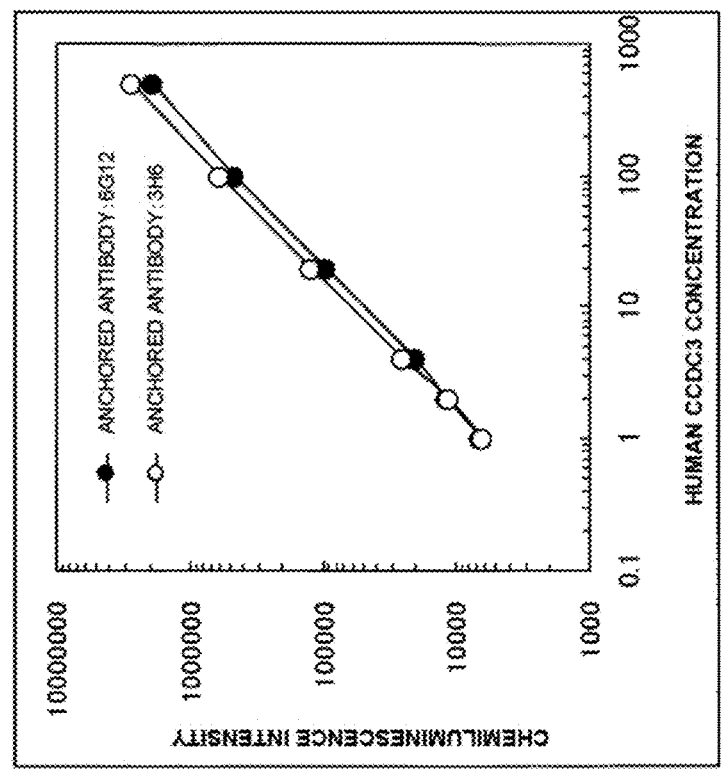
FIG. 13 represents standard curves in the CCDC3 protein immunoassay using two combinations of human anti-CCDC3 antibodies (6G12-11E10, 3H6-11E10) (Example 13).

As a result, a desirable standard curve was obtained in the standard human CCDC3 protein in the 1 to 500 pM range, with the minimum detection limit of 1 pM, as shown in FIG. 13. It is therefore possible to specifically and sensitively measure the CCDC3 protein in a human biological solution such as a human blood plasma sample.

Example 14

Analysis of Correlation between CCDC3 Concentration and the Extent of Obesity in Human Blood Plasma (1) Preparation of Human Blood Plasma Blood was collected from 85 donors after obtaining consent for the experiment.

In all blood samples, hemoglobin A1c (HbA1c) was also measured during the measurement of CCDC3 protein concentration in the blood plasma. The collected blood was transferred to a blood plasma separation tube (EDTA.2Na blood collection tube), and centrifuged at 3,000 rpm for 30 min at 4° C. The supernatant was then used as blood plasma for testing.

The measurement of CCDC3 protein concentration in the blood plasma was performed using ELISA with a combination of 3H6 and 11E10 antibodies, according to the chemiluminescence detection sandwich ELISA method described in Example 13(3).

25 out of the 85 subjects were also measured for the visceral fat area (visceral fat area in the abdominal cross section at navel), using CT (computed tomography). Among the 25 subjects, eight classified as non-visceral obesity with the visceral fat area of less than 100 cm$^2$, and seventeen as visceral obesity with the visceral fat area of 100 cm$^2$ or more.

Figure 14:
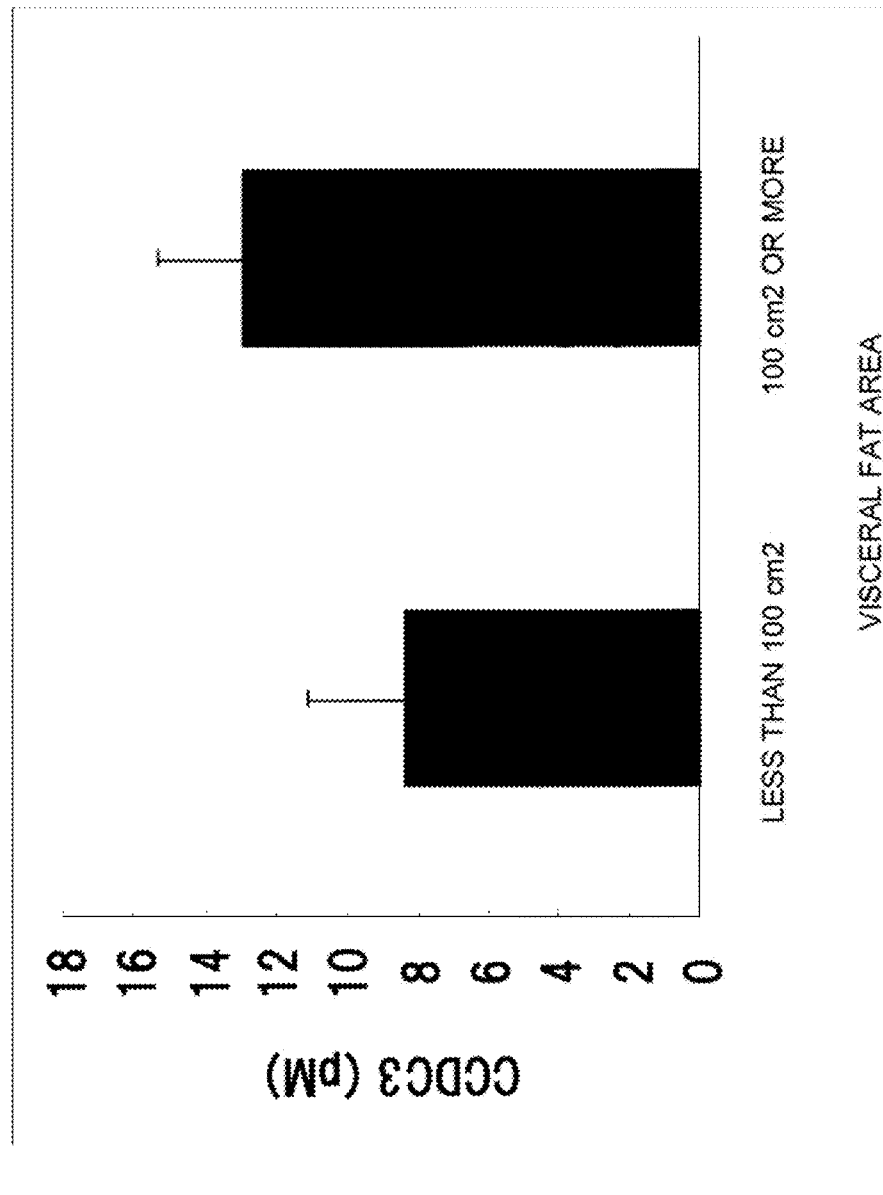
FIG. 14 represents the result of the comparison of blood plasma CCDC3 protein concentrations between a non-visceral obesity group with a visceral fat area below 100 cm$^2$ and a visceral obesity group with a visceral fat area of 100 cm$^2$ or more (Example 14).
Figure 15:
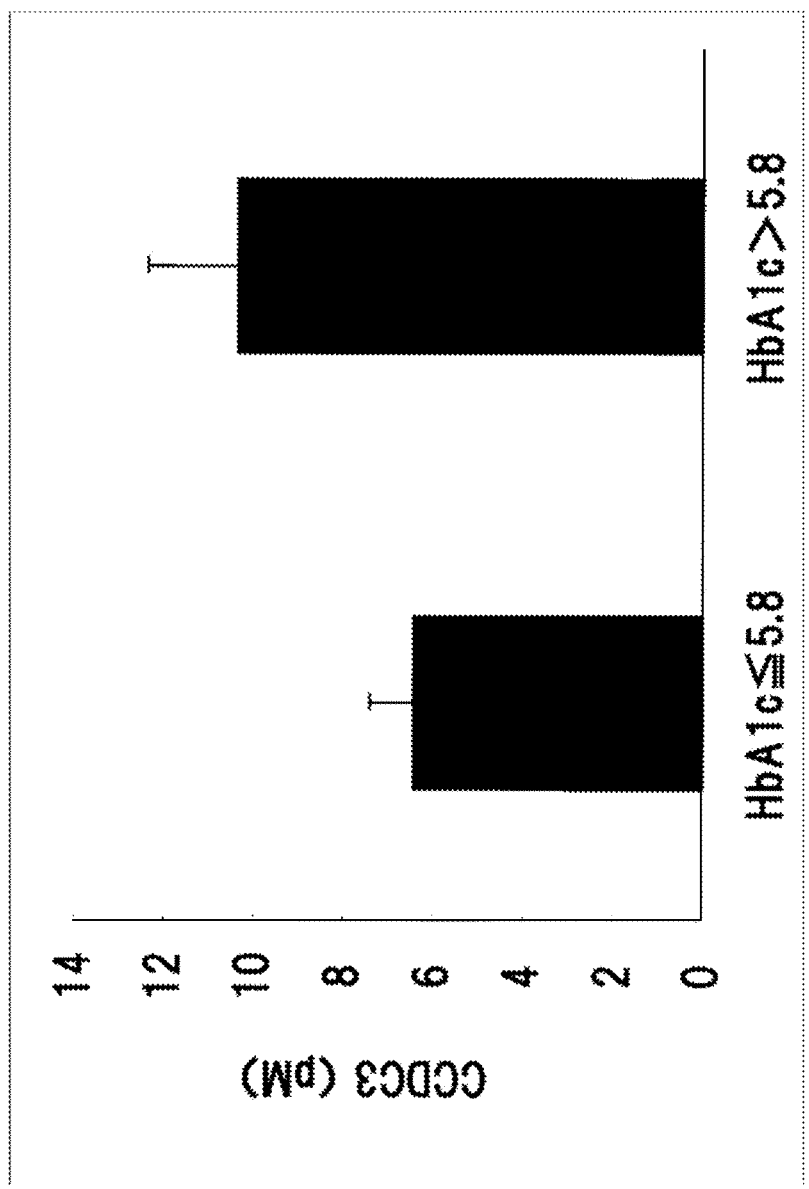
FIG. 15 represents the result of the comparison of blood plasma CCDC3 protein concentrations between a normal value group with a HbA1c value of 5.8% or less and a high value group with a HbA1c value above 5.8%, where HbA1c is an index reflecting a long-term glucose level (Example 14).

(2) Measurement of CCDC3 Protein Concentration in Human Blood Plasma and Correlation Analysis with the Extent of Obesity Measurements of CCDC3 protein concentration in the blood plasma revealed that the blood plasma CCDC3 protein concentration was higher in the visceral obesity group (17 subjects) with the visceral fat area of 100 cm$^2$ or more than in the non-visceral obesity group (8 subjects) with the visceral fat area of less than 100 cm$^2$ (FIG. 14). Further, by comparing the blood plasma CCDC3 protein concentration between a subject group (64 subjects) with the normal HbA1c values of 5.8% or less and a subject group (21 subjects) with the HbA1c values above 5.8% (HbA1c is an index that reflects long-term glucose levels), it was found that the CCDC3 protein blood plasma concentration was higher in the HbA1c>5.8% subject group than in the HbA1c S 5.8% subject group, as shown in FIG. 15.

Example 15

CCDC3 Expression Analysis in Obesity Model DIO Mouse Adipose Tissue by Immunostaining (1) Mouse Adipose Tissue Perfusion Fixation DIO mice were produced by giving the high-fat diet (HFD) 58Y1 DIO P.D. 60% Energy From Fat-Blue (Japan SLC) to C57BL/6J Jcl male mice (CLEA Japan), 7 weeks old, for 31 weeks. Mice that had the CLEA Rodent Diet CE-2 (CLEA Japan) for 43 weeks were used as control group mice. Each mouse was subjected to laparotomy under halothane anesthesia, and a syringe was inserted near the aorta from the left ventricle of the heart. After cutting the tip of the right auricle of the right atrial appendage, the tissue was washed by a reflux of phosphate buffer saline (Lonza). The tissue was then fixed by perfusion with 4% paraformaldehyde (TAAB). Thereafter, mesenteric adipose tissue (visceral adipose tissue) and subcutaneous adipose tissue were collected, and fixed in a paraformaldehyde solution.

(2) Immunostaining

Frozen thin slices (10 μm thick) were produced from the collected adipose tissues under −35 to −40° C. conditions. These were dipped in a phosphate buffer to accommodate the tissues to the wet state, and washed for 3 min in phosphate buffer after being dipped in Avidin blocking solution (Avidin/Biotin Blocking Kit (VECTOR)) for 15 min. The tissue slices were further washed for 3 min in phosphate buffer after being dipped in Biotin blocking solution (Avidin/Biotin Blocking Kit (VECTOR)) for 15 min. The samples were then placed in a slice slide moist chamber, and reacted for 60 min in a M.O.M Mouse IgG Blocking Reagent (M.O.M. Immunodetection Kit (VECTOR)) solution. Then, primary antibodies (mouse monoclonal 13D4) diluted to a 10 μg/ml, concentration with an M.O.M. diluting solution were dipped in the same moist chamber at ordinary temperature for 30 min. After being washed three times with phosphate buffer for 5 min, the samples were treated for 10 min with M.O.M. Biotinylated Anti-Mouse (horse) IgG Reagent used as the secondary antibodies. The samples were then washed three times with phosphate buffer for 5 min, and reacted with Vectastain ABC-AP Reagent (ABC-AP Universal Kit (VECTOR)) for 5 min. After being washed three times with phosphate buffer for 5 min, the samples were treated with a levamisol-added Alkaline Phosphatase substrate solution (BCIP/NBT solution (VECTOR); pH 9.5) to develop color for about 5 min. The samples were gently washed with phosphate buffer, and prepared as specimens after aqueous mounting with Aqua Poly/Mount (BioSciences).

Figure 16:
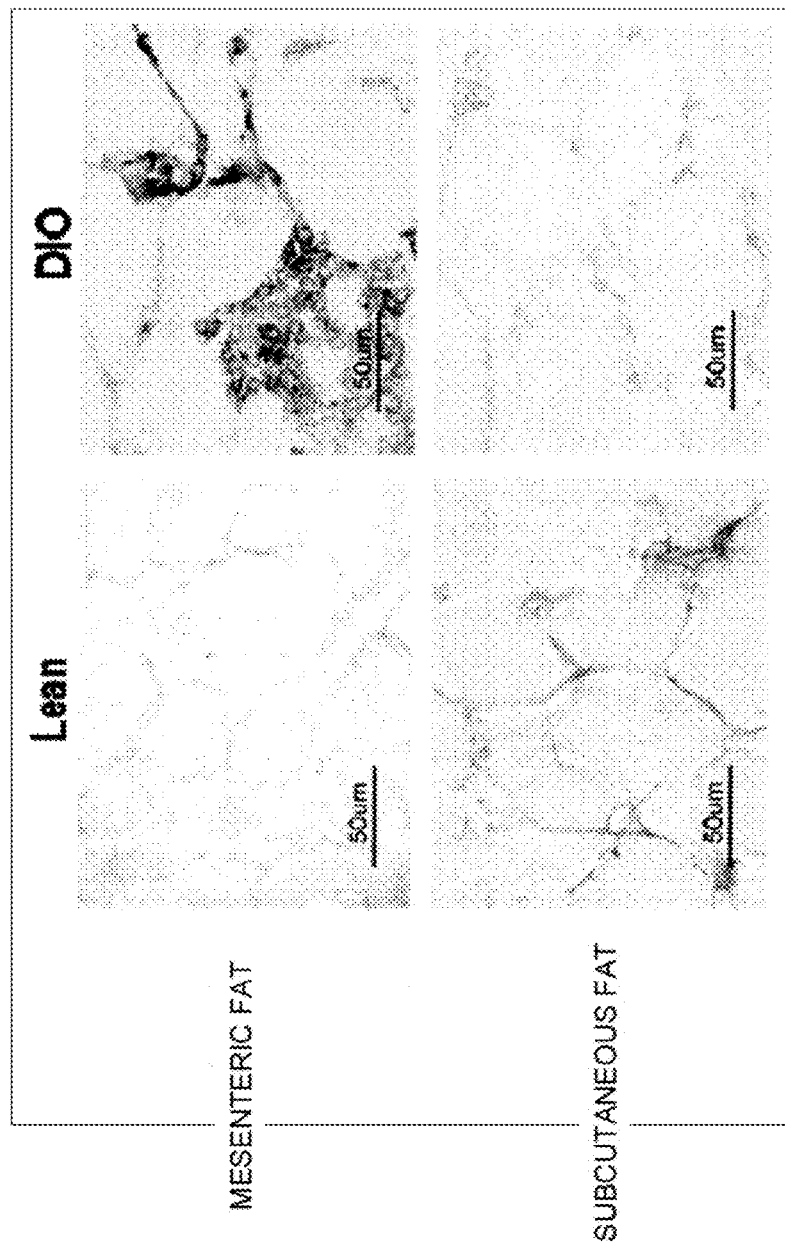
FIG. 16 represents CCDC3 protein immunostained images of the mesenteric fat and subcutaneous fat of control group mice (Lean) and DIO mice (DIO) (Example 15).

FIG. 16 represents the result of the observation of the specimens under a microscope. It was found that, compared to the mesenteric fat of the control group mice, the DIO mouse mesenteric fat had clearly more cells stained dark blue, an indicator of CCDC3 expression and production. The mesenteric fat of the DIO mice was thus found to have more enhanced CCDC3 protein expression and production over the control group. On the other hand, in the subcutaneous fat, the immunostained image did not show any difference between the control group mice and the DIO mice, suggesting that there was no difference in the amount of CCDC3 protein expression and production. The results therefore demonstrated that an increase in CCDC3 protein expression and production in the adipose tissue of obesity mice was specific to the visceral adipose tissue (mesenteric adipose tissue).

Sequence Listing Free Text

SEQ ID NOS:5 to 10 are the bases sequences of the siRNA for the CCDC3 gene concerned with the present invention SEQ ID NOS:11 and 12 are the base sequences of rat G6 Pase real-time quantitative PCR primers (forward primer, reverse primer)

SEQ ID NOS:13 and 14 are the base sequences of rat Rps18 real-time quantitative PCR primers (forward primer, reverse primer)

SEQ ID NOS:15 and 16 are the base sequences of mouse CCDC3 real-time quantitative PCR primers (forward primer, reverse primer)

SEQ ID NOS:17 and 18 are the base sequences of mouse 36B4 real-time quantitative PCR primers (forward primer, reverse primer) base sequence SEQ ID NO:19 is the base sequence of CCDC3 EcoRI—F3 primer SEQ ID NO:20 is the base sequence of CCDC3 BamHI—R3 primer SEQ ID NO:21 is the base sequence of CCDC3 Kozak-F primer SEQ ID NO:22 is the base sequence of CCDC3 STOP-R primer SEQ ID NO:23 is the base sequence of CCDC3-F1 primer SEQ ID NO:24 is the base sequence of CCDC3-R1 primer SEQ ID NO:25 is the base sequence of CCDC3-QPCR-F primer SEQ ID NO:26 is the base sequence of CCDC3-QPCR-R primer SEQ ID NO:27 is the base sequence of mGAPDH-QPCR-F primer SEQ ID NO:28 is the base sequence of mGAPDH-QPCR-R primer SEQ ID NO:29 is the amino acid sequence of the C-terminus partial peptide (259-270 region) of human CCDC3 protein SEQ ID NO:30 is the amino acid sequence of the heavy-chain variable domain of 3H6 antibody SEQ ID NO:31 is the amino acid sequence of the CDR1 of the heavy-chain variable domain of 3H6 antibody SEQ ID NO:32 is the amino acid sequence of the CDR2 of the heavy-chain variable domain of 3H6 antibody SEQ ID NO:33 is the amino acid sequence of the CDR3 of the heavy-chain variable domain of 3H6 antibody SEQ ID NO:34 is the amino acid sequence of the light-chain variable domain of 3H6 antibody SEQ ID NO:35 is the amino acid sequence of the CDR1 of the light-chain variable domain of 3H6 antibody SEQ ID NO:36 is the amino acid sequence of the CDR2 of the light-chain variable domain of 3H6 antibody SEQ ID NO:37 is the amino acid sequence of the CDR3 of the light-chain variable domain of 3H6 antibody SEQ ID NO:38 is the amino acid sequence of the heavy-chain variable domain of 6G12 antibody SEQ ID NO:39 is the amino acid sequence of the CDR1 of the heavy-chain variable domain of 6G12 antibody SEQ ID NO:40 is the amino acid sequence of the CDR2 of the heavy-chain variable domain of 6G12 antibody SEQ ID NO:41 is the amino acid sequence of the CDR3 of the heavy-chain variable domain of 6G12 antibody SEQ ID NO:42 is the amino acid sequence of the light-chain variable domain of 6G12 antibody SEQ ID NO:43 is the amino acid sequence of the CDR1 of the light-chain variable domain of 6G12 antibody SEQ ID NO:44 is the amino acid sequence of the CDR2 of the light-chain variable domain of 6G12 antibody SEQ ID NO:45 is the amino acid sequence of the CDR3 of the light-chain variable domain of 6G12 antibody SEQ ID NO:46 is the amino acid sequence of the heavy-chain variable domain of 11E10 antibody SEQ ID NO:47 is the amino acid sequence of the CDR1 of the heavy-chain variable domain of 11E10 antibody SEQ ID NO:48 is the amino acid sequence of the CDR2 of the heavy-chain variable domain of 11E10 antibody SEQ ID NO:49 is the amino acid sequence of the CDR3 of the heavy-chain variable domain of 11E10 antibody SEQ ID NO:50 is the amino acid sequence of the light-chain variable domain of 11E10 antibody SEQ ID NO:51 is the amino acid sequence of the CDR1 of the light-chain variable domain of 11E10 antibody SEQ ID NO:52 is the amino acid sequence of the CDR2 of the light-chain variable domain of 11E10 antibody SEQ ID NO:53 is the amino acid sequence of the CDR3 of the light-chain variable domain of 11E10 antibody Sequence Listing
PCT_visceral obesity test_20100512_204601_1.txt

The invention claimed is:

1. A method for detecting visceral obesity using, as an index, the amount of mRNA expression of coiled-coil domain containing protein 3 (CCDC3) or the amount of the product CCDC3 protein in a test sample collected from a subject, comprising the steps of:
   (1) measuring the amount of CCDC3 mRNA expression or the amount of the product CCDC3 protein in the test sample collected from the subject;
   (2) comparing the measured CCDC3 mRNA expression amount (subject expression amount) or the measured amount of the product CCDC3 protein (subject production amount) with the CCDC3 mRNA expression amount (control expression amount) or the amount of the product CCDC3 protein (control production amount) in a control sample derived from a non-visceral obesity individual; and
   (3) determining visceral obesity in the subject by using a higher subject expression amount or a higher subject production amount than the control expression amount or the control production amount as an index.

2. The method according to claim 1, wherein the method uses an antibody that recognizes coiled-coil domain containing protein 3 (CCDC3) protein, and is selected from the group of the following antibodies (1) to (3):
   (1) an antibody having amino acid sequences of SEQ ID NOS:31, 32, and 33 for the CDR1, CDR2, and CDR3, respectively, of the heavy-chain variable domain, and amino acid sequences of SEQ ID NOS:35, 36, and 37 for the CDR1, CDR2, and CDR3, respectively, of the light-chain variable domain;
   (2) an antibody having amino acid sequences of SEQ ID NOS:39, 40, and 41 for the CDR1, CDR2, and CDR3, respectively, of the heavy-chain variable domain, and amino acid sequences of SEQ ID NOS:43, 44, and 45 for the CDR1, CDR2, and CDR3, respectively, of the light-chain variable domain; and
   (3) an antibody having amino acid sequences of SEQ ID NOS:47, 48, and 49 for the CDR1, CDR2, and CDR3, respectively, of the heavy-chain variable domain, and amino acid sequences of SEQ ID NOS:51, 52, and 53 for the CDR1, CDR2, and CDR3, respectively, of the light-chain variable domain.

* * * * *